295

(12) United States Patent
Guss et al.

(10) Patent No.: US 9,987,342 B2
(45) Date of Patent: Jun. 5, 2018

(54) IMMUNIZING COMPOSITION

(71) Applicant: INTERVACC AB, Hagersten (SE)

(72) Inventors: Bengt Guss, Uppsala (SE);
Jan-Ingmar Flock, Bromma (SE);
Lars Frykberg, Storvereta (SE);
Margareta Flock, Bromma (SE)

(73) Assignee: INTERVACC AB, Hagersten (SE)

( * ) Notice: Subject to any disclaimer, the term of this patent is extended or adjusted under 35 U.S.C. 154(b) by 981 days.

(21) Appl. No.: 13/893,212

(22) Filed: May 13, 2013

(65) Prior Publication Data
US 2014/0220064 A1    Aug. 7, 2014

Related U.S. Application Data

(63) Continuation of application No. 12/747,843, filed as application No. PCT/SE2008/051445 on Dec. 12, 2008, now abandoned.

(60) Provisional application No. 61/082,281, filed on Jul. 21, 2008, provisional application No. 61/013,495, filed on Dec. 13, 2007.

(51) Int. Cl.
*A61K 39/09*     (2006.01)
*C12N 15/09*     (2006.01)
*C07K 16/12*     (2006.01)
*A61P 31/04*     (2006.01)
*C07K 14/315*    (2006.01)
*A61K 39/00*     (2006.01)

(52) U.S. Cl.
CPC .......... *A61K 39/092* (2013.01); *C07K 14/315* (2013.01); *A61K 2039/552* (2013.01)

(58) Field of Classification Search
None
See application file for complete search history.

(56) References Cited

U.S. PATENT DOCUMENTS

| | | |
|---|---|---|
| 6,120,775 A | 9/2000 | Jacobs |
| 2002/0110562 A1 | 8/2002 | Adamou et al. |
| 2006/0140980 A1 | 6/2006 | Guss et al. |
| 2007/0243195 A1 | 10/2007 | Minke et al. |

FOREIGN PATENT DOCUMENTS

| | | | |
|---|---|---|---|
| JP | 2003-501110 A | 1/2003 | |
| WO | WO 00/37496 A1 | 6/2000 | |
| WO | WO 2004/032957 A1 | 4/2004 | |
| WO | WO 2007115059 A2 * | 10/2007 | ........... A61K 39/092 |

OTHER PUBLICATIONS

English translation of the Japanese Office Action for Application No. 2010-537898 dated Apr. 23, 2013.
European Office Action dated Sep. 12, 2012 for European Application No. 08858722.5.
European Search Report dated Jul. 29, 2011, in European Patent Application No. 08858722.5.
Flock et al., "Protective effect of vaccination with recombinant proteins from *Streptococcus equi* subspecies *equi* in a strangles model in the mouse," Vaccine (2006) vol. 24, pp. 4144-4151.
Flock et al., "Recombinant *Streptococcus equi* Proteins Protect Mice in Challenge Experiments and Induce Immune Response in Horses," Infection and Immunology (Jun. 2004) vol. 72, No. 6, pp. 3228-3236.
Guss et al., "Getting to Grips with Strangles: An Effective Multi-Component Recombinant Vaccine for the Protection of Horses from *Streptococcus equi* Infection," PLoS Pathogens (Sep. 2009) vol. 5, No. 9, pp. 1-9.
Lannergard et al., "IdeE and IgG-endopeptidase of *Streptococcus equi* ssp. *equi*," FEMS Microbiol. Lett. (2006) vol. 262, pp. 230-235.
Timoney et al., "IdeE reduces the bactericidal activity of equine neutrophils for *Streptococcus equi*," Veterinary Immunology and Immunopathology, vol. 122, 2008, pp. 76-82, XP022494652.
Waller et al., "Getting a grip on strangles: Recent progress towards improved diagnostics and vaccines," The Veterinary Journal (2007) vol. 173, pp. 492-501.
Waller et al., "Vaccination of horses against strangles using recombinant antigens from *Streptococcus equi*," Vaccine (2007) vol. 25, pp. 3629-3635.
International Search Report dated Mar. 23, 2009 for International Application No. PCT/SE2008/051445.

* cited by examiner

*Primary Examiner* — Robert A Zeman
(74) *Attorney, Agent, or Firm* — Birch, Stewart, Kolasch & Birch, LLP

(57) ABSTRACT

The present invention is concerned with an antigenic composition comprising at least one antigen that comprises at least one antigenic epitope or antigenic determinant derived from a protein present in one or both of *S. equi* subsp. *equi* and subsp. *zooepidemicus* and use thereof for immunization of non-human mammals against *S. equi* subsp. *equi* and/or subsp. *zooepidemicus*. The present invention also discloses a vaccine composition comprising the aforesaid antigenic composition as immunizing component.

10 Claims, 19 Drawing Sheets

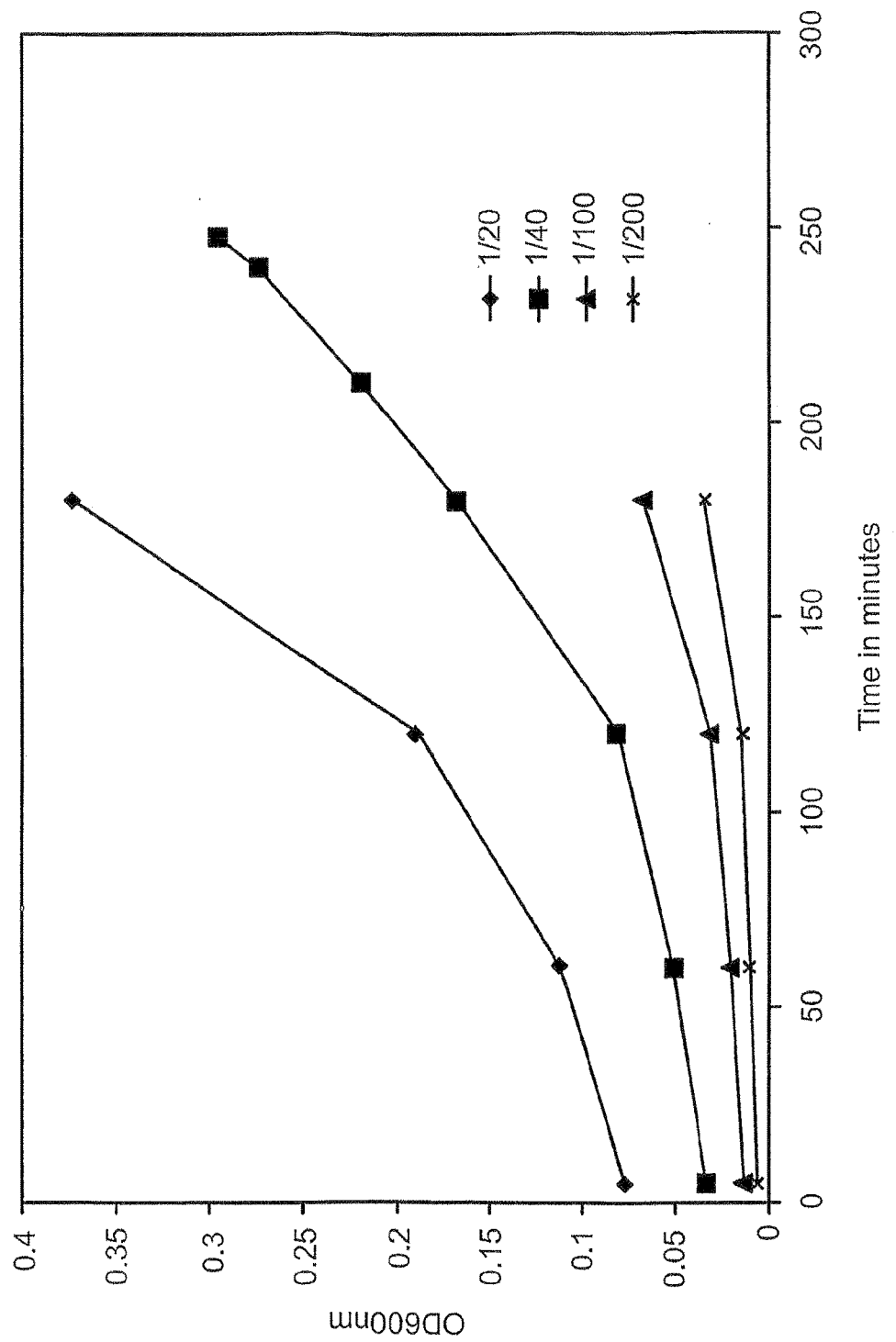
Figure 6: GROWTH OF CHALLENGE INCOLUM 08/5/08

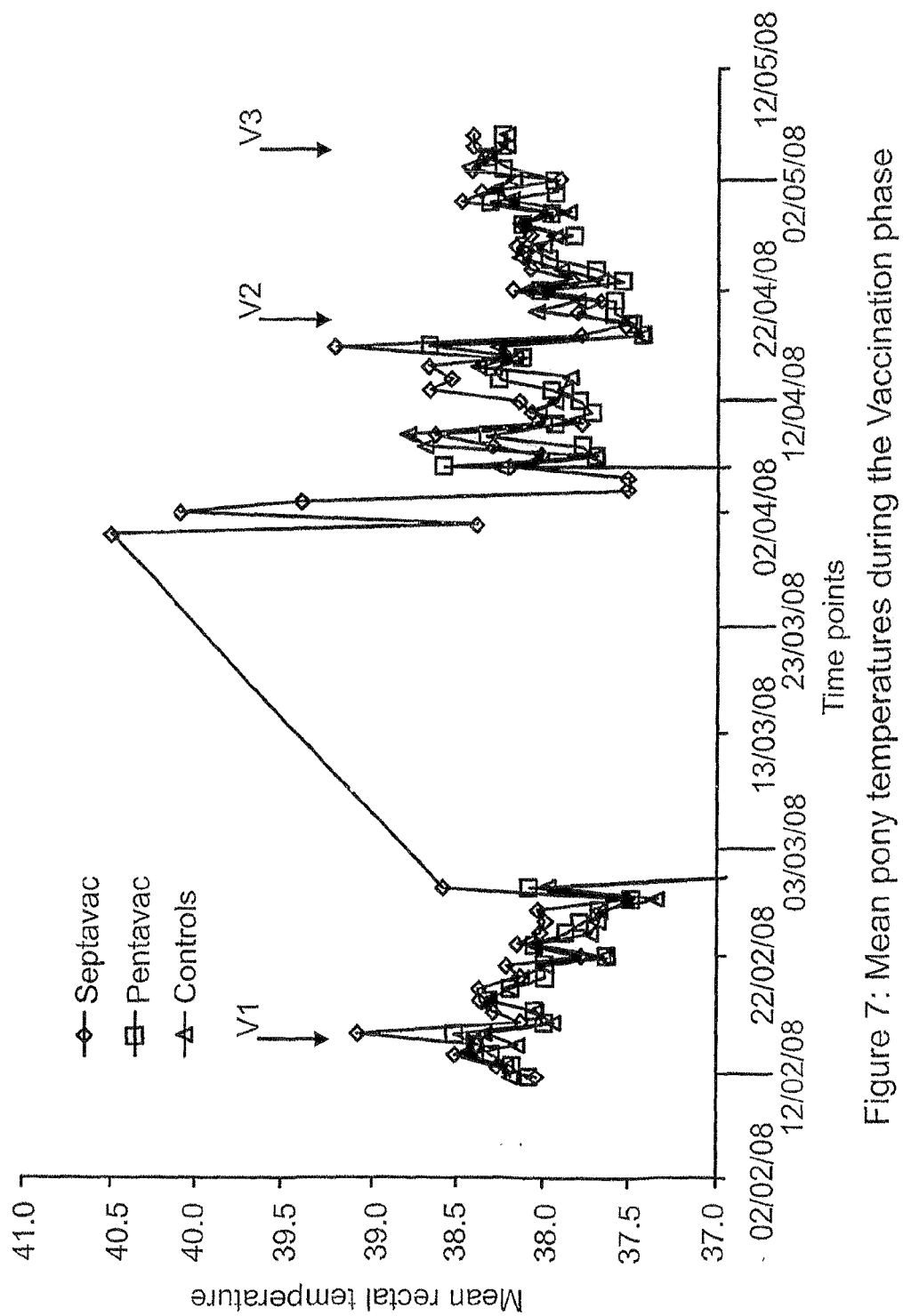
Figure 7: Mean pony temperatures during the Vaccination phase

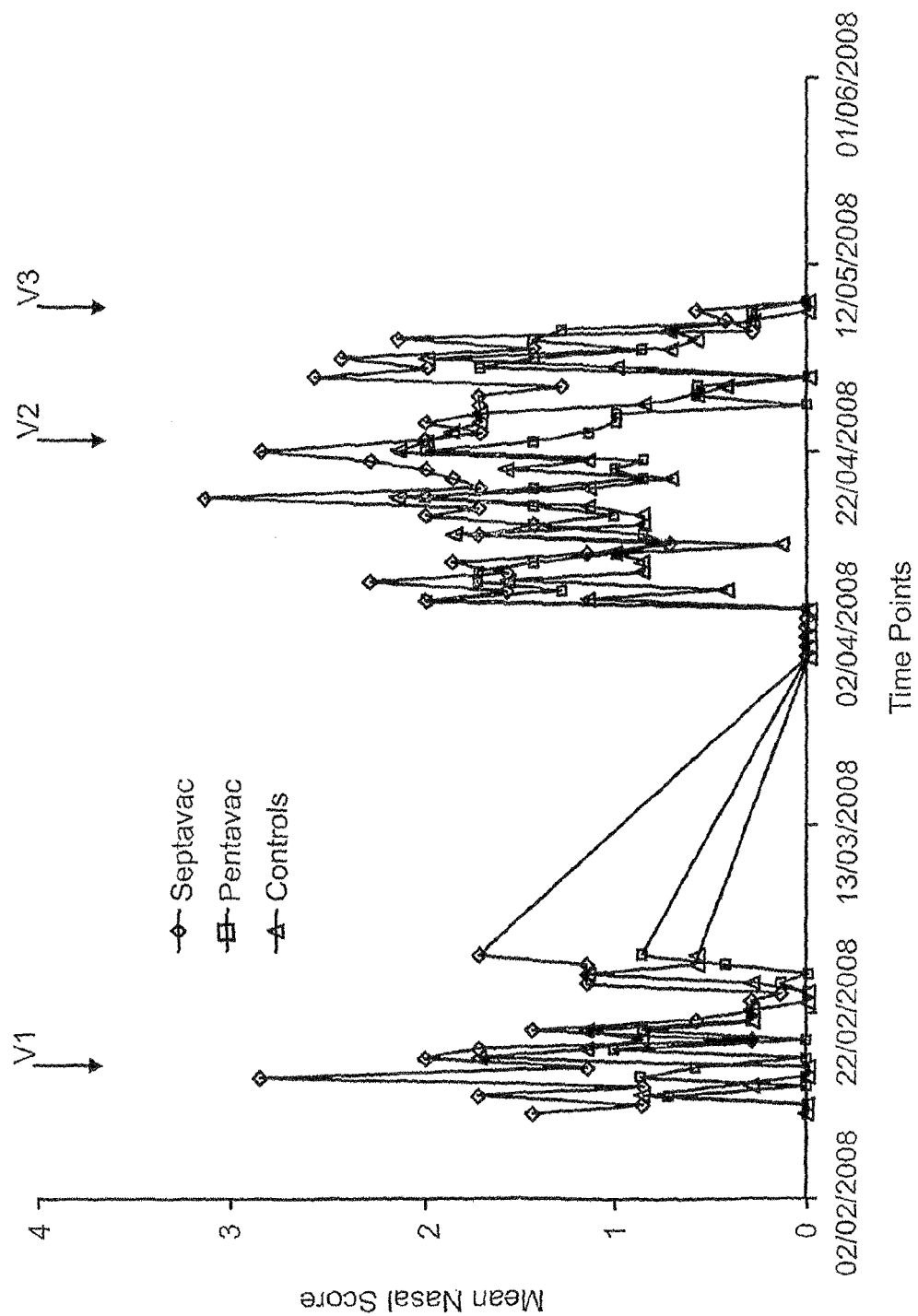
Figure 8: Mean nasal score during the vaccination phase

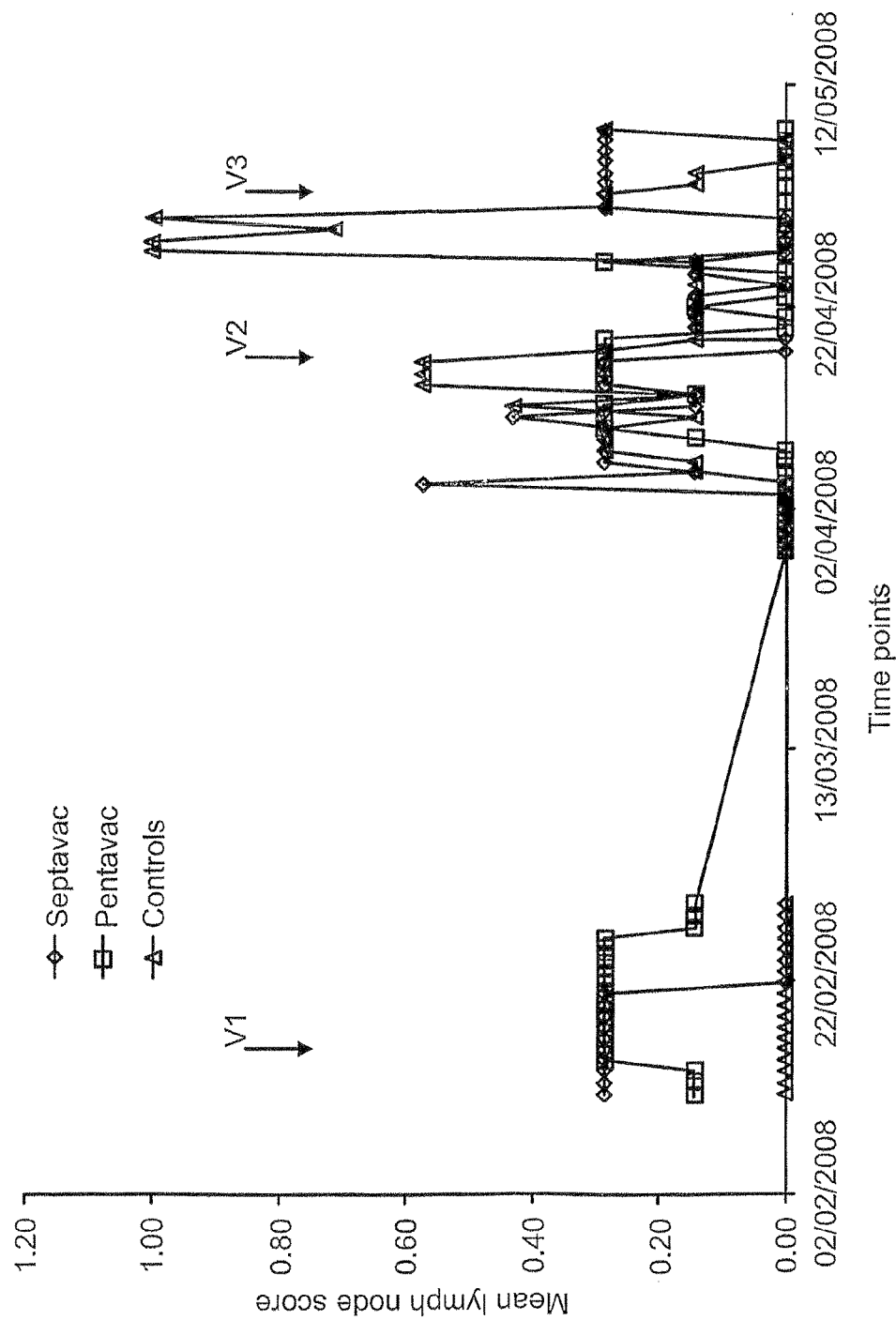
Figure 9: Mean lymph node score during the vaccination phase

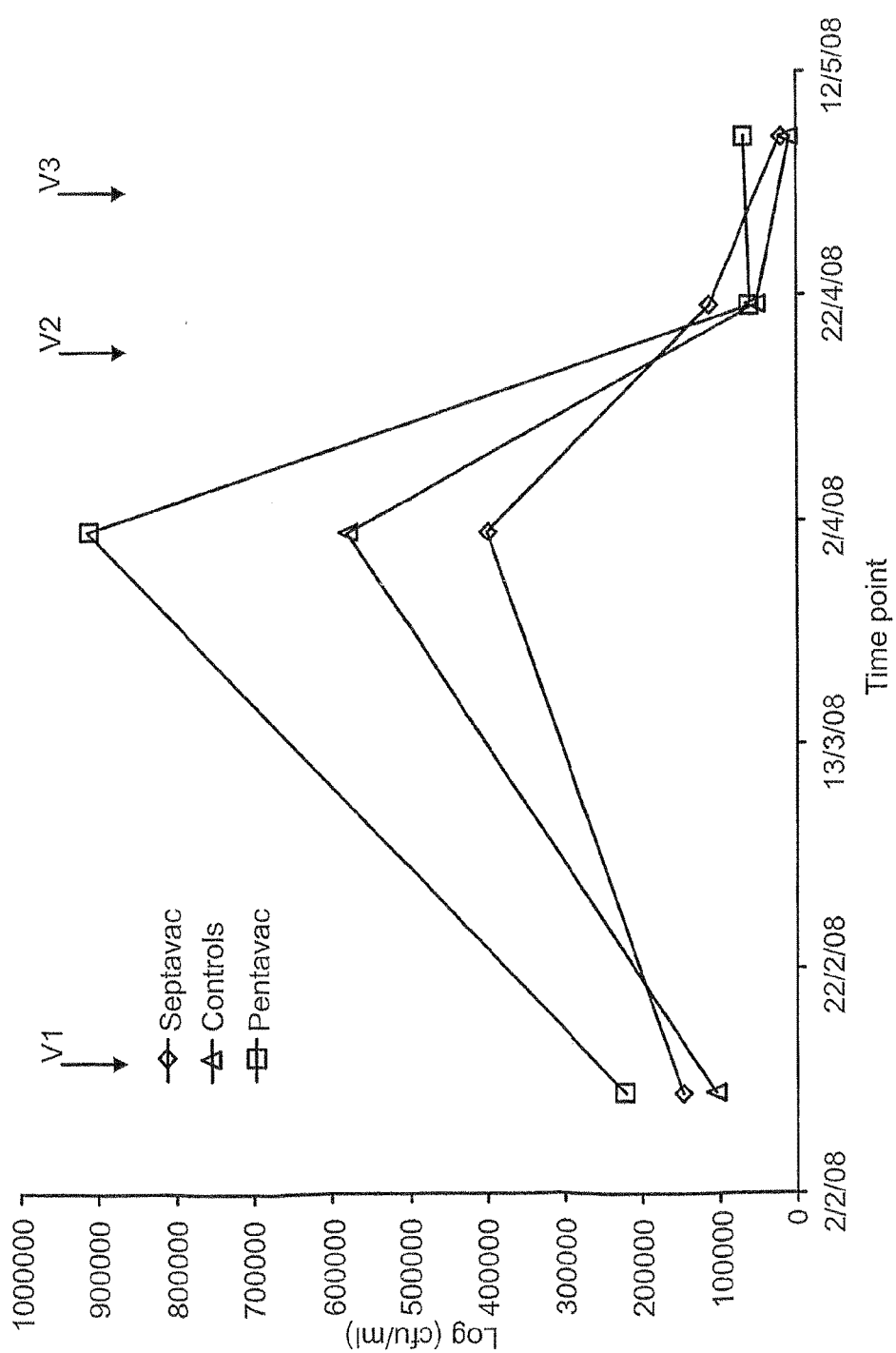
Figure 10: Mean counts of S. zooepidemicus in nasal washes during the vaccination phase

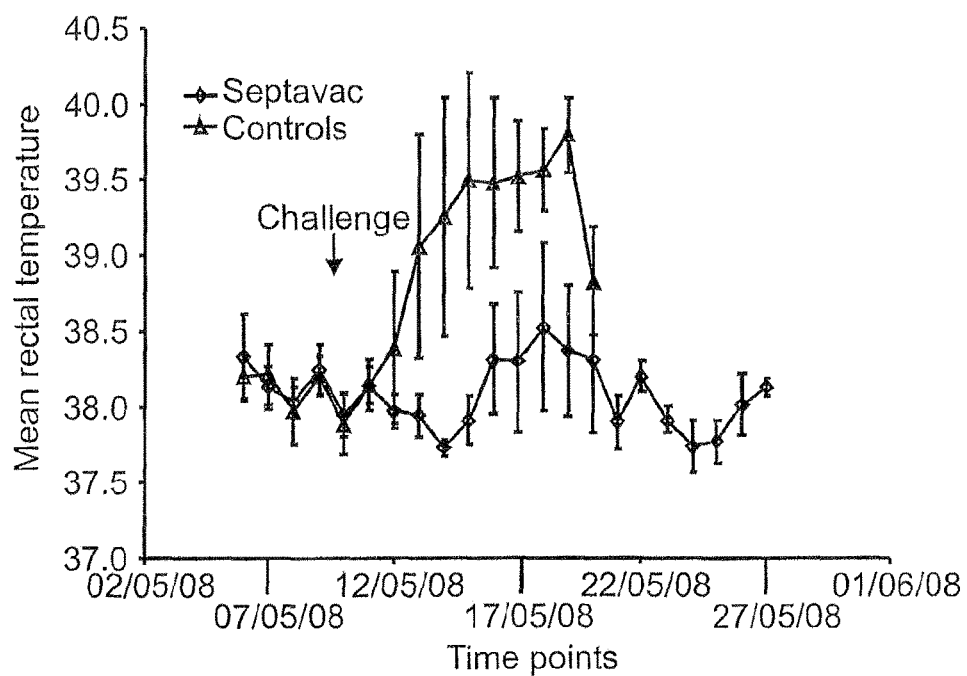
* All control ponies were euthanased by day 13 of the study, but most would have continued to have elevated temperatures had they not been euthanased on welfare grounds.
Figure 11: Mean temperatures after challange

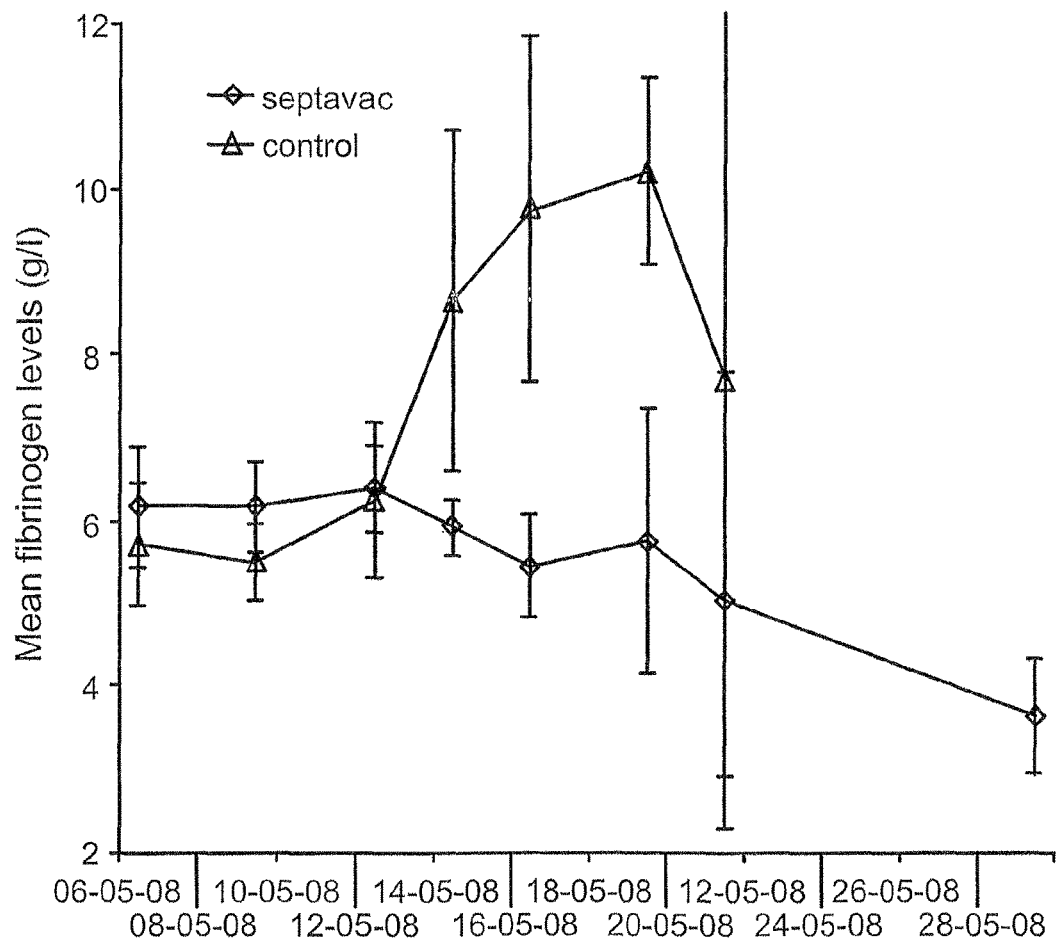
Figure 12: Mean fibrinogen levels during the challenge phase

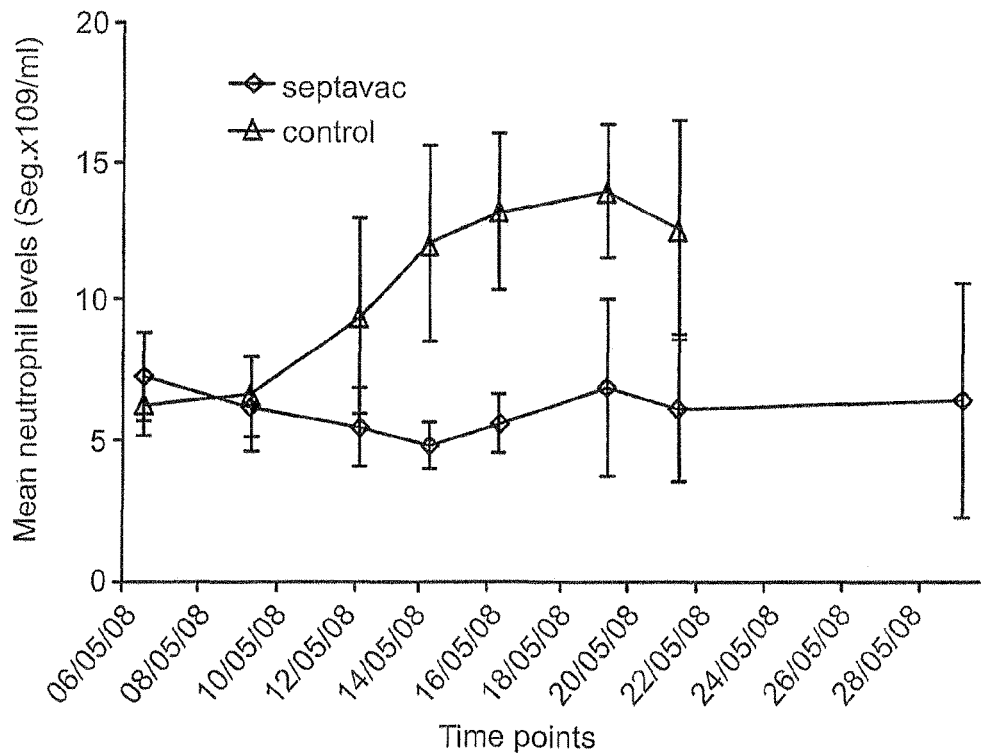
* All control ponies were euthanased by day 13 post-challenge, but most would have continued to have elevated neutrophil levels had they not been euthanased on welfare grounds.
Figure 13: Neutrophil levels during challenge phase

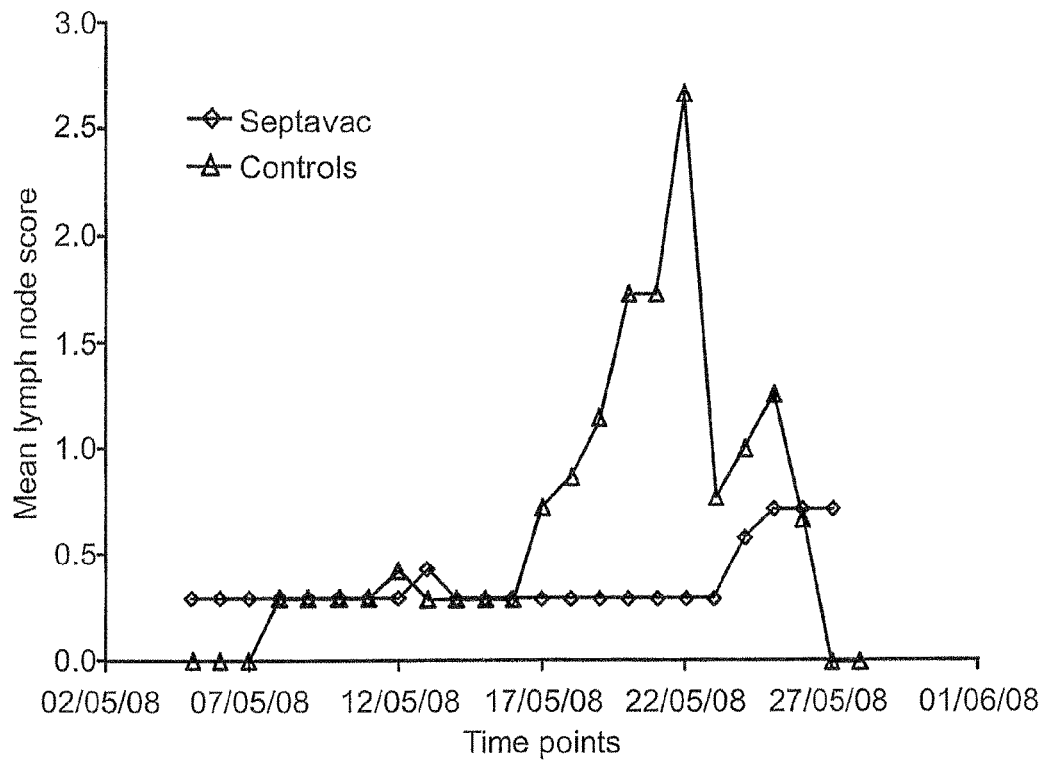
* All control ponies were euthanased by day 13 post-challenge, but most would have continued to have elevated lymph node scores had they not been euthanased on welfare grounds.
Figure 14: Mean lymph node score during challenge phase

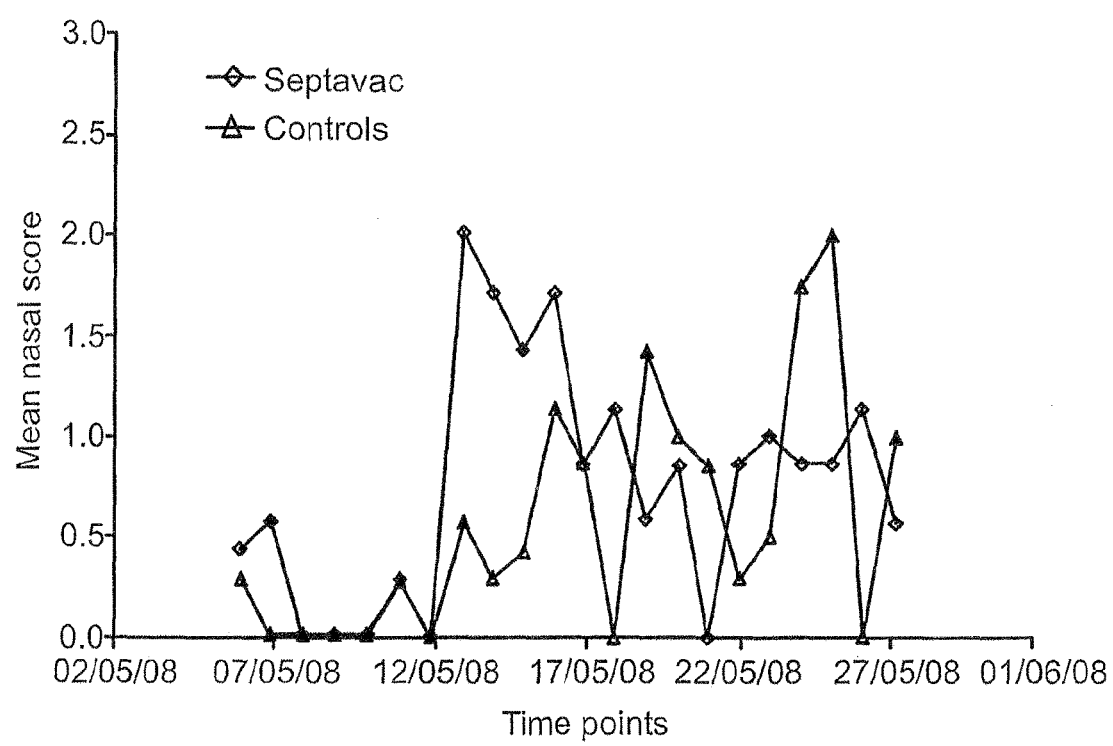
Figure 15: Mean nasal score during challenge phase

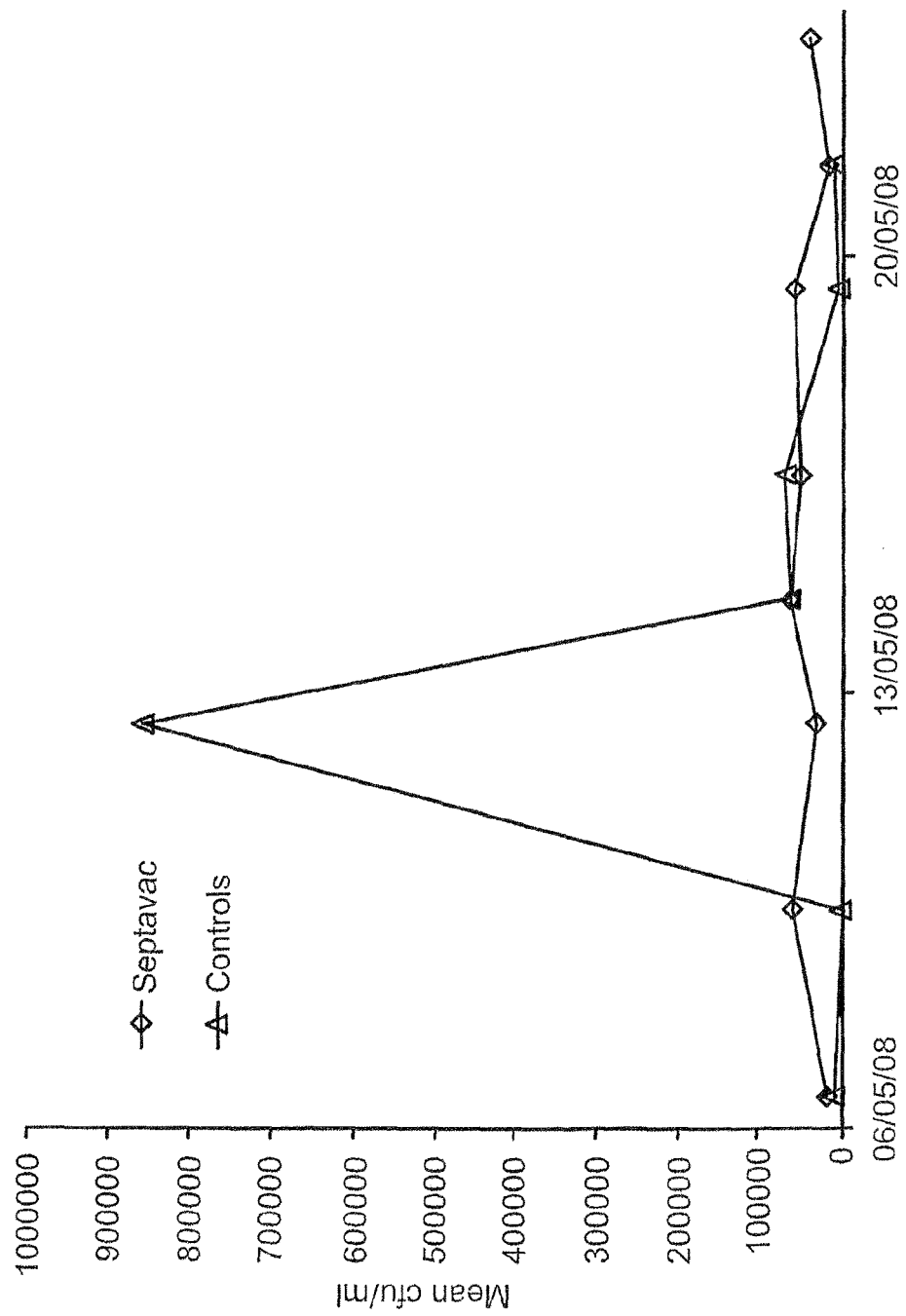
Figure 16: Mean S. zooepidemicus counts during challenge phase

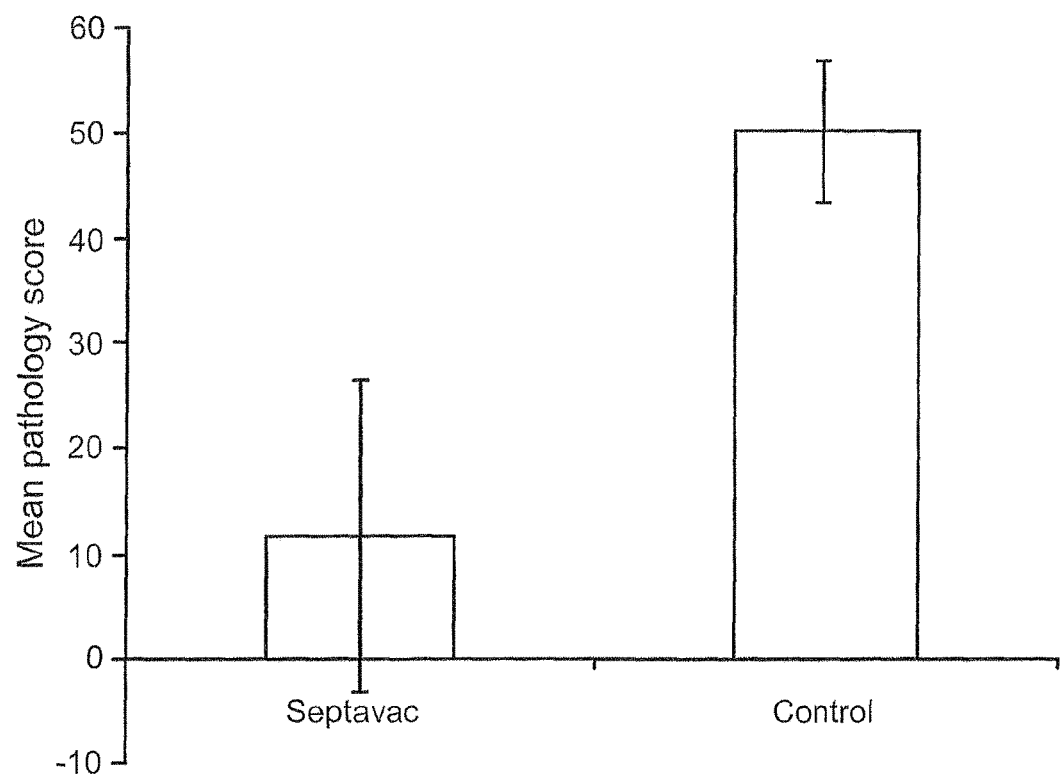
Figure 17: Mean pathology score on post mortem examination

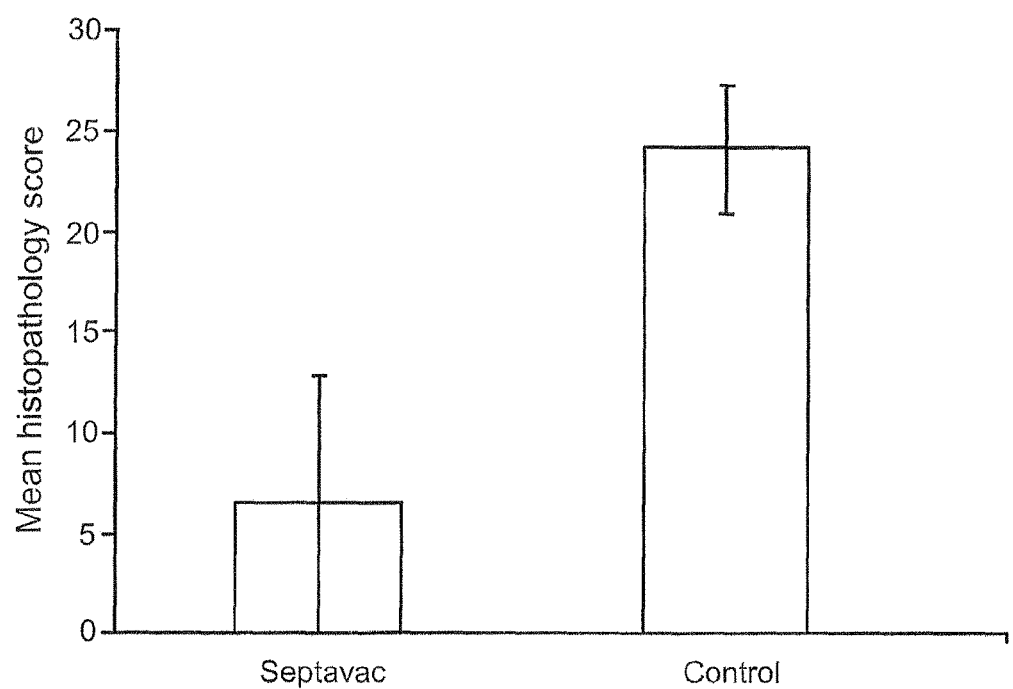
Figure 18: Mean Histopathology Scores

IMMUNIZING COMPOSITION

CROSS REFERENCE TO RELATED APPLICATIONS

This application is a Continuation of application Ser. No. 12/747,843 filed on Oct. 6, 2010 (now abandoned), which is a national phase application of International Application No. PCT/SE2008/051445, filed Dec. 12, 2008, which claims priority to U.S. Provisional Application No. 61/013,495 filed on Dec. 13, 2007 and U.S. Provisional Application No. 61/082,281 filed on Jul. 21, 2008. The entire contents of all of the above applications is hereby incorporated by reference.

REFERENCE TO SEQUENCE LISTING SUBMITTED VIA EFS-WEB

This application includes an electronically submitted sequence listing in .txt format. The .txt file contains a sequence listing entitled "2016-06-10 0104-0901PUS2_ST25.txt" created on Jun. 10, 2016 and is 70,745 bytes in size. The sequence listing contained in this .txt file is part of the specification and is hereby incorporated by reference herein in its entirety.

BACKGROUND OF THE INVENTION

1. Field of the Invention

This invention is generally related to antigenic or immunogenic compositions and use thereof for immunization of non-human mammals, e.g. horses, against *Streptococcus equi*.

2. Background of the Invention

Streptococcal infections in horses are mainly caused by the species *Streptococcus equi*, which is classified as a Lancefield Group C *Streptococcus* and comprises two subspecies designated *equi* and *zooepidemicus*, respectively.

*Streptococcus equi* subsp. *equi*, which is virtually confined to horses, is the causative agent of strangles, a world-wide distributed and highly contagious serious disease of the upper respiratory tract of the Equidae. Strangles is one of the most frequently reported equine diseases world-wide and is characterized by fever, nasal discharge, and abscess formation in the retropharyngeal and mandibular lymph nodes. In some cases the disease shows a metastatic course in the body, so called "bastard strangles". The disease has a world-wide distribution and causes great economic losses. Moreover, since strangles is a highly contagious disease, not only infected animals but also all other members of e.g. an afflicted stud must be isolated for as long as up to three months.

*S. equi* subsp. *zooepidemicus* is considered as an opportunistic commensal often occurring in the upper respiratory tract of healthy horses. However, after stress or virus infection, it can cause a secondary infection, which results in strangles-like symptoms. Moreover, subsp. *zooepidemicus* infects not only horses but also a wide range of other animals, like pigs, dogs, cats, and cows. Even human cases of infection due to subsp. *zooepidemicus* have been reported. This subspecies has been implicated as the primary pathogen in conditions such as endometritis, cervicitis, abortion, mastitis, pneumonia, abscesses and joint infections.

Although it is possible to treat and cure these streptococcal infections with antibiotics, such as penicillin, tetracycline or gentamicin, an effective prophylactic agent that could prevent outbursts of such infections and obviate or reduce the risk for development of resistant strains associated with antibiotic treatment, would be appreciated.

3. Description of the Related Art

However, although many attempts have been made to develop prophylactic agents such as vaccines against *S. equi*, at the present time no efficient vaccines or immunizing preparations are available, neither for the subspecies *equi* nor for the subspecies *zooepidemicus*.

Existing vaccines against strangles are based on inactivated, e.g. heat-killed, or attenuated strains of *S. equi* subsp. *equi* or acid extracts/mutanolysin enriched in M-protein(s), i.e. immunogenic protein(s) produced by *S. equi*. A vaccine against *S. equi* subsp. *zooepidemicus* based on an M-like protein is disclosed in U.S. Pat. No. 5,583,014. In WO 87/00436, an avirulent strain of *S. equi* is disclosed for use as a vaccine against *S. equi* that stimulates an antibody response in the nasopharyngeal mucosa after administration thereof to a horse.

Recently, a commercial vaccine against strangles, Equilis StrepE from IntervetVET, UK, has been released in Great Britain (November 2004), which vaccine also has been used throughout Europe and in South Africa and South America. However, the safety and efficacy of this vaccine, which is based on an attenuated (living, deletion mutated) strain of *S. equi* subsp. *equi*, can be questioned.

Since the previously developed vaccines or immunizing preparations are hampered by side-effects and, moreover, provide insufficient protection, there is a need for efficient and safe prophylactic agents, such as vaccines, that protect against *S. equi* infections and/or prevent spread thereof without giving rise to undesirable side-effects.

It is well known that attachment to eukaryotic cell surfaces is an essential step in the establishment of infection and colonization by bacterial pathogens. Accordingly, streptococcal surface proteins, that interact with and/or bind to different components of the Extracellular Matrix (ECM) or plasma proteins of the host cell, are potential candidates for use as active component(s) for immunizing purposes.

This is illustrated by the vaccines based on M-like proteins mentioned above or disclosed in the literature, i.a. in WO 98/01561. The binding of fibrinogen and complement factor H to M-proteins is assumed to be important for the ability of streptococci to resist phagocytosis.

Another mechanism used by streptococci for attachment to host cells involves binding to the ECM component fibronectin (Fn) (Ref. 21, 22). Binding between Fn-binding bacterial cell-surface proteins and immobilized Fn promotes internalization of streptococci by epithelial cells (Ref. 2, 23, 24). Fibronectin is a dimeric glycoprotein found both in plasma and in a fibrillar form in the extracellular matrix. The main function of Fn is to mediate substrate adhesion of eukaryotic cells, which involves the binding of specific cell-surface receptors to certain domains of the Fn molecule. Furthermore, it also interacts with several other macromolecules, such as DNA, heparin, fibrin, and collagen.

Accordingly, Fn-binding proteins from different streptococcal species have been cloned and sequenced previously. For instance, from *S. equi*, one Fn-binding protein has been cloned and characterized, which is a Fn-binding cell-surface protein of subsp. *zooepidemicus*, that has been designated FNZ (Lindmark et al., 1996, Ref. 9). Another Fn-binding protein from *S. equi* subsp. *equi*, has been cloned and characterized by Lindmark and Guss (1999) (Ref. 12). This latter protein that is designated SFS and its potential use as an active component in a vaccine for protection of horses against strangles are disclosed in WO 00/37496.

In Jonsson et al. (1995) (Ref, 8), a protein designated ZAG has been cloned and characterized from *S. equi* subsp. *zooepidemicus* that mediates binding to the plasma proteinase inhibitor $\alpha_2 M$. It is speculated therein that this protein is similar in function to streptococcal M proteins. This protein, ZAG, is also disclosed in WO 95/07296, where its $\alpha_2 M$-binding properties are indicated. However, immunogenic properties or potential use thereof as an active component in a vaccine for protection of e.g. horses against strangles are not disclosed therein. The gene zag encoding ZAG is also disclosed in these references.

A gene that is similar to the aforesaid zag gene from *S. equi* subsp. *zooepidemicus* but is present in subsp. *equi* has been described by Lindmark et al. (1999) (Ref. 11) and Lindmark (1999) (Ref. 13). This gene is hereafter designated eag and encodes a protein designated EAG.

In WO 2004/032957 A1, antigenic compositions are disclosed which comprise at least one antigen derived from a protein designated EAG, which protein is present in *S. equi*, and which composition suitably comprises at least one further antigen selected from a group of proteins which are present in *S. equi* and are, designated FNZ, SFS, SEC and SclC, respectively.

In WO 2007/115059 A2, subunit immunogenic or vaccine compositions are disclosed which comprise at least one polypeptide of *S. equi* having a specific amino acid sequence as shown in the sequence listing attached to said publication or an analog thereof or a fragment thereof which is a part of said polypeptide and contains at least one epitope. However, no results as regards immunizing of horses against strangles are provided in this document.

In the study reported in Lannergård, J., Frykberg, L. and Guss, B. (2003) FEMS Microbiol Lett 222: 69-74, (Ref. 28), a new gene designated one has been isolated and the corresponding protein CNE has been characterized.

In Flock, M., Jacobsson, K., Frykberg, L., Hirst, T., R., Franklin, A., Guss, B. and Flock, J.-I. (2004) Infect Immun 72:3228-3236 (Ref. 5), it is reported that in a mouse model of equine strangles, parts of the proteins designated FNZ, SFS and EAG, respectively, were used to immunize mice. FNZ and EAG were considered as promising candidates for development of a safe and efficacious vaccine against strangles.

In Lannergård, J. and Guss, B. (2006) FEMS Microbiol Lett 262: 230-235, (Ref. 26), two new proteins, IdeE and IdeZ, from *S. equi* subspecies *equi* and *zooepidemicus*, respectively, have been characterized as regards enzymatic activities.

In Vaccine (Timoney et al.; 2007) it is reported that a great number of recombinant extracellular proteins of *S. equi*, including CNE (also designated SEC) and Se 44.2 (also designated IdeE2) are useless as vaccine components. It is speculated therein that earlier results for SEC/CNE obtained for mice are not applicable to horses. Thus, it is not obvious that recombinant forms of surface localized proteins necessarily are likely candidates for vaccine components.

In Waller, A., Flock, M., Smith, K., Robinson, C., Mitchell, Z., Karlström, A., Lannergård, J., Bergman, R., Guss, B. and Flock, J.-I. (2007) Vaccine 25: 3629-3635, (Ref. 27), vaccination of horses against strangles using the recombinant antigens EAG, CNE and SclC from *S. equi* subspecies *equi* is reported. In this study, vaccinated horses showed, after challenge with *S. equi* subspecies *equi*, significantly reduced recovery of bacteria and significantly lower levels of nasal discharge.

Although many efforts have been made to develop efficient vaccines and some of the immunizing components of WO 2004/032957 A1 are promising candidates for use in a vaccine that protects against *S. equi* infection, development of safe vaccines having a high degree of immunogenicity and exhibiting limited or no side effects is still desirable.

BRIEF SUMMARY OF THE INVENTION

The present invention is based on an antigenic, suitably an immunogenic, composition comprising at least one antigen, suitably an immunogen, that comprises at least one antigenic epitope or antigenic determinant derived from a protein present in one or both of *S. equi* subsp. *equi* and subsp. *zooepidemicus* and use thereof for immunization of non-human mammals against *S. equi* subsp. *equi* and/or subsp. *zooepidemicus*.

The present invention is also directed to a vaccine composition comprising the afore-said antigenic composition as immunizing component; to methods to prepare said antigenic, suitably immunogenic, composition or vaccine composition; to methods to induce an immune response against *S. equi* in non-human mammals; and to methods for prophylactic or therapeutic treatment of *S. equi* infection in non-human mammals. When used generally, the expression "*S. equi*" refers to one or both of subsp, *equi* and subsp. *zooepidemicus*.

According to a suitable embodiment, the present invention is directed to a vaccine that protects equines, such as horses, against strangles.

In the context of infections caused by *S. equi* subsp. *equi*, the expression "non-human mammals" primarily refers to animals belonging to the family Equidae that consists of horses, donkeys and zebras and to hybrids thereof, such as Mules and hinnies. Camels and dromedaries are also encompassed therein.

In connection with infections caused by *S. equi* subsp. *zooepidemicus*, the expression "non-human mammals" in addition refers also to other mammals such as cows, pigs, dogs and cats.

BRIEF DESCRIPTION OF THE DRAWINGS

In the following, the present invention is described in closer detail with reference to the drawings, where.

In these FIGS. 1-5, mean values and standard errors are indicated.

FIG. 6 shows growth of challenge inoculum (*S. equi* subsp. *equi* strain 4047);

FIG. 7 shows mean pony temperatures during the vaccination phase;

FIG. 8 shows mean nasal score during the vaccination phase;

FIG. 9 shows mean lymph node score during the vaccination phase;

FIG. 10 shows mean counts of *S. zooepidemicus* in nasal washes during the vaccination phase;

FIG. 11 shows mean pony temperatures after challenge;

FIG. 12 shows mean fibrinogen levels during the challenge phase;

FIG. 13 shows mean neutrophil levels during the challenge phase;

FIG. 14 shows mean lymph node score during the challenge phase;

FIG. 15 shows mean nasal score during the challenge phase;

FIG. 16 shows mean *S. zooepidemicus* counts during challenge phase;

FIG. 17 shows mean pathology score on post mortem examination; and

FIG. 18 shows mean histopathology scores.

Figure 19:
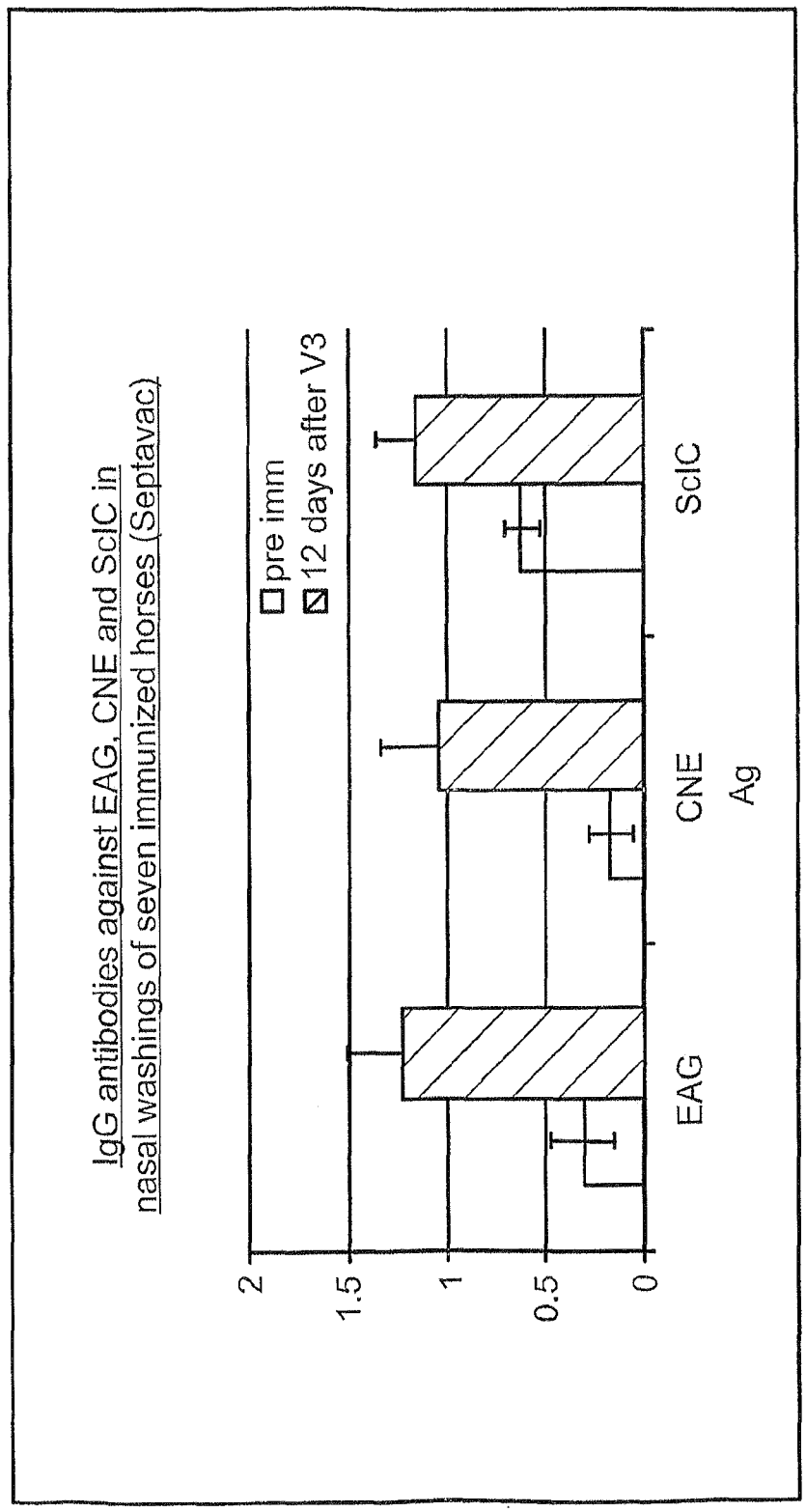

FIG. 19 shows ELISA measurements of IgG antibodies in nasal washings of seven immunized horses. The log dilution of sera required to give an absorbance value at a cut-off of 1.0 was calculated for each individual nasal wash sample. Mean values (n=7) with standard errors are shown. Samples taken before (pre imm. day 1) and twelve days after the third immunization are shown (day 86). The horses were immunized with EAG, CNE and SclC.

Figure 20:
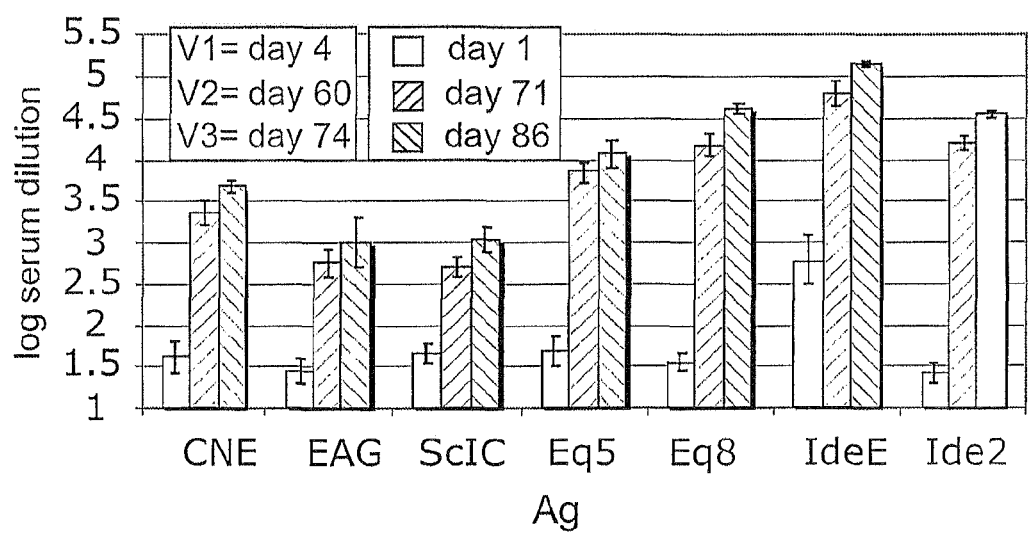

FIG. 20 shows ELISA measurements of IgG antibodies in sera of seven immunized horses. The log dilution of sera required to give an absorbance value at a cut-off of 1.5 was calculated for each individual serum sample. Mean values (n=7) with standard errors are shown. Sample taken before (day 1), after V2 (day 71), and after V3 (day 86) are shown.

Figure 21:
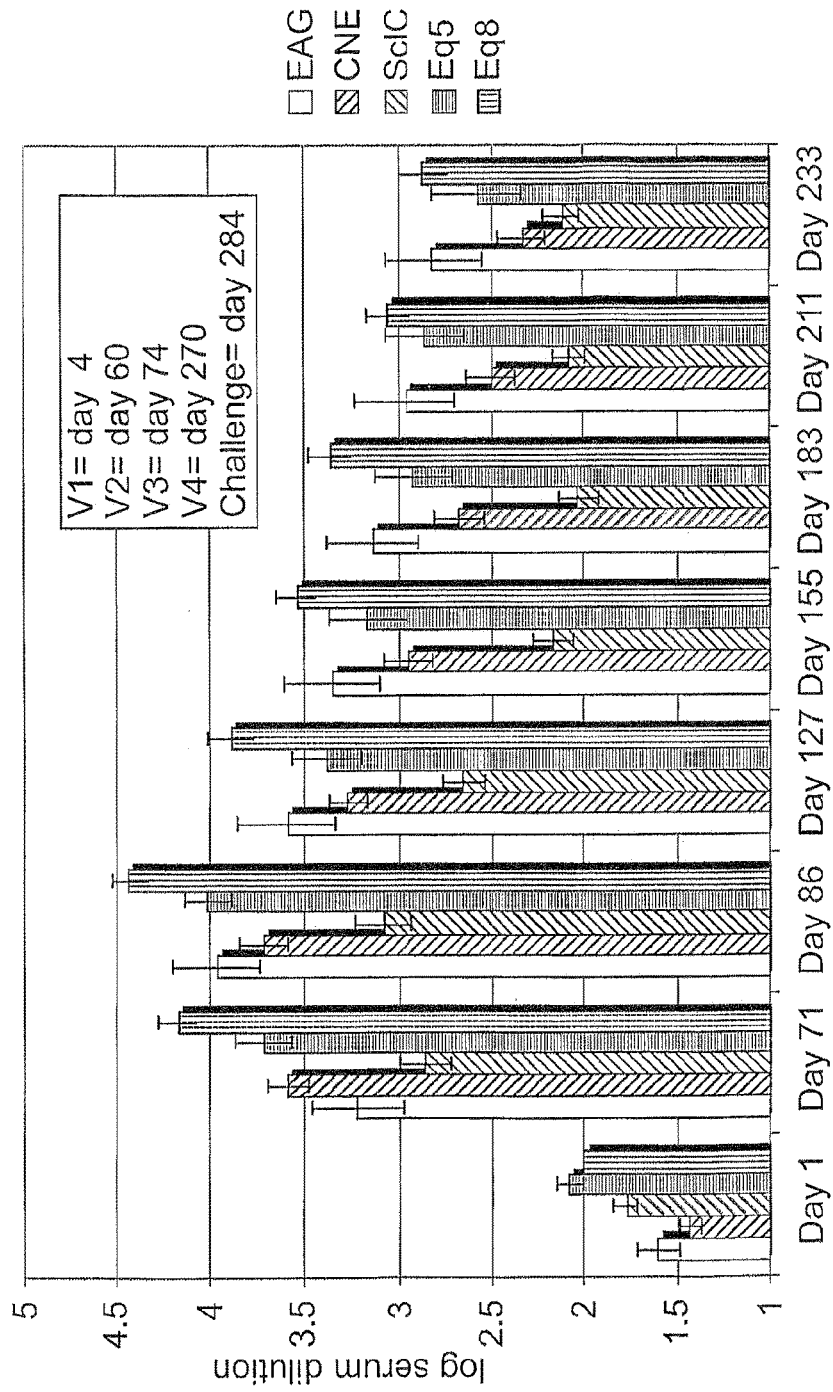

FIG. 21 shows ELISA measurements of IgG antibodies in sera of immunized horses (Pentavac). The log dilution of sera required to give an absorbance value at a cut-off of 1.5 was calculated for each individual serum sample. Mean values (n=7) with standard errors are shown. Sample taken before (day 1), after V2 (day 71), and after V3 (day 86) and samples taken between V3 and V4 (day 270) are shown.

BRIEF DESCRIPTION OF THE SEQUENCE LISTING

SEQ ID NO 1 shows the amino acid sequence of the protein IdeE2.

SEQ ID NO 2 shows the amino acid sequence of the recombinant protein IdeE2.

SEQ ID NO 3 shows the amino acid sequence of the protein Eq5.

SEQ ID NO 4 shows the amino acid sequence of the recombinant protein Eq5.

SEQ ID NO 5 shows the amino acid sequence of the protein Eq8.

SEQ ID NO 6 shows the amino acid sequence of the recombinant protein Eq8.

SEQ ID NO 7 shows the amino acid sequence of the protein IdeZ2 from subsp, *zooepidemicus*.

SEQ ID NO 8 shows the amino acid sequence of the protein Eqz5 from subsp. *zooepidemicus*.

SEQ ID NO 9 shows the amino acid sequence of the protein Eqz8 from subsp. *zooepidemicus*.

SEQ ID NO 10 shows the amino acid sequence of the protein IdeE.

SEQ ID NO 11 shows the amino acid sequence of the protein IdeZ from subsp. *zooepidemicus*.

SEQ ID NOS 12 and 13 shows, respectively, the nucleotide sequence of the gene eag and the amino acid sequence of the protein EAG4B, which protein is usually designated EAG in connection with the present invention.

SEQ ID NO 14 shows the nucleotide sequence of the gene ideE2.

SEQ ID NO 15 shows the nucleotide sequence of the gene eq5.

SEQ ID NO 16 shows the nucleotide sequence of the gene eq8.

SEQ ID NO 17 shows the nucleotide sequence of the gene IdeZ2 from subsp. *zooepidemicus*.

SEQ ID NO 18 shows the nucleotide sequence of the gene eqz5 from subsp. *zooepidemicus*.

SEQ ID NO 19 shows the nucleotide sequence of the gene eqz8 from subsp. *zooepidemicus*.

SEQ ID NO 20 shows the nucleotide sequence of the gene ideE.

SEQ ID NO 21 shows the nucleotide sequence of the gene ideZ from subsp. *zooepidemicus*.

SEQ ID NOS 22.27 show nucleotide sequences of oligonucleotide primers.

SEQ ID NO 28 shows the amino acid sequence of the protein CNE (or SEC 2.16).

SEQ ID NO 29 shows the amino acid sequence of the protein SclC.

SEQ ID NO 30 shows the amino acid sequence of the recombinant IdeE used for immunization.

SEQ ID NO 31.32 shows the nucleotide sequence of primers.

DETAILED DESCRIPTION OF THE INVENTION

The present invention is concerned with identification of polypeptides or proteins of *S. equi* that are able to elicit an antigenic, suitably an immunogenic, response, when administered to a non-human mammal; and to the identification of polynucleotides or genes encoding these polypeptides or proteins.

The present invention is also concerned with fragments or analogs of said polypeptides or proteins or of said polynucleotides or genes.

More specifically, genes of *S. equi* encoding extracellular proteins were identified and, subsequently, the corresponding products were expressed and evaluated in vaccine studies. The present invention is at least partly based on such studies.

Accordingly, the present invention relates to an antigenic composition comprising at least one antigen, wherein said at least one antigen comprises at least part of a protein of *Streptococcus equi* subsp. *equi* or subsp. *zooepidemicus*, and said at least part of said protein comprises at least one antigenic epitope or antigenic determinant of *Streptococcus equi*.

According to one embodiment, the present invention is directed to an antigenic composition comprising at least one antigen, wherein said at least one antigen comprises at least part of a protein or polypeptide of *Streptococcus equi* subsp. *equi* or subsp. *zooepidemicus* and said at least part of said protein or polypeptide comprises at least one antigenic epitope or antigenic determinant of *Streptococcus equi*, and wherein said protein or polypeptide is selected from the group comprising:

a protein or polypeptide which is designated EAG and has an amino acid sequence as shown in SEQ ID NO: 13;

a protein or polypeptide which is designated IdeE and has an amino acid sequence as shown in SEQ ID NO: 10;

a protein or polypeptide which is designated IdeE2 and has an amino acid sequence as shown in SEQ ID NO: 1;

a protein or polypeptide which is designated Eq5 and has an amino acid sequence as shown in SEQ ID NO: 3;

a protein or polypeptide which is designated Eq8 and has an amino acid sequence as shown in SEQ ID NO: 5;

a protein or polypeptide which is designated IdeZ2 and has an amino acid sequence as shown in SEQ ID NO: 7;

a protein or polypeptide which is designated Eqz5 and has an amino acid sequence as shown in SEQ ID NO: 8; and a protein or polypeptide which is designated Eqz8 and has an amino acid sequence as shown in SEQ ID NO: 9;

or an analog or a fragment thereof, and wherein a composition which comprises EAG, comprises at least one further antigen, which is a protein or polypeptide, which is selected from the group comprising IdeE, IdeE2, Eq5, Eq8, IdeZ2, Eqz5, and Eqz8.

For convenience, the polypeptides having amino acid sequences as shown in the sequence listing are frequently only designated EAG, IdeE, IdeE2, Eq5, Eq8, IdeZ2, Eqz5, and Eqz8, respectively. EAG, IdeE, IdeE2, Eq5, and Eq8 designate proteins that can be found in *S. equi* subsp. *equi* and IdeZ, IdeZ2, Eqz5, and Eqz8 designate proteins that can be found in *S. equi* subsp. *zooepidemicus*.

The antigens or immunogens of the present antigenic or immunogenic compositions may comprise the entire amino acid sequence of said protein or polypeptide or may comprise a fragment, e.g. a C-terminal or N-terminal fragment thereof, or an analog thereof. For instance, an N-terminal fragment of EAG is used according to various embodiments of the present invention.

According to one embodiment, the present invention is related to an antigenic or immunogenic composition which contains at least 2 or 3 antigens or immunogens selected from the group consisting of EAG, IdeE, IdeE2, Eq5, Eq8, IdeZ, IdeZ2, Eqz5, and Eqz8.

According to a specific embodiment, the present invention is related to an antigenic or immunogenic composition which contains at least 2 or 3 antigens or immunogens selected from the group consisting of EAG, IdeE, IdeE2, Eq5, and Eq8. Suitably this composition also comprises one or both of the previously described antigens SclC (SEQ ID NO: 33) and CNE (SEQ ID NO: 28) (also designated SEC e.g. SEC 2.16). A further embodiment is related to an antigenic composition comprising EAG, SclC, CNE, Eq5, and Eq8.

A suitable composition contains 2 antigens or immunogens which are comprised of Eq5 and Eq8, respectively. According to a further embodiment, the present invention is directed to a composition that contains 3 antigens or immunogens, which suitably are comprised of EAG, IdeE, and IdeE2. The present invention is also related to compositions that comprise one or both of IdeE and IdeE2.

The present invention is also related to an antigenic composition, wherein said at least one protein or polypeptide is selected from the group consisting of EAG, Eq5 and Eq8 and which composition further comprises at least one antigen, which is selected from the group comprising a protein or a polypeptide designated ONE (or SEC), which has an amino acid sequence as shown in SEQ ID NO: 28, and a protein or a polypeptide designated SclC, which has an amino acid sequence as shown in SEQ ID NO: 33. Suitably, said at least one protein or polypeptide is selected from the group comprising IdeE and IdeE2.

Antigenic compositions of the present invention, which have been shown to be useful in vaccine compositions, comprise according to one embodiment, the antigens EAG, SclC, CNE (or SEC), Eq5, Eq8, IdeE and IdeE2, and according to another embodiment, the antigens EAG, SclC, CNE (or SEC), Eq5, and Eq8.

The present invention is also related to an antigenic composition, wherein said at least one protein or polypeptide is selected from the group consisting of EAG, Eq8, and IdeE2 and which composition comprises at least one further antigen which is selected from the group comprising IdeE, Eq5, ideZ2, Eqz5 and Eqz8 and/or SclC and CNE (or SEC).

According to the present invention, the antigenic composition suitably comprises at least one antigen which is recombinantly produced and/or at least one antigen which is an isolated or purified antigen.

From the above, it is evident that the present antigens or immunogens that are derived from proteins of *Streptococcus equi* may comprise the entire protein, a fragment of said protein or an analog of said protein which is antigenic or immunogenic. Thus, the present invention is not limited to the fragments of proteins that are specifically disclosed herein.

The antigenic composition of the present invention may comprise at least one recombinant vector and at least one polynucleotide inserted therein that encodes said at least one protein or polypeptide, and which vector is able to express said polypeptide in vivo in a non-human mammal susceptible to infection with *S. equi*.

According to one embodiment of the present invention, the vector is an expression vector which is a plasmid or a viral vector and wherein said polynucleotide has a nucleotide sequence that encodes an antigen of the present invention.

A further embodiment of the present invention is concerned with a vaccine composition for protecting non-human mammals against infection of *Streptococcus equi*, which comprises an antigenic composition as disclosed above as immunizing component, and a pharmaceutically acceptable carrier.

Suitably, the present vaccine composition comprises an antigenic or immunogenic composition that contains 2, 3 or more of the present antigens or immunogens as immunizing components. Optionally, one or more of these antigens or immunogens are comprised of analogs of said proteins or fragments thereof, e.g. N-terminal or C-terminal fragments.

The vaccine composition may comprise further components, such as an adjuvant. Suitably, said adjuvant stimulates systemic or mucosal immunity. Such adjuvants are well known in the art.

Suitable adjuvants for use according to the present invention comprise (1) polymers of acrylic or methacrylic acid, maleic anhydride and alkenyl derivative polymers, (2) immunostimulating sequences (ISS), (3) an oil in water emulsion, (4) cation lipids containing a quaternary ammonium salt, (5) cytokines, (6) aluminum hydroxide or aluminum phosphate, (7) saponin or (8) nanoparticles.

A suitable adjuvant for use according to the present invention is the adjuvant Abisco from Isconova AB, Sweden. The key components of ISCOMS are *Quillaia* saponins derived from the bark of the Chilean soap bark tree *Quillaia saporinaria molina*. *Quillaia* saponins are well known for their ability to activate the immune system. *Quillaia* saponins mixed with cholesterol, and phospholipids under specific stoichiometry form spherical open cage like structures known as ISCOMS.

Another suitable adjuvant is *Ginseng*. *Ginseng* is a dry extract prepared from the root of the plant *Panax ginseng*, C. A. Meyer. *Ginseng* contains a number of active substances named ginsenosides that are a kind of saponins, chemically tri-terpenoid glycosides of the dammaran series. The ginsenosides have adjuvant properties and one of the most active adjuvant is the fraction named Rb1. It has been proved that the fraction Rb1 elicits a balanced Th1 and Th2 immune response as determined by measuring the levels of the cytokines IFN-$\gamma$, IL-2, IL-4, IL-10 secreted post vaccination with a Rb1 adjuvanted vaccine. In addition *ginseng* and the fraction Rb1 stimulates a strong antigen specific antibody response.

According to a suitable embodiment, the vaccine composition is a vaccine that protects susceptible mammals, suitably horses, against strangles caused by *Streptococcus equi* subsp. *equi*.

The vaccine composition of the present invention is provided in a physiologically administrable form. Suitably, it is administrable by subcutaneous, intramuscular or intranasal inoculation.

Suitably, the vaccine composition of the present invention stimulates serum, mucosal and/or bronchial lavage antibody responses directed to *Streptococcus equi* antigens in mammals susceptible to *Streptococcus equi*, suitably horses.

The present invention is also related to a method for producing an antigen or immunogen to be used in an antigenic or immunogenic composition of the present invention, which method comprises
(a) providing a DNA fragment encoding said antigen and introducing said fragment into an expression vector;
(b) introducing said vector, which contains said DNA fragment, into a compatible host cell;
(c) culturing said host cell provided in step (b) under conditions required for expression of the product encoded by said DNA fragment; and
(d) isolating the expressed product from the cultured host cell.

Preferably, said method further comprises a step (e) wherein the isolated product from step (d) is purified, e.g. by affinity chromatography or other chromatographic methods known in the art.

Accordingly, the antigens of the present invention are usually produced according to recombinant technique.

A further embodiment of the present invention is concerned with a method for preparation of a vaccine of the present invention, which vaccine contains as immunizing component an antigenic or immunogenic composition as disclosed above, said method comprising mixing said antigenic composition and a pharmaceutically acceptable carrier.

The present invention is also related to a method for the production of an antiserum, said method comprising administering an antigenic preparation of the present invention to an animal host to produce antibodies in said animal host and recovering antiserum containing said antibodies produced in said animal host.

Moreover, the present invention is concerned with a method of prophylactic or therapeutic treatment of *S. equi* infection in non-human mammals, suitably horses, comprising administering to said mammal an immunologically effective amount of a vaccine or an antiserum of the present invention.

Accordingly, the present invention is related to a method for protecting horses against *Streptococcus equi* infection, which method comprises inoculating a horse intramuscular, subcutaneously or intranasally, or a combination of e.g. both subcutaneously and intranasally, with a vaccine composition of the present invention to induce an immune response against *Streptococcus equi* in said horse. Suitably, an immune response, in the form of IgG and/or IgA and/or IgM antibodies in the nasopharyngeal mucus, is induced in said horse.

The present invention also relates to an antibody preparation comprising at least one, and suitably at least two, antibodies specific for a protein or a polypeptide of the present antigenic composition, which antibody/antibodies is/are polyclonal or monoclonal; or which preparation comprises a fragment of said antibodies.

The antibody preparation of the present invention could be used prophylactically or therapeutically against strangles and provides passive immunization when administered to a non-human mammal susceptible to infection by *Streptococcus equi* or infected by *Streptococcus equi*.

The present invention describes a vaccine composition comprising one or several antigen components which have been prepared according to the present method using *E. coli* as host cells. The source of these antigens might also be the native bacteria, if methods are developed for expression and purification thereof. Alternatively, the antigens of the present invention can also be produced according to methods that are based on fusion strategies where various parts of the respective antigen are recombined resulting in a fusion can in protein consisting of parts from different antigens. This fusion strategy could also be suitable for introducing immune reactive part(s), e.g. T-cell epitopes or attenuated toxins (or parts thereof), thereby introducing other features suitable for optimizing the antigen presentation or localization. Furthermore, other hosts for expressing the recombinant antigens addition to *E. coli* also be other suitable species of bacteria and viruses. Today many different systems for expression of heterologus expression are well known in the field of molecular biology.

Yet another implication of this invention is that it can be used to design specific attenuated mutants of *S. equi* that lack or have inactivated genes important for survival (i.e. mutations causing deficiency in metabolic pathways) in the host but retain or overproduce the antigens of the present invention.

EXPERIMENTAL PART

The DNA sequence of the genome of *S. equi* subsp. *equi* and subsp, *zooepidemicus* have been determined but not yet annotated. By screening open reading frames a great number of genes encoding extracellular proteins were identified. Among these genes a selected number were chosen and recombinant proteins were produced and evaluated in vaccine studies. The cloning and expression of these genes is described below. Furthermore, the use of these proteins as antigens will also be described.

Example 1. Constructions of Clones Harboring the Genes ideE, ideE2, Eq5 and Eq8 from Subsp. *equi*

Chromosomal DNA from *S. equi* subspecies *equi* strain 1866 (PCT/SE03/01587, Lannergard and Guss 2007) was used as a template to amplify potential genes encoding IdeE2, Eq5 and Eq8 (the nucleotide- and protein-sequences are presented in the sequence listing further below). To identify the predicted signal sequences, the computer program SignalP was used. The sequences of primers used to amplify the genes or part of the genes ideE, ideE2, eq5 and eq8 are listed in the Primer Table. Cleavage sites for the restriction enzymes NcoI and XhoI were included in the primer sequences to match the cloning sites in the plasmid vector pTYB4 (New England Biolabs). The PCR amplifications were performed using the primers (20 pmol/µl) and the ReadyToGo™ PCR beads (GE Healthcare) using the following programme: Step 1, pre-heat 1 minute at 95° C.; DNA strand separation; Step 2, 30 seconds at 95° C.; Step 3, annealing 15 seconds at 46° C.; and Step 4, elongation for 2 minutes at 72° C., Steps 2-4 were run for 26 cycles. The PCR products were analysed on a 1% agarose gel, and thereafter purified. Cleavage with the restriction enzymes was performed over night whereupon the fragments were purified one additional time using the same kit.

To clone and produce recombinant proteins in *E. coli* the Protein Purification System (New England Biolabs) was used. *E. coli* strain ER2566 containing the pTYB4 vector (New England Biolabs) was grown according to the manufacturer's instructions, and the vector was purified using the QIAprep Spin Miniprep (Qiagen). Purified vector was digested using restriction endonucleases NcoI and XhoI. After digestion, the vector was treated with the enzyme alkaline phosphatase to reduce the background of re-ligated vector in the later ligation step. For the ligation of the vector and the respective PCR product, the ReadyToGo T4DNA Ligase (GE Healthcare) was used. After ligation, the respective sample were transformed into competent cells of *E. coli* strain ER2566 using electroporation, and spread on LA-Amp plates (Luria-Bertani broth agar plates supplemented with ampicillin, final conc. 50 µg/ml) and incubated over night at 37° C. Next day colonies were counted and four colonies per construct were cultivated and used for further experiments. To verify the presence of an insert in the respective constructs, plasmids were purified and additional PCR analyses were performed using the respective primer combination. The sequence of the respective insert was also determined by DNA sequencing using primers that hybridise in the vector (T7 universal forward primer and a reverse primer located in the intein coding region).

Cloning of the ideE gene of *S. equi* subsp, *equi* strain 1866 has been reported previously by Lannergård and Guss (2006). The GenBank accession number of ideE is DQ508733. The part of the gene used to obtain the recombinant IdeE protein used for immunization was cloned using the primers IdEG1 and IdEG2 listed in the Primer Table. After PCR amplification the DNA fragment was digested with restriction enzymes RamHI and XhoI and ligated into the vector pGEX6-P-1 (GE Healthcare), previously digested with the same enzymes.

Primer Table:
The primer sequences used to PCR amplify the genes ideE, ideE2, eq5 and eq8. The nucleotides underlined correspond to the introduced restriction cleavage sites NcoI and XhoI.

| Gene | Primer | Primer sequence |
| --- | --- | --- |
| ideE2 | Forward primer | 5'-CATGCCATGGAGGTAGTTGAAGTTTGGCCTAAT-3' (SEQ ID NO: 22) |
| ideE2 | Reverse primer | 5'-CCGCTCGAGTTTTTCTGTCTTGTTGAAGTAATCTGC-3' (SEQ ID NO: 23) |
| eq5 | Forward primer Eqp51: | 5'-GTAGCCATGGAAACGACTACTGCTAGTGCA-3' (SEQ ID NO: 24) |
| eq5 | Reverse primer Eqp52: | 5'CTGGCTCGAGCGGTTTAGCAACCAAGGCT-3' (SEQ ID NO: 25) |
| eq8 | Forward primer Eqp81: | 5'CATGCCATGGCGACTACCCTAGCAGGACAAA-3' (SEQ ID NO: 26) |
| eq8 | Reverse primer Eqp82: | 5'CTAGCTCGAGGTGCTTAAGCTTTTCAATCTG-3' (SEQ ID NO: 27) |
| ideE | Forward primer IdEG1: | 5'-TACTGGATCCGACGATTACCAAAGGAATGCTAC-3' (SEQ ID NO: 31) |
| ideE | Reverse primer IdEG2: | TGATCTCGAGTTAGCTCAGTTTCTGCCATATG (SEQ ID NO: 32) |

Example 2. Preparation of Antigens CNE, SclC, EAG4B, IdeE, IdeE2, Eq5 and Eq8

The vector used is a part of an *E. coli* expression and purification system called T7 (NEB Inc.) Briefly, following the manufacturer's instructions the clones expressing recombinant IdeE2, Eq5 and Eq8, respectively were grown at 37° C. in Luria Bertani growth medium supplemented with ampicillin (final conc. 50 µg/ml). At an optical density $(OD_{600})$~0.6, the growth medium was supplemented with IPTG (final conc. 0.4 mM) and the growth temperature shifted to 20° C. After incubation over night the cells were harvested and resuspended in a buffer [20 mM Tris-HCl (pH 8.0), 500 mM NaCl, 0.1 mM EDTA, and 0.1% Triton X100]

and lysed by freezing and thawing. After centrifugation, the supernatant was sterile filtrated and applied onto a chitin column. The columns were extensively washed using the same buffer and subsequently treated with cleavage buffer [20 mM Tris-HCl (pH 8.0), 50 mM NaCl, 0.1 mM EDTA, and 30 mM dithiothreitol (DTT)]. In the cleavage buffer, the reducing conditions induce an intein-mediated self-cleavage that releases the antigen part from the column while the intein-chitin-binding part is still bound. The eluted samples containing the antigens were dialysed against phosphate-buffered saline [PBS; 137 mM NaCl, 2.7 mM KCl, 10 mM $Na_2HPO_4$, 1.4 mM $KH_2PO_4$ (pH 7.4)] and concentrated. The amounts of antigens obtained were determined and the quality was checked using SDS-PAGE. The recombinant IdE protein was produced and purified using the GST-affinity chromatography system according to the procedure recommended by the manufacturer (GE Healthcare). The description of and production of the recombinant proteins CNE(SEC), SclC, and EAG4B antigens have been described previously (WO 2004/032957 (PCT/SE03/01587), Waller et al 2007). In the following examples, the EAG4B protein is simply called EAG.

Example 3. Recombinant IdE2 Cleaves IgG

IdE has previously been shown to be a protease that specifically cleaves IgG from various species (Lannegård and Guss 2006). To test if recombinant IdeE2 also cleaves antibodies, IgG from human, horse and mouse were incubated in PBS at 37° C. for one hour. Purified recombinant IdeE was used as a positive control and the negative control was pure IgG. After cleavage, the samples were analysed using 8-25% gradient SDS-PAGE. The result showed that recombinant IdeE2 cleaves horse IgG much more efficiently than IdeE does.

Example 4. Presence of the Genes ideE, ideE2, Eq5, and Eq8 in *S. equi* Subsp. *zooepidemicus*

Previously the presence of a homologous subsp. *equi* ideE gene in subsp. *zooepidemicus* has been reported (Lannegard and Guss 2006). Using the *S. zooepidemicus* genome database, the presence of similar genes to ideE2, eq5 and eq8 in subspecies *zooepidemicus* was analysed using BLAST search. The results showed that genes encoding similar proteins were detected. The sequence of these genes called ideZ2, eqz5 and eqz8 along with amino acid sequences IdeZ2, Eqz5 and Eqz8 are shown in the list of sequences in the experimental part of this specification.

Example 5. Immunisation of Mice with Eq5 and Eq8

Mice (NMRI) weighting approximately 23-25 g were kept in cages of five animals in each. The mice were immunised intranasally with 12 micrograms of each antigen and 10 microgram of Abisco 300 (Isconova AB, Sweden). Fifteen animals were immunised with antigen (Eq5 and Eq8) and 15 were only given Abisco 300 adjuvant to serve as a negative control. The total volume was kept to less than 27 µl and applied into the nostrils twice with 30 minutes interval of mice anaesthetized with Isoflovet (Abbot Laboratories, England). Immunisations were given on days 0, 13 and 32.

Example 6. Immunisation of Mice with EAG, IdeE and IdeE2

Immunisation with EAG, IdeE and IdeE2 was performed essentially as for Eq5 and Eq8. However, animals were divided into three groups, with ten mice in each group. These were given EAG+IdeE+IdeE2 or EAG only and one group with only adjuvans, Abisco 300, as negative control. Immunisations were given on days 0, 21 and 53. Experimental infection was given on day 60.

Example 7. Experimental Infection with *Streptococcus equi* Subsp. *Equi*

Experimental infection was given on day 43 (10 days after last time of immunisation) for Eq5+Eq8 and on day 60 (10 days after last immunisation) for EAG+/−IdeE+IdeE2, *S. equi* subsp. *equi* strain 1866 from a clinical case of strangles was used. The strain was first passed through an animal by inoculating ca $10^6$ CFU into the nostrils of an anaesthetized mouse. Bacteria were recovered after 7 days from the nose of the mouse and grown on BG plates at 37° C. in 5% $CO_2$. A single colony was grown on BG plates overnight at 37° C. and resuspended in Todd Hewitt Broth (THB) with 1% yeast extract (THY). The culture was kept at −80° C. in vials and a new vial was used for each experiment. To infect mice, bacteria were grown on BG plates at 37° C. in 5% $CO_2$ overnight, followed by inoculation into THY and grown without shaking over night. The cultures was then diluted 10 times into THY and 10% horse serum (Sigma) and grown for 4 hours at 37° C. in 5% $CO_2$. The culture was centrifuged and resuspended in THB. A dose containing $1\times10^6$ CFU in 10 µl was used for all *S. equi* infections of mice. The animals were followed daily. Bacterial nasal growth was scored on a four-graded scale from 0 to +++ by gently pressing the nose of the animal onto a blood agar plate in a reproducible manner. The nasal sample was then spread out onto the entire surface of the plate. One + means 5-100 colonies; two + means more than 100 and three + means confluent growth. The weight was determined every day and the percentage of weight-loss was calculated.

Example 8. Experimental Results of Vaccination

Figure 1:
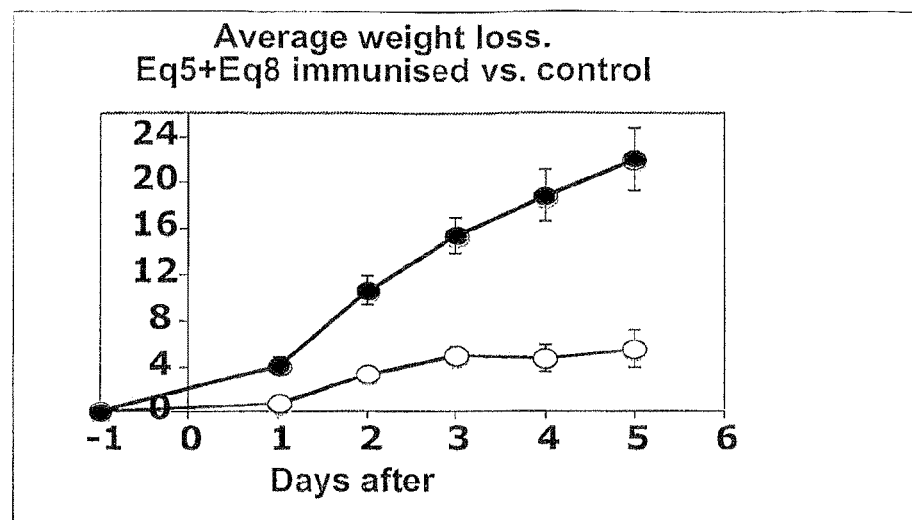
FIG. 1 shows weight loss of mice given experimental infection with *S. equi* subsp. *equi* strain 1866 after vaccination with the polypeptides Eq5 and Eq8 (open symbols) or non-vaccinated (filled symbols)
Figure 2:
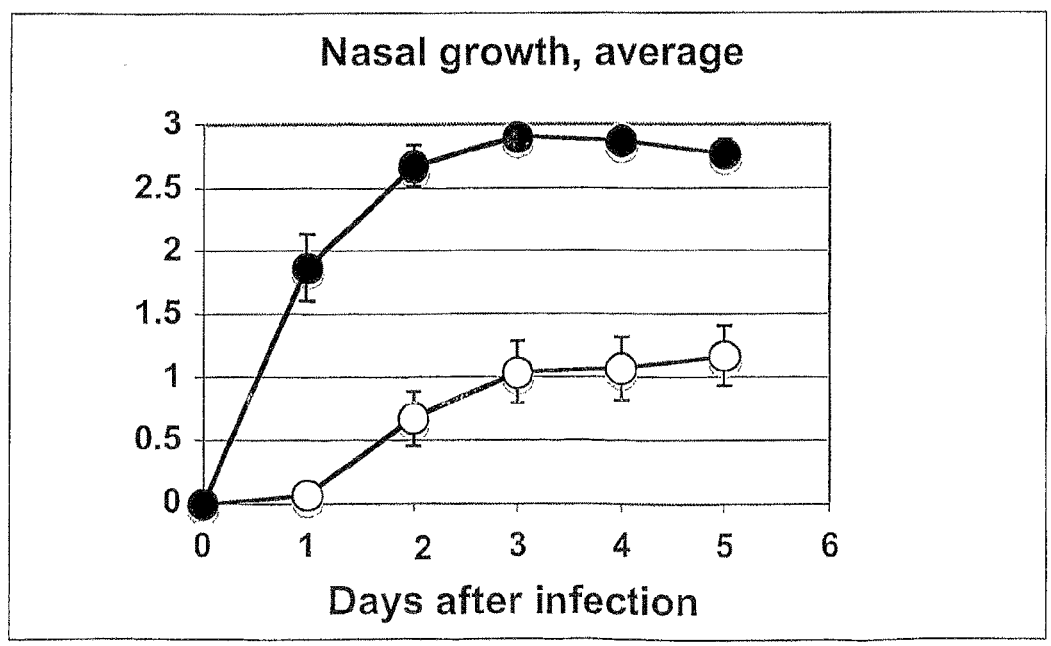
FIG. 2 shows nasal growth in mice given experimental infection with *S. equi* subsp. *equi* strain 1866 after vaccination with the polypeptides Eq5 and Eq8 (open symbols) or non-vaccinated (filled symbols)

Mice were immunised with both Eq5 and Eq8 and the percentage weight loss over time was determined. FIG. 1 shows that vaccinated animals (n=15) lost less weight that control animals (n=15). P-values=0.0001 for all days (Student's t-test). Nasal growth of *S. equi* was also determined daily on a four graded scale. FIG. 2 shows that the vaccinated animals had much less nasal growth than the control group. The frequency of animals grossly colonised nasally with bacteria (scoring 2-3) on day 5 was significantly different between the two groups; p=0.002 (Fisher's exact test).

Figure 3:
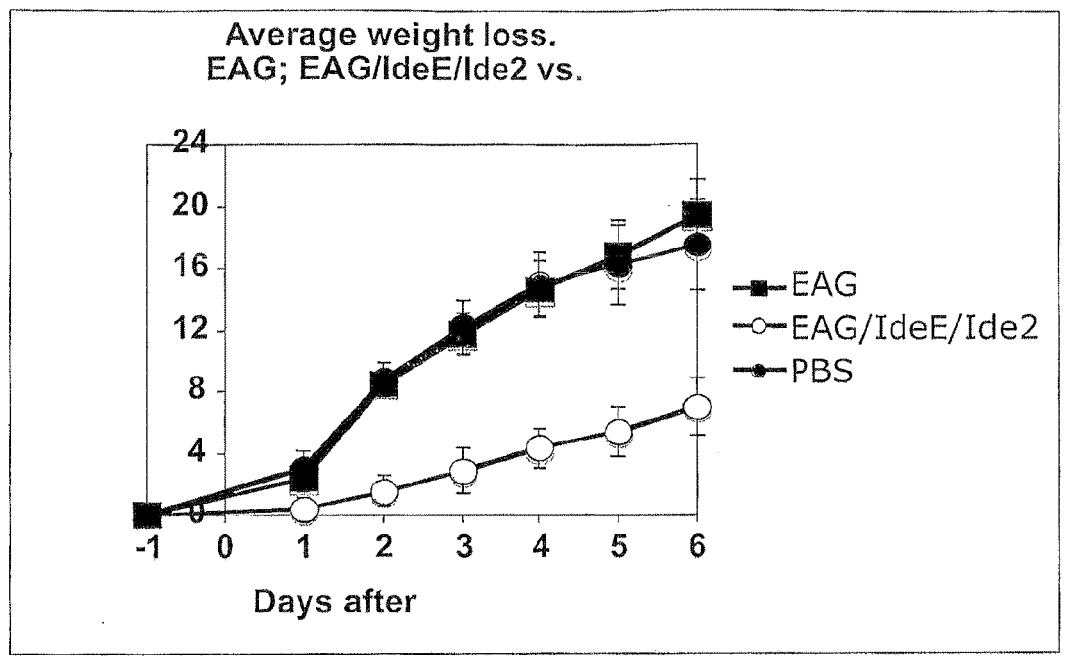
FIG. 3 shows weight loss of mice given experimental infection with *S. equi* subsp. *equi* strain 1866 after vaccination with the polypeptide EAG (filled squares), the polypeptides EAG-HdeE+IdeE2 (open circles) or non-vaccinated controls (filled circles)
Figure 4:
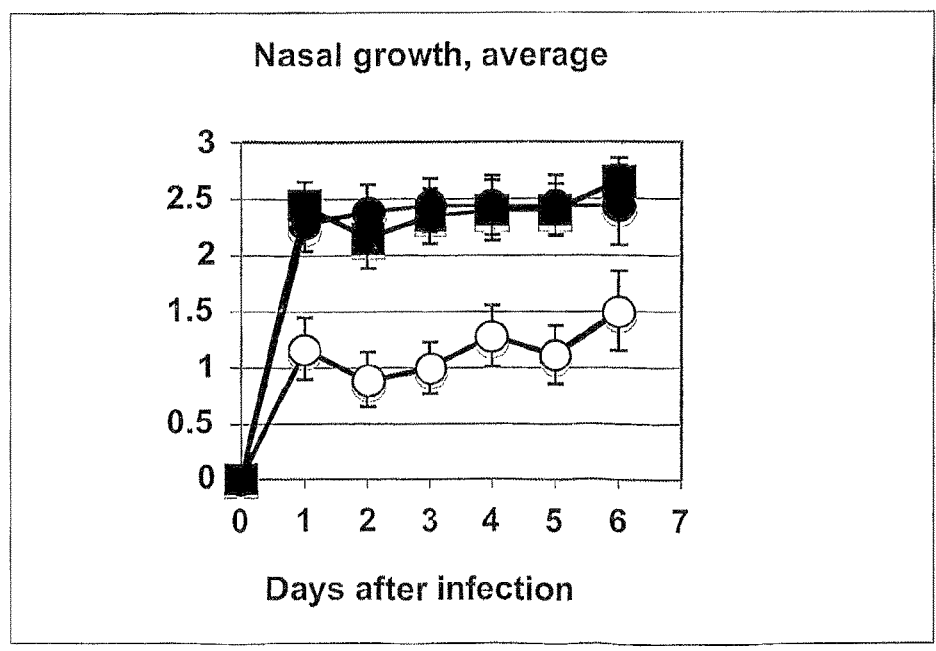
FIG. 4 shows nasal growth in mice given experimental infection with *S. equi* subsp. *equi* strain 1866 after vaccination with the polypeptide EAG (filled squares), the polypeptides EAG+IdeE+IdeE2 (open circles) or non-vaccinated controls (filled circles).

In the next experiment; mice were vaccinated with EAG (n=10), with EAG+IdeE+IdeE2 (n=10) or non-vaccinated (n=10). The percentage weight loss over time was determined. FIG. 3 shows that animals vaccinated with EAG+ IdeE+IdeE2 lost less weight that control animals. P values were 0.0013, 0.0008 and 0.0009 for days 3, 5 and 6 respectively (Student's t-test). Animals vaccinated with EAG alone also lost weight to a similar magnitude as control animals. Nasal growth of *S. equi* was also determined daily on a four graded scale. FIG. 4 shows that the animals vaccinated with EAG+IdeE+IdeE2 had much less nasal growth than the control group. Again, vaccination with only EAG showed no protection.

Example 9. Immunisation of Mice with Eq5, Eq8, and EAG, CNE, SclC

Figure 5A:
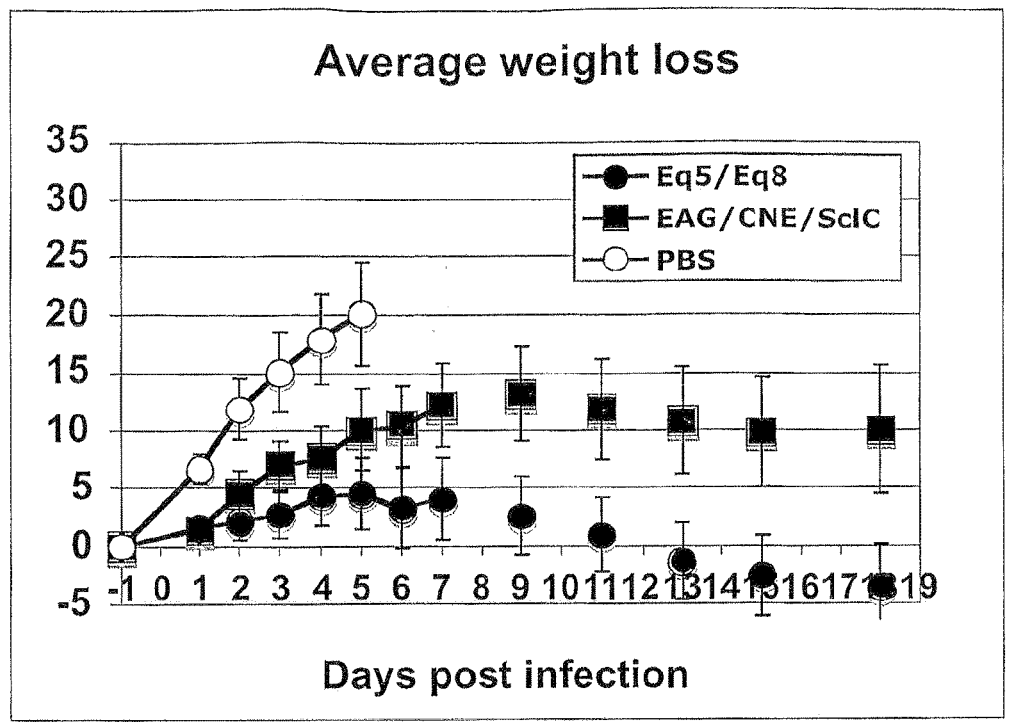
FIGS. 5*a* and 5*b* show weight loss and nasal growth in mice immunized with EAG+CNE+SclC i.n. (filled squares), Eq5+Eq8 i.n. (filled circles) and the control (open circles).
Figure 5B:
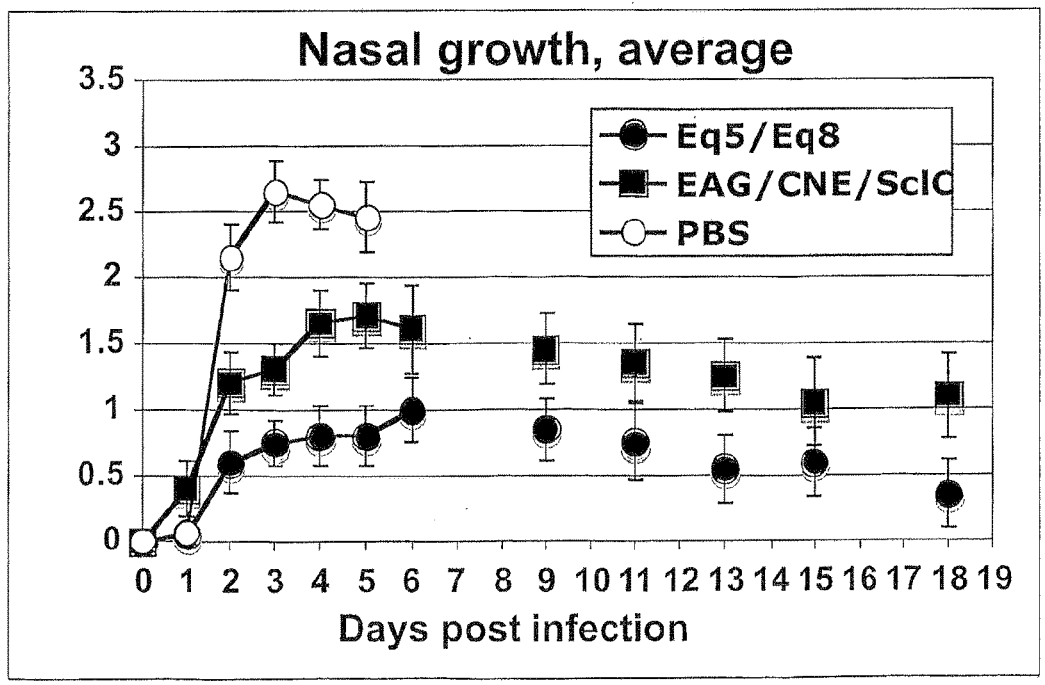

Immunisation i.n. with Eq5+Eq8 and EAG+CNE+SclC was performed as above with three groups with ten mice in each group. One group with Eq5+Eq8 and one with EAG+CNE+SclC. The third group was the control with Abisco-300. Immunisations were given on days 0, 14 and 22. Challenge was given on day 29. The experimental results are shown in FIG. 5a and FIG. 5b. FIGS. 5a and b show significant protection for EAG+CNE+SclC (n=10). P-values were 0.04 and 0.09 for day 2 and 5. The protection with Eq5+Eq8 was even more pronounced where p-values were 0.005 and 0.009 for these days.

---

LIST OF SEQUENCES (1) SEQ ID NO: 1 and SEQ ID NO: 14 are combined to show the amino acid sequence of the IdeE2 protein (SEQ ID NO: 1) under the nucleotide sequence of ideE2 (SEQ ID NO: 14)

```
atgatgaaaaaacaa
 M  M  K  K  Q tcattcacacactcacgtaaacctaaattcggtatgagaaaattatctattggccttgcc
 S  F  T  H  S  R  K  P  K  F  G  M  R  K  L  S  I  G  L  A tcatgtatgctaggaatgatgttcctaacaacaggacatgtttctggtgaggtagttgaa
 S  C  M  L  G  M  M  F  L  T  T  G  H  V  S  G  E  V  V  E gtttggcctaatgggcaaaatcctaatggtaaaatagaaattctaagtcaaactgagcac
 V  W  P  N  G  Q  N  P  N  G  K  I  E  I  L  S  Q  T  E  H tctgagcatttacagaaattacgcgatattgaagatttccaagctcaaaagcaagctgat
 S  E  H  L  Q  K  L  R  D  I  E  D  F  Q  A  Q  K  Q  A  D catgttcgttacactaaatggttagatggggtaactgttgatgagcatgaattcagaaaa
 H  V  R  Y  T  K  W  L  D  G  V  T  V  D  E  H  E  F  R  K atcaaggaatatgacacagaatattatgtaacacctcttttaagtggtaaaggttactat
 I  K  E  Y  D  T  E  Y  Y  V  T  P  L  L  S  G  K  G  Y  Y gatatcaataaagatttcaatcaagatagtgataaatgtgctgccgctgtagcggctaat
 D  I  N  K  D  F  N  Q  D  S  D  K  C  A  A  A  V  A  A  N atgttccattattggtttgatagaaatagagacagtattaatcgtttcttaagtcaaagt
 M  F  H  Y  W  F  D  R  N  R  D  S  I  N  R  F  L  S  Q  S ccaggtgaaaatggtgttattaaacttgaaaatgaaaaaacaatagaagtatcaaaattt
 P  G  E  N  G  V  I  K  L  E  N  E  K  T  I  E  V  S  K  F ttagaaacttaccgtagtgatggtgattatcttgataaaagtccgttttttgaccttatc
 L  E  T  Y  R  S  D  G  D  Y  L  D  K  S  P  F  F  D  L  I agtaacagctttaaaggtcctgtttgggcaaataagctattggatgcttacattaacggc
 S  N  S  F  K  G  P  V  W  A  N  K  L  L  D  A  Y  I  N  G tatggttatatccataaatttgctaaaaatactccacattctaaaaataataatagtaaa
 Y  G  Y  I  H  K  F  A  K  N  T  P  H  S  K  N  N  N  S  K tttaatttctttaaaaaagtatttgatggtaatctcttgacagatattcaccaaatttt
 F  N  F  F  K  K  V  F  D  G  N  L  L  T  D  I  H  Q  I  F gattataacacttttcagataaattaagtgaggctctctatactggtaaagccattgga
 D  Y  N  T  F  S  D  K  L  S  E  A  L  Y  T  G  K  A  I  G ttggcctacggacctggagacttgcgtcgttcactaggtcatattatttctgtctgggga
 L  A  Y  G  P  G  D  L  R  R  S  L  G  H  I  I  S  V  W  G gctgatcttgacgatcagaatcgcgtggtagctatttatataactgattctgatgataaa
 A  D  L  D  D  Q  N  R  V  V  A  I  Y  V  T  D  S  D  D  K aagttaactataggaaatgagagagttggtttgaagcgatataaagtatctagcgatgat
 K  L  T  I  G  N  E  R  V  G  L  K  R  Y  K  V  S  S  D  D
```

```
caaggtcgtgctcgtctgacgactcgtgataaagataacacaggtggtgaaattcgatct
  Q  G  R  A  R  L  T  T  R  D  K  D  N  T  G  G  E  I  R  S attgaaacattagatatgggtacacaagagtgggcagattacttcaacaagacagaaaaa
  I  E  T  L  D  M  G  T  Q  E  W  A  D  Y  F  N  K  T  E  K taa
  -
```

(2) SEQ ID NO: 2 shows the recombinant IdeE2 protein sequence. The amino acids in bold are those that corresponds to the amino acids encoded by the pTYB4 vector while the rest originates from the IdeE2 protein.

MEVVEVWPNGQNPNGKIEILSQTEHSEHLQKLRDIEDFQAQKQADHVRYTKWLDGVTVDE

HEFRKIKEYDTEYYVTPLLSGKGYYDINKDFNQDSDKCAAAVAANMFHYWFDRNRDSINR

FLSQSPGENGVIKLENEKTIEVSKFLETYRSDGDYLDKSPFFDLISNSFKGPVWANKLLD

AYINGYGYIHKFAKNTPHSKNNNSKFNFFKKVFDGNLLTDIHQIFDYNTFSDKLSEALYT

GKAIGLAYGPGDILRRSLGHIISVWGADLDDQNRVVAIYVTDSDDKKLTGNERVGLKRYK

VSSDDQGRARLTTRDKIDNTGGEIRSIETLDMGTQEWADYFNKTEKLEPG

(3) SEQ ID NO: 3 and SEQ ID NO: 15 are combined to show the amino acid sequence of the Eq5 protein (SEQ ID NO: 3) under the nucleotide sequence of eq5 gene (SEQ ID NO: 15)

```
atgaagaaattcacgaaacggtgtcttaagggctgtggtcttgttggattagttttcagc
  M  K  K  F  T  K  R  C  L  K  G  C  G  L  V  G  L  V  F  S acaggattggttgccttgtcggataatattgatagcgctttaacagtaggggcggaaacg
  T  G  L  V  A  L  S  D  N  I  D  S  A  L  T  V  G  A  E  T actactgctagtgcatttgaaaataatgggacaggtcaacatctgaactggcacatagat
  T  T  A  S  A  F  E  N  N  G  T  G  Q  H  L  N  K  H  I  D attccacaagaatatacagttgaattaggagaaccaattactatctcagatcttatgagt
  I  P  Q  E  Y  T  V  E  L  G  E  P  I  T  I  S  D  L  M  S caaattacggttactcgtaaaggtagtaatgggactgttaatgatggagatactttgac
  Q  I  T  V  T  R  K  G  S  N  G  T  V  N  D  G  D  T  F  D tttatttcgaatggagatggttcaagaggaattgatacccatggagtaaaaatatggttt
  F  I  S  N  G  D  G  S  R  G  I  D  T  P  G  V  K  I  W  F gacttttacaatgctgcgggtacttcctttttaactgatgaaatgttagcttcgcctaca
  D  F  Y  N  A  A  G  T  S  F  L  T  D  E  M  L  A  S  P  T tatgctgtaccggggggatcttatactattaaagattgggtattctatgggaaaaatgat
  Y  A  V  P  G  G  S  Y  T  I  K  A  W  V  F  Y  G  K  N  D accaaaaagctcttcacatttaaactaaaaaattccaacagcaataaaactgagttaagg
  T  K  K  L  F  T  F  K  L  K  N  S  N  S  N  K  T  E  L  R aagtcgttagaggaggctaagctaaaactcagccagcctgaaggaacgtattctgatgaa
  K  S  L  E  E  A  K  L  K  L  S  Q  P  E  G  T  Y  S  D  E tcactgcaagccttgcaatcagcggttactcttggtaagacctatttaaacagtgaccct
  S  L  Q  A  L  Q  S  A  V  T  L  G  K  T  Y  L  N  S  D  P gatcaaaatacagtagatcaatctattactactattgattccgctattactagtcttgtt
  D  Q  N  T  V  D  Q  S  V  T  T  I  D  S  A  I  T  S  L  V aatcttaatgctttaaatgaagctattaatcaagctacacctttttataacagatggcaaa
  N  L  N  A  L  N  E  A  I  N  Q  A  T  P  F  I  T  D  G  K gagtatcctaaagaagcgtatgacggtcttgtgcaaaagcttgcagcggcagctaagctt
  E  Y  P  K  E  A  Y  D  G  L  V  Q  K  L  A  A  A  A  K  L caaaattcatttggtccttcacaaggagatgttgataaggctgcgactgatttaacgcaa
  Q  N  S  F  G  P  S  Q  G  D  V  D  K  A  A  T  D  L  T  Q
```

```
gctcttacgacgcttaagactgctgtagcgcatgaagccttagatcaagccttggctaag
 A  L  T  T  L  K  T  A  V  A  H  E  A  L  D  Q  A  L  A  K ctgttagagctttaccgagaaaatccaaatcttgctttgacatcagagtctttgaaggaa
 L  L  E  L  Y  R  E  N  P  N  L  A  L  T  S  E  S  L  K  E ttgtacaataaggccattgaagcagcaggtaccttctatagaactgttaacaaggataaa
 L  Y  N  K  A  I  E  A  A  G  T  F  Y  R  T  V  N  K  D  K gagagaaaagacatttcccttatgagctagagcgctacactacagaaacaaattcagtt
 E  R  K  D  I  S  L  Y  E  L  E  R  Y  T  T  E  T  N  S  V gttgatactattttaaaggtaaaggctgcgattgccgaagaaggaaaggcaaaattgcgt
 V  D  T  I  L  K  V  K  A  A  I  A  E  E  G  K  A  K  L  R tctgctttagaccaattaaatgctcttatcggagaaaatctagacctatctccatataca
 S  A  L  D  Q  L  N  A  L  I  G  E  N  L  D  L  S  P  Y  T gcagcttctgctcaagcctatacagaccagctagctaaggctaaggaggtcgcagcagcg
 A  A  S  A  Q  A  Y  T  D  Q  L  A  K  A  K  E  V  A  A  A ggtgagacagcttatgctcaggagacagaaccgacagctattactaacagcttggttaag
 G  E  T  A  Y  A  Q  E  T  E  P  T  A  I  T  N  S  L  V  K gtgttaaatgctaagaaatccctctcagatgccaaggcagccttggttgctaaaccggtc
 V  L  N  A  K  K  S  L  S  D  A  K  A  A  L  V  A  K  P  V gatccagtagatccagtagacccagtggatccggtagacccagtagatcaggtagaccca
 D  P  V  D  P  V  D  P  V  D  P  V  D  P  V  D  P  V  D  P gtggatccggtagacccagtggatccagtagacccagtagacccagtagacccagtggat
 V  D  P  V  D  P  V  D  P  V  D  P  V  D  P  V  D  P  V  D ccggtagacccagtggatccggtagacccggtcgatccaatcgacccagcggatccagta
 P  V  D  P  V  D  P  V  D  P  I  D  P  A  D  P  V aaaccatcagatcctgaggttaagccagagcctaaaccagaatctaagcctgaagctaag
 K  P  S  D  E  V  K  P  E  P  K  P  E  S  K  P  E  A  K aaggaggacaagaaagcagctgataagcagcaagtgcttccggcaactgctgatacagct
 K  E  D  K  K  A  A  D  K  Q  Q  V  L  P  A  T  A  D  T  A aatccattctttacagcagcagctcttgcagttattgcttgtgcaggccagcttgctatt
 N  P  F  F  T  A  A  A  L  A  V  I  A  C  A  G  Q  L  A  I gtgtcaagacgcaaagaatcaaattaactgtaggcgatgattttcccotttaattaatt
 V  S  R  R  K  E  S  N  -  L  -  A  M  I  F  P  L  -  L  I
```

(4) SEQ ID NO: 4 shows the recombinant Eq 5 protein sequence: The amino acids in bold are those that corresponds to the amino acids encoded by the pTYB4 vector while the rest originates from the Eq5 protein.
METTTASAFENNGTGQHLNWHIDIPQEYTVELGEPITISDLMSQITVTRKGSNGTVNDGD

TFDFISNGDGSRGIDTPGVKIWFDFYNAAGTSFLTDEMLASPTYAVPGGSYTIKAWVFYG

KNDTKKLFTFKLKNSNSNKTELRKSLEEAKLKLSQPEGTYSDESLQALQSAVTLGKTYLN

SDPDQNTVDQSVTTIDSAITSLVNLNALNEAINQATPFITDGKEYPKEAYDGLVQKLAAA

AKLQNSFGPSQGDVDKAATDLTQALTTLKTAVAHEALDQALAKLLELYRENPNLALTSES

LKELYNKAIEAAGTFYRTVNKDKERKDISLYELERYTTETNSVVDTILKVKAAIAEEGKA

KLRSALDQLNALIGENLDLSPYTAASAQAYTDQLAKAKEVAAAGETAYAQETEPTAITNS

LVKVLNAKKSLSDAKAALVAKPLEPG

(5) SEQ ID NO: 5 and SEQ ID NO: 16 are combined to show the amino acid sequence of the Eq8 protein (SEQ ID NO: 5) under the nucleotide sequence of eq8 gene (SEQ ID NO: 16)
```
atgaacaaaaaatcagcaagacgcaggcgtaagaatcttattacgaagcttgcgatgaca
 M  N  K  K  S  A  R  R  R  R  K  N  L  I  T  K  L  A  M  T agtgccttaaccctgggtgtaggcgcagcgactaccctagcaggacaaacagaagtacgg
 S  A  L  T  L  G  V  G  A  A  T  T  L  A  G  Q  T  E  V  R
```

```
gctgataatatcttacgcttagatatgacagataaagaagcagttgaaaaattcgctaac
 A  D  N  I  L  R  L  D  M  T  D  K  E  A  V  E  K  F  A  N gagcttaaaaatgaagtccataaaaactatcgtggtagtaatacttggcaaaagcttacc
 E  L  K  N  E  V  H  K  N  Y  R  G  S  N  T  W  Q  K  L  T cttatacttaatggttatcaaaaccttagagaacaaatagagaccgagctaaaaaatagt
 L  I  L  N  G  Y  Q  N  L  R  E  Q  I  E  T  E  L  K  N  S gaacaaaaagtaaaagagcttaatgataaggttaatagtgaaactcaaggaaaacaagag
 E  Q  K  V  K  E  L  N  D  K  V  N  S  E  T  Q  G  K  Q  E ttacagaatcagcttgagaaagaaaaagaagagttagaaacactaaaaaaagagcttgaa
 L  Q  N  Q  L  E  K  E  K  E  E  L  E  T  L  K  K  E  L  E gctgagaaggctaaaggaactggagaaacagagaagcttcaaaaggaaattgaagcaaaa
 A  E  K  A  K  G  T  G  E  T  E  K  L  Q  K  E  I  E  A  K aatgcaatgatttctgacctacaaaaacagcttgaggaaactaagcaaagggttcaagag
 N  A  M  I  S  D  L  Q  K  Q  L  E  E  T  K  Q  R  V  Q  S tttgaagctgaagtaggtaaattaatggccgaaaaggcagacctacaaacaaaattaaat
 F  E  A  E  V  G  K  L  M  A  E  K  A  D  L  Q  T  K  L  N gaacaagagcagcttaacgctaagcttcaaaaagaaattgaagacttaaaggctcagatt
 E  Q  E  Q  L  N  A  K  L  Q  K  E  I  E  D  L  K  A  Q  I gaaaagcttaagcactgtcaagatacacctaagccagagcctaagccagagcctaagcca
 E  K  L  K  H  C  Q  D  T  P  K  P  E  P  K  P  E  P  K  P gagcctaagccagagcctaagccagagcctaagccagagcctaagccagagcctaagcca
 E  P  K  P  E  P  P  E  P  P  K  P  E  P  K  P  E  P  K  P gagcctaagccagggcctaaaccagagcctaagccagagcctaagccagggcctaagcca
 E  P  K  P  G  P  K  P  E  P  K  P  E  P  K  P  G  P  K  P gagcctaagccagagcctaagccagggcctaagccagggcctaagccagagcctaagcca
 E  P  K  P  E  P  K  P  G  P  K  P  G  P  K  P  E  P  K  P gggcctaagccagagcctaagccagagcctaagccagagcctaagcctgaagctaagaag
 G  P  K  P  E  P  K  P  E  P  K  P  E  P  K  P  E  A  K  K cctgaacaacctaaaccaatgactaaaccaggagctaagaagcctgagcaatcacttcca
 P  E  Q  P  K  P  M  T  K  P  G  A  K  K  P  E  Q  S  L  P tcaactggtgacatcagaaatccattcttcacgcctgcagctattgctattatgatcgca
 S  T  G  D  I  R  N  P  F  F  T  P  A  A  I  A  I  M  I  A gcaggtaccattgccattccaaaacgcaaggaagaagattaaacaaattaacaatcccca
 A  G  T  I  A  I  P  K  R  K  E  E  D  -  T  N  -  Q  S  P
```

(6) SEQ ID NO: 6 shows the recombinant Eq8 protein sequence: The amino acids in bold are those that corresponds to the amino acids encoded by the pTYB4 vector while the rest originates from the Eq8 protein.

MATTLAGQTEVRADNILRLDMTDKEAVEKFANELKNEVHKNYRGSNTWQKLTLILNGYQN

LREQIETELKNSEQKVKELNDKVNSETQGKQELQNQLEKEKEELETLKKELEAEKAKGTG

ETEKLQKEIEAKNAMISDLQKQLEETKQRVQEFEAEVGKLMAEKADLQTKLNEQEQLNAK

LQKEIEDLKAQIEKLKHLEPG

(7) SEQ ID NO: 7 and SEQ ID NO: 17 are combined to show the amino acid sequence of the IdeZ2 protein (SEQ ID NO: 7) under the nucleotide sequence of the ideZ2 gene (SEQ ID NO: 17) from *S. equi* subsp. *zooepidemious*

```
atgatgaaaaaacaatcattcacacactcacgtaaacctaaattcggtatgagaaaatta
 M  M  K  K  Q  S  F  T  H  S  R  K  P  K  F  G  M  R  K  L tctattggccttgcctcatgtatgctaggaatgatgttcctaacaacaagccatgtttct
 S  I  G  L  A  S  C  M  L  G  M  M  F  L  T  T  S  H  V  S ggtgaggtagttgaagtttggccttatgggcaagatcctaatgataaaatagaagtttta
 G  E  V  V  E  V  W  P  Y  G  Q  D  F  N  D  K  I  E  V  L
```

```
agtcaatctgagtattccgaatatttacagagattacacgatgttgaagatttccaagct
 S  Q  S  E  Y  S  E  Y  L  Q  R  L  H  D  V  E  D  F  Q  A gaaaagaaaaagaaggagttgtccgtacacaatggttagagggtgtgaacattactgac
 E  K  K  E  G  V  V  R  T  Q  W  L  E  G  V  N  V  T  D catgacttccggaaaatcactgatggtggtagtgtttattatgccacacctcttttaaat
 H  D  F  R  K  I  T  D  G  G  S  V  Y  Y  A  T  P  L  L  N gatagaggatattataatatcaacaagaatttcaatcaagacagtgataaatgtgctgct
 D  R  G  Y  Y  D  I  N  K  N  F  N  Q  D  S  D  K  C  A  A gctgtggcagttaatatgttacattattggcttgataggaataaagataatgtagctaag
 A  V  A  V  N  M  F  H  Y  W  L  D  R  N  K  D  N  V  A  K tttcttagtcaaagtccagaccatggttttgttgaaggtgaacctacttttaacttagta
 F  L  S  Q  S  P  D  H  G  F  V  E  G  E  P  T  F  N  L  V gattttcaatatacatatgcatctccatatgaagaaggaggatatagggacaatagtaaa
 D  F  Q  Y  T  Y  A  S  P  Y  E  E  G  G  Y  R  D  N  S  K ctcttcgactttattagcaagacttttaataagcctctttgggcaaataaattgttagat
 L  F  D  F  I  S  K  A  F  N  K  P  L  W  A  N  K  L  L  D gcttacattaatggctatggctatatcgacagatacgttaaaaataccccgcattctgga
 A  Y  I  N  G  Y  G  Y  I  D  R  Y  V  K  N  T  P  H  S  G caaaataatagtaaatttaatttctttaaaaaagtatttgatggcaagctcttgacagat
 Q  N  N  S  K  F  N  F  F  K  K  V  F  D  G  K  L  L  T  D attcaacaattttttgattattatactttatcgtctgagctacgtgaagatattgatact
 I  Q  Q  I  F  D  Y  Y  T  L  S  S  E  L  R  E  A  L  D  T ggcaaagctattggtttagcctatggacctggagatttacgccgttctctgggacatatt
 G  K  A  I  G  L  A  Y  G  P  G  D  L  R  R  S  L  G  H  I atctccgtctggggagctgacattaatgaagatggaaatgtcgtggctatttatgtgact
 I  S  V  W  G  A  D  I  N  E  D  G  N  V  V  A  I  Y  V  T gattccgatgataaaaaattaactatagggaataaaaaagaccgaattggtttgaagcga
 D  S  D  D  K  K  L  T  I  G  N  K  K  D  R  I  G  L  K  R tacaaactgtattctgataacgtgggacgagatcgcctaacagcctatgctacagaaaac
 Y  K  L  Y  S  D  N  V  G  R  A  R  L  T  A  Y  A  T  E  N caacaaactggtggtgaagttcgagggattgaaactttagatatggatacacaagattgg
 Q  Q  T  G  G  E  V  R  G  I  E  T  L  D  M  A  T  Q  D  W gcagattattbtagcaggacagacgaagcagaacaataa
 A  D  Y  F  S  R  T  D  E  A  E  Q  -

(8) SEQ ID NO: 8 and SEQ ID NO: 18 are combined to show the amino
acid sequence of the Eqz5 protein (SEQ ID NO: 8) under the
nucleotide sequence of the eqz5 gene (SEQ ID NO: 18) from S. equi
subsp. zooepidemicus
atgaagaaattcacgaaacggtgtctt
 M  K  K  F  T  K  R  C  L aagggctgcggtcttgttggattagttttcagcacaggattggttgccttgtcagataat
 K  G  C  G  L  V  G  L  V  F  S  T  G  L  V  A  L  S  D  N attgatagcgctttaacagtaggggcggaaacggctactactgataatgcatttgaagaa
 I  D  S  A  L  T  V  G  A  E  T  A  T  T  A  N  A  F  E  E agtggtgaccaacaacataaaaattggcatatttatattccagaggtttatactgttaaa
 S  G  D  Q  Q  H  K  N  W  H  I  Y  I  P  E  V  Y  T  V  K gtcggtcagccaatcaccattgaggatatcttaagtcagattacgattactcgtaaggga
 V  G  Q  P  I  T  I  E  D  I  L  S  Q  I  T  I  T  R  K  G gaagattcgcaaggtaaaacatctcccggaatgatctatacttatgaagaatacctaaa
 E  D  S  Q  G  K  T  S  P  G  M  I  Y  T  Y  E  E  Y  P  K gtacgaggaattgaagtttcagcaggaactatttggtttgattttataattctggaaac
 V  R  G  I  E  V  S  A  G  T  I  W  F  D  F  Y  N  S  G  N
```

LIST OF SEQUENCES

```
tgggtaaataatgatgttttagctaccttcaacgaacctggaggaacttatacctatct
 W  V  N  N  D  V  L  A  T  F  N  E  P  G  G  T  Y  T  L  S gcttgggcatactatgctaacgaaaatgtaaaaaaacaatttgttttcaaacttcaagtt
 A  W  A  Y  Y  A  N  E  N  V  K  K  Q  F  V  F  K  L  Q  V gaaaatagtgataagcgtgcattagaacaatctcttgctactgctaacgaaaagttacag
 E  N  S  D  K  R  A  L  E  Q  S  L  A  T  A  N  E  K  L  Q gctcctgaaggaacgtattctgatgaatcactgcaacgtttacaagaatcagttttcctt
 A  P  E  G  T  Y  S  D  E  S  L  Q  R  L  Q  E  S  V  F  L ggtcaaacttatttgaacagggatcctgagcaacaagaagtggacgatatgaaggcaact
 G  Q  T  Y  L  N  R  D  P  E  Q  Q  E  V  D  D  M  K  A  T attgattctgctgtttctggtcttgttgatcttactgtcttaaataccgcagttgaaaca
 I  D  S  A  V  S  G  L  V  D  L  T  V  L  N  T  A  V  E  T gcaacaccattgttaacagatggtaaggagtatcctaaagaagcgtatgatagccttgtt
 A  T  P  L  L  T  D  G  K  E  Y  P  K  E  A  Y  D  S  L  V caaaagcttgcagcagcagctaagcttcaaaattcctttaacccatcacaagaagaagtt
 Q  K  L  A  A  A  A  K  L  Q  N  S  F  N  P  S  Q  E  E  V aacgaggctgcgactgatttaacgcaagctcttacgacgcttaagactgctgtagcgcat
 N  E  A  A  T  D  L  T  Q  A  L  T  T  L  K  T  A  V  A  N gaagccttagatcaagccttggctaagctgttagagatttaccgagaaaatccaaacctt
 E  A  L  D  Q  A  L  A  K  L  L  E  L  Y  R  E  N  P  N  L gctttgacatcagagcctttgaaggaattgtacaataaggccattgaagcagcaggcacc
 A  L  T  S  E  P  L  K  E  L  Y  N  K  A  I  E  A  A  G  T ttctatagaactgttagcaaggataaagagagaaaaggcatttccctttatgagctagag
 F  Y  R  T  V  S  K  D  K  E  R  K  G  I  S  L  Y  E  L  E cgttacactacagaaacaaactcagttgttgatactattttaaaggtaaaggctgcaatt
 R  Y  T  T  E  T  N  S  V  V  D  T  I  L  K  V  K  A  A  I gccgaagaaggaaaggcaaaattgcgttctcctttagaccaattaaatgctcttatcgga
 A  E  E  G  N  A  K  L  R  S  A  L  D  Q  L  N  A  L  I  G gaaaatctagacctatctccatatacagcagcttctgctcaagcctatacagaccagcta
 E  N  L  D  L  S  P  Y  T  A  A  S  A  Q  A  Y  T  D  Q  L gctaaggctaaggaggttgcagcagcgggtgagacagcttatgctcaggagacagaaccg
 A  K  A  K  E  V  A  A  A  G  E  T  A  Y  A  Q  E  T  E  P acagctattactaacagcttgattaaggtgctaaatgctaagaaatccctctcagatgcc
 T  A  I  T  N  S  L  I  K  V  L  N  A  K  K  S  L  S  D  A aaggcagcattggttgctaaaccggtagatccggtagacccagtagatccggtagaccca
 K  A  A  L  V  A  K  P  V  D  P  V  D  P  V  D  P  V  D  P gtggatccggtagacccaattgatccagtagatccagtaaaaccagtcgatcctgaggtt
 V  D  P  V  D  P  I  D  P  V  D  P  V  K  P  V  D  P  E  V aagccagagcctaaaccagaatctaagcctgaagctaagaaggaggacaagaaagcagct
 K  P  E  P  K  P  E  S  K  P  E  A  K  K  E  D  K  K  A  A gataagcagcaagtgcttccggcaactgctgatacagctaacccattatttacagcagca
 D  K  Q  Q  V  L  P  A  T  A  D  T  A  N  P  F  F  T  A  A
```

-continued

LIST OF SEQUENCES

```
gctcttgcagttattgcttgtgcaggccagcttgctattgtgtcaagacgcaaagaatca
 A  L  A  V  I  A  C  A  G  Q  L  A  I  V  S  R  R  K  E  S aattaa
 N  -
```

(9) SEQ ID NO: 9 and SEQ ID NO: 19 are combined to show the amino acid sequence of the Eqz8 protein (SEQ ID NO: 9) under the nucleotide sequence of the eqz8 gene (SEQ ID NO: 19) from *S. equi* subsp. *zooepidemicus*

```
atgaacaaaaaatcagca
 M  N  K  K  S  A agacgcaagcgtaaggatcttatcacgaagcttgcgatgacaagtgccttaaccctgggt
 R  R  K  R  K  D  L  I  T  K  L  A  M  T  S  A  L  T  L  G gtaggcgcagcagctaccatagcaggacaaacagaagtacgggctgaggttctaacctta
 V  G  A  A  A  T  I  A  G  Q  T  E  V  R  A  E  V  L  T  L aatatgaaagataaagctaaagttgaagaattcgctaataagcttaaagattacgcaaag
 N  M  K  D  K  A  K  V  E  E  F  A  N  K  L  K  D  Y  A  K caaaagaaatctggccaaattactttgcaagaactttcccttatacttgatgggtacaga
 Q  K  K  S  G  Q  I  T  L  Q  E  L  S  L  I  L  D  G  Y  R aatattagggagcagatagaacaagacttagctactacagaaaaaactaaaaatttctat
 N  I  R  E  Q  I  E  Q  D  L  A  T  T  E  K  T  K  N  F  Y ggagaacagttaattcttactgataaactttatcagtctgaaaaagaaaagaaagaaaag
 G  E  Q  L  I  L  T  D  K  L  Y  Q  S  E  K  E  K  K  E  K ctagaagctgagctacaactaagccaacaaaaaattcatgaccttgatgaaaaacatcaa
 L  E  A  E  L  Q  L  S  Q  Q  K  I  H  D  L  D  E  K  H  Q aaagagaaattagagctacaagaacaacttgaggcttcaaatcaaaagattaaagagctt
 K  E  K  L  E  L  Q  E  Q  L  E  A  S  N  Q  K  I  K  E  L gaaatggcaaaagagcacagctgaagctgaaataaatagactaacagctgaaaaaaatgga
 E  M  A  K  S  T  A  E  A  E  I  N  R  L  T  A  E  K  N  G ttacaagaaaaattaaataatcaagaaaagcttaatgctgagttacaagcaaaattagct
 L  Q  E  K  L  N  N  Q  E  K  L  N  A  E  L  Q  A  K  L  A aagcaagaagagcttaacgctaagcttcaaaaggaaattgacgaattaaatgctcagctt
 K  Q  E  E  L  N  A  K  L  Q  K  E  I  D  E  L  N  A  Q  L gaaaagcttaagcattgtcaagatacacctaagccagagcctaagccagagcctaagcca
 E  K  L  K  H  C  Q  D  T  P  K  P  E  P  K  P  E  P  K  P gagcctaagccagagactaagccagagcctaagccagagcctaagccagagcctaagcca
 E  P  K  P  E  P  K  P  E  P  K  P  E  P  K  P  E  P  K  P gagcctaagccagagcctaagccagagcctaagccagagcctaagccagagcctaagcca
 E  P  K  P  E  P  K  P  E  P  K  P  E  P  K  P  E  P  K  P gagcctaagccagagcctaagccagagcctaagccagagcctaagccagaacctaagcca
 E  P  K  P  E  P  K  P  E  P  K  P  E  P  K  P  E  P  K  P gagcctaagccagagcctaagccagagcctaagccagagcctaagccagagcctaagcca
 E  P  K  P  E  P  K  P  E  P  K  P  E  P  K  P  E  P  K  P gagcctaagccagagcctaagccagagcctaagccagagcctaagccagagcctaagcca
 E  P  K  P  E  P  K  P  E  P  K  P  E  P  K  P  E  P  K  P gagcctaagccagagcctaagcctgaagctaaaaagcctgaacaacctaaaccaatgact
 E  P  K  P  E  P  K  P  E  A  K  K  P  E  Q  P  K  P  M  T aaaccaggggctaagaagcctgagcaatcacttccatcaactggtgacatcagaaatcca
 K  P  G  A  K  K  P  E  Q  S  L  P  S  T  G  D  I  R  N  P
```

```
ttcttcacacctgcagctattgctattatgatcgcagcaggtaccattgcaattccaaaa
 F  F  T  P  A  A  I  A  I  M  I  A  A  G  T  I  A  I  P  K cgcaaggaagaagactaa
 R  K  E  E  D  -
```

(10) SEQ ID NO: 10 and SEQ ID NO: 20 are combined to show the amino acid sequence of the IdeE protein (SEQ ID NO: 10) under the nucleotide sequence of the ideE gene (SEQ ID NO: 20).

The nucleotide sequence of the ideE gene (GenBank DQ508733) and the amino acid sequence of the IdeE protein from *S. equi* subsp. *equi* are shown.

```
atgaaaacaatagcttatccaaataaacctcactccttatcagctggtctattaactgat
 M  K  T  I  A  Y  P  N  K  P  H  S  L  S  A  G  L  L  T  A atagctattttagcctggcgagttcaaacattactatgctgacgattaccaaggaat
 I  A  I  F  S  L  A  S  S  N  I  T  Y  A  D  D  Y  Q  R  N gctacggaagcttatgccaaagaagtaccacatcagatcacttctgtatggaccaaggt
 A  T  E  A  Y  A  K  S  V  P  H  Q  I  T  S  V  W  T  K  G gttacaccactaacacccgagcagtttcgatataataacgaagatgtgatccatgcgcca
 V  T  P  L  T  P  E  Q  F  R  Y  N  N  E  D  V  I  H  A  P tatcttgctcatcaaggctggtacgatatcaccaaggccttcgatgggaaggataatctc
 Y  L  A  H  Q  G  W  Y  D  I  T  K  A  F  D  G  K  D  N  L ttgtgtggcgcagcaacggcaggtaatatgctgcattggtggtttgatcaaaataaaaca
 L  C  G  A  A  T  A  G  N  M  L  H  W  W  F  D  Q  N  K  T gagattgaagcctatttaagtaaacaccctgaaaagcaaaaaatcattttaacaaccaa
 E  I  E  A  Y  L  S  K  H  P  E  K  Q  K  I  I  F  N  N  Q gagctatttgatttgaaagctgctatcgataccaaggacagtcaaaccaatagtcagctt
 E  L  F  D  L  K  A  A  I  D  T  K  D  S  Q  T  N  S  Q  L tttaattattttagagataaagccttttccaaatctatcagcacgtcaactcggggttatg
 F  N  Y  F  R  D  K  A  F  P  N  L  S  A  R  Q  L  G  V  M cctgatcttgttctagacatgttttatcaatggttactacttaaatgtgtttaaaacacag
 P  D  L  V  L  D  M  F  I  N  G  Y  Y  L  N  V  F  K  T  Q tctactgatgtcaatcgacccttatcaggacaaggacaaacgaggtggtattttcgatgct
 S  T  D  V  N  R  P  Y  Q  D  K  D  K  R  G  G  I  F  D  A gttttcaccagaggagatcagacaacgctcttgacagctcgtcatgatttaaaaaataaa
 V  F  T  R  G  D  Q  T  T  L  L  T  A  R  H  D  L  K  N  K ggactaaatgacatcagcaccattatcaagcaagaactgactgaaggaagagcccttgct
 G  L  N  D  I  S  T  I  I  K  Q  E  L  T  E  G  R  A  L  A ttatcacatacctacgccaatgttagcattagccatgtgattaacttgtggggagctgat
 L  S  H  T  Y  A  N  V  S  I  S  H  V  I  N  L  W  G  A  D tttaatgctgaaggaaaccttgaggccatctatgtcacagactcagatgctaatgcgtct
 F  N  A  E  G  N  L  E  A  I  Y  V  T  D  S  D  A  N  A  S attggtatgaaaaaatattttgtggcattaatgctcatagacatgtcgccatttctgcc
 I  G  M  K  K  Y  F  V  G  I  N  A  H  R  H  V  A  I  S  A aagaaaatagaaggagaaaacattggcgctcaagtattaggcttatttacgctttccagt
 K  K  I  E  G  E  N  I  G  A  Q  V  L  G  L  F  T  L  S  S ggcaaggacatatggcagaaactgagctaa
 G  K  D  I  W  Q  K  L  S  -
```

(11) SEQ ID NO: 11 and SEQ ID NO: 21 are combined to show the amino acid sequence of the IdeZ protein (SEQ ID NO: 11) under the nucleotide sequence of the ideZ gene (SEQ ID NO: 21).

The nucleotide sequence of the ideZ gene (Genbank DQ826037) and the amino acid sequence of the IdeZ protein from *S. equi* subsp. *zooepidemicus* are shown.

```
atgaaaacaatagcttatccaaataaacctcactccttatcagctggtctcttaactgct
 M  K  T  I  A  Y  P  N  K  P  H  S  L  S  A  G  L  L  T  A
```

```
atagctattttttagcctggcgagttcaaacattacttatgctgacgattaccaaggaat
 I   A  I  F  S  L  A  S  S  N  I  T  Y  A  D  D  Y  Q  R  N gctgcggaagtttatgccaaagaagtaccacatcagatcacttctgtatggaccaaaggt
 A  A  E  V  Y  A  K  E  V  P  H  Q  I  T  S  V  W  T  K  G gttacaccactaacacccgagcagtttcgatataataacgaagatgtgatccatgcgcca
 V  T  P  L  T  P  E  Q  F  R  Y  N  N  E  D  V  I  H  A  P tatcttgctcatcaaggctggtacgatatcaccaaggtattcgatgagaaggataatctc
 Y  L  A  H  Q  G  W  Y  D  I  T  K  V  F  D  G  K  D  N  L ttgtgtggcgcagcaacggcaggtaatatgctgcattggtggtttgatcaaaataaaaca
 L  C  G  A  A  T  A  G  N  M  L  H  W  W  F  D  Q  N  K  T gagattgaagcctatttaagtaaacaccatgaaaagcaaaaaatcattttttaacaaccaa
 E  I  E  A  Y  L  S  K  H  P  E  K  Q  K  I  I  F  N  N  Q gagctatttgatttgaaagctgctatcgataccaaggacagtcaaaccaatagtcagctt
 E  L  F  D  L  K  A  A  I  D  T  K  D  S  Q  T  N  S  Q  L tttaattatttttagagataaagcctttccaaatctatcagcacgtcaactccaggttatg
 F  N  Y  F  R  D  K  A  F  P  N  L  S  A  R  Q  L  G  V  M cctgatattgttctagacatgtttatcaatggttactacttaaatgtgtttaaaacacag
 P  D  L  V  L  D  M  F  I  N  G  Y  Y  L  N  V  F  K  T  Q tctactgatatcaatcgaccttatcaggacaaggacaaacgaggtggtatttttcgatgct
 S  T  D  V  N  R  P  Y  Q  D  K  D  K  R  G  G  I  F  D  A gttttcaccagaggagatcagacaacgctcttgacagctcgtcatgatttaaaaaataaa
 V  F  T  R  G  D  Q  T  T  L  L  T  A  R  H  D  L  K  N  K ggactaaatgacatcagcaccattatcaagcaggaactgactgaaggaagagcccttgct
 G  L  N  D  I  S  T  I  I  K  Q  E  L  T  E  G  R  A  L  A ttatcacatacctacgccaatgttagcattagccatgtgattaacttgtggggagctgat
 L  S  H  T  Y  A  N  V  S  I  S  H  V  I  N  L  W  G  A  D tttaatgctgaaggaaaccttgaggccatctatgtcacagactcagatgctaatgcgtct
 F  N  A  E  G  N  L  E  A  I  Y  V  T  D  S  D  A  N  A  S attggtatgaaaaaatattttgtcggcattaatgctcatggacatgtcgccatttctgcc
 I  G  M  K  K  Y  F  V  G  I  N  A  H  G  H  V  A  I  S  A aagaaaatagaaggagaaaacattggcgctcaagtattaggcttatttacgctttccagt
 K  K  I  E  G  E  N  I  G  A  Q  V  L  G  L  F  T  L  S  S ggcaaggacatatggcagaaactgagctaa
 G  K  D  I  W  Q  K  L  S  -
```

(12) SEQ ID NO: 12
Nucleotide sequence of the eag gene

```
  1 aaataatttttgtttaactttaagaaggagatataaccatgcctctagatg 51 ctacaacggtgttagagcctacaacagccttcattagagaagctgttagg 101 gaaatcaatcagctgagtgatgactacgctgacaatcaagagcttcaggc 151 tgttcttgctaatgctggagttgaggcacttgctgcagatactgttgatc 201 aggctaaagcagctcttgacaaagcaaaggcagctgttgctggtgttcag 251 cttgatgaagcaagacgtgaggcttacagaacaatcaatgccttaagtga 301 tcagcacaaaagcgatcaaaaggttcagctagctctagttgctgcagcag 351 ctaaggtggcagatgctgcttcagttgatcaagtgaatgcagccattaat 401 gatgctcatacagctattgaggacattacaggagcagccttgttggaggc 451 taaagaagctgctatcaatgaactaaagcagtatggcattagtgattact 501 atgtgaccttaatcaacaaagccaaaactgttgaaggtgtcaatgcgctt 551 aaggcaaagattttatcagctctaccgtagctcgagcccgggtgctttgc
```

LIST OF SEQUENCES

(13) SEQ ID NO: 13
Amino acid sequence of the EAG4B protein
```
  1 MALDATTVLE PTTAFIREAV REINQLSDDY ADNQELQAVL ANAGVEALAA DTVDQAKAAL

61 DKAKAAVAGV QLDEARREAY RTINALSDQH KSDQKVQLAL VAAAAKVADA ASVDQVNAAI

121 NDAHTAIADI TGAALLEAKE AAINELKQYG ISDYYVTLIN KAKTVEGVNA LKAKILSALP
```

(14) SEQ ID NO: 28
Protein sequence of SEC2.16 (CNE)

```
Met Ala Thr Asn Leu Ser Asp Asn Ile Thr Ser Leu Thr Val Ala Ser
1               5                   10                  15

Ser Ser Leu Arg Asp Gly Glu Arg Thr Thr Val Lys Val Ala Phe Asp
            20                  25                  30

Asp Lys Lys Gln Lys Ile Lys Ala Gly Asp Thr Ile Glu Val Thr Trp
            35                  40                  45

Pro Thr Ser Gly Asn Val Tyr Ile Gln Gly Phe Asn Lys Thr Ile Pro
            50                  55                  60

Leu Asn Ile Arg Gly Val Asp Val Gly Thr Leu Glu Val Thr Leu Asp
65                  70                  75                  80

Lys Ala Val Phe Thr Phe Asn Gln Asn Ile Glu Thr Met His Asp Val
                85                  90                  95

Ser Gly Trp Gly Glu Phe Asp Ile Thr Val Arg Asn Val Thr Gln Thr
            100                 105                 110

Thr Ala Glu Thr Ser Gly Thr Thr Thr Val Lys Val Gly Asn Arg Thr
            115                 120                 125

Ala Thr Ile Thr Val Thr Lys Pro Glu Ala Gly Thr Gly Thr Ser Ser
130                 135                 140

Phe Tyr Tyr Lys Thr Gly Asp Ile Gln Pro Asn Asp Thr Glu Arg Val
145                 150                 155                 160

Arg Trp Phe Leu Leu Ile Asn Asn Lys Glu Trp Val Ala Asn Thr
                165                 170                 175

Val Thr Val Glu Asp Asp Ile Gln Gly Gly Gln Thr Leu Asp Met Ser
                180                 185                 190

Ser Phe Asp Ile Thr Val Ser Gly Tyr Arg Asn Glu Arg Phe Val Gly
            195                 200                 205

Glu Asn Ala Leu Thr Glu Phe His Thr Thr Phe Pro Asn Ser Val Ile
210                 215                 220

Thr Ala Thr Asp Asn His Ile Ser Val Arg Leu Asp Gln Tyr Asp Ala
225                 230                 235                 240

Ser Gln Asn Thr Val Asn Ile Ala Tyr Lys Thr Lys Ile Thr Asp Phe
                245                 250                 255

Asp Gln Lys Glu Phe Ala Asn Asn Ser Lys Ile Trp Tyr Gln Ile Leu
            260                 265                 270

Tyr Lys Asp Gln Val Ser Gly Gln Glu Ser Asn His Gln Val Ala Asn
            275                 280                 285

Ile Asn Ala Asn Gly Gly Val Asp Gly Ser Arg Tyr Thr Ser Phe Thr
            290                 295                 300

Val Lys Lys Ile Trp Asn Asp Lys Glu Asn Gln Asp Gly Lys Arg Pro
305                 310                 315                 320

Lys Thr Ile Thr Val Gln Leu Tyr Ala Asn Asp Gln Lys Val Asn Asp
                325                 330                 335

Lys Thr Ile Glu Leu Ser Asp Thr Asn Ser Trp Gln Ala Ser Phe Gly
                340                 345                 350
```

-continued

| LIST OF SEQUENCES |
|---|

Lys Leu Asp Lys Tyr Asp Ser Gln Asn Gln Lys Ile Thr Tyr Ser Val
   355        360        365

Lys Glu Val Met Val Pro Val Gly Tyr Gln Ser Gln Val Glu Gly Asp
   370        375        380

Ser Gly Val Gly Phe Thr Ile Thr Asn Thr Tyr Thr Pro Glu Val Ile
385        390        395        400

Ser Ile Thr Gly Gln Lys Thr Trp Asp Asp Arg Glu Asn Gln Asp Gly
      405        410        415

Lys Arg Pro Lys Glu Ile Thr Val Arg Leu Leu Ala Asn Asp Ala Ala
   420        425        430

Thr Asp Lys Val Ala Thr Ala Ser Glu Gln Thr Gly Trp Lys Tyr Thr
   435        440        445

Phe Thr Asn Leu Pro Lys Tyr Lys Asp Gly Lys Gln Ile Thr Tyr Thr
   450        455        460

Ile Gln Glu Asp Pro Val Ala Asp Tyr Thr Thr Thr Ile Gln Gly Phe
465        470        475        480

Asp Ile Thr Asn His His Glu Val Ala Leu Thr Ser Leu Lys Val Ile
      485        490        495

Lys Val Trp Asn Asp Lys Asp Tyr Tyr His Lys Arg Pro Lys Glu
      500        505        510

Ile Thr Ile Leu Leu Lys Ala Asp Gly Lys Val Ile Arg Glu His Gln
   515        520        525

Met Thr Pro Asp Gln Gln Gly Lys Trp Glu Tyr Thr Phe Asp Gln Leu
   530        535        540

Pro Val Tyr Gln Ala Gly Lys Lys Ile Ser Tyr Ser Ile Glu Glu Lys
545        550        555        560

Gln Val Ala Gly Tyr Gln Ala Pro Val Tyr Glu Val Asp Glu Gly Leu
      565        570        575

Lys Gln Val Thr Val Thr Asn Thr Leu Asn Pro Ser Tyr Lys Leu Glu
   580        585        590

Pro Gly

(15) SEQ ID NO 29
Protein sequence of SclC
Met Thr Asn Lys Thr Lys Arg Thr Gly Leu Val Arg Lys Tyr Gly Ala
1        5        10        15

Cys Ser Ala Ala Ile Ala Leu Ala Ala Leu Ala Ser Leu Gly Ala Gly
      20        25        30

Lys Ala Val Lys Ala Asp Gln Pro Ala Ala Leu Lys Tyr Pro Glu Pro
   35        40        45

Arg Asp Tyr Phe Leu His Thr Arg Glu Gly Asp Val Ile Tyr Asp Glu
   50        55        60

Asp Ile Lys Arg Tyr Phe Glu Asp Leu Glu Ala Tyr Leu Thr Ala Arg
65        70        75        80

Leu Gly Gly Ile Asp Lys Lys Val Glu Glu Ala Ala Gln Lys Pro Gly
      85        90        95

Ile Pro Gly Pro Thr Gly Pro Gln Gly Pro Lys Gly Asp Lys Gly Asp
      100        105        110

Pro Gly Ala Pro Gly Glu Arg Gly Pro Ala Gly Pro Lys Gly Asp Thr
   115        120        125

Gly Glu Ala Gly Pro Arg Gly Glu Gln Gly Pro Ala Gly Gln Ala Gly
   130        135        140

LIST OF SEQUENCES

```
Glu Arg Gly Pro Lys Gly Asp Pro Gly Ala Pro Gly Pro Lys Gly Glu
145                 150                 155                 160

Lys Gly Asp Thr Gly Ala Val Gly Pro Lys Gly Glu Lys Gly Asp Thr
                165                 170                 175

Gly Ala Thr Gly Pro Lys Gly Asp Lys Gly Glu Arg Gly Glu Lys Gly
            180                 185                 190

Glu Gln Gly Gln Arg Gly Glu Lys Gly Glu Gln Gly Gln Arg Gly Glu
        195                 200                 205

Lys Gly Glu Gln Lys Pro Lys Gly Asp Gln Gly Lys Asp Thr Lys Pro
    210                 215                 220

Ser Ala Pro Lys Ala Pro Glu Lys Ala Pro Ala Pro Lys Ala Pro Lys
225                 230                 235                 240

Ala Ser Glu Gln Ser Ser Asn Pro Lys Ala Pro Ala Pro Lys Ser Ala
                245                 250                 255

Pro Ser Lys Ser Ala Ala Pro Thr Gly Gln Lys Ala Ala Leu Pro Ala
            260                 265                 270

Thr Gly Glu Ile Asn His Pro Phe Phe Thr Leu Ala Ala Leu Ser Val
            275                 280                 285

Ile Ala Ser Val Gly Val Leu Thr Leu Lys Gly Lys Lys Asp
            290                 295                 300
```

(16) SEQ ID NO 30. Recombinant protein IdeE

GPLGSDDYQRNATEAYAKEVPHQITSVWTKGVTPLTPEQFRYNNEDVIHAPYLA

HQGWYDITKAFDGKDNLLCGAATAGNMLHWWFDQNKTEIEAYLSKHPEKQKIIFNNQELF

DLKAAIDTKDSQTNSQLFNYFRDKAFPNLSARQLGVMPDLVLDMFINGYYLNVFKTQSTD

VNRPYQDKDKRGGIFDAVFTRGDQTTLLTARHDLKNKGLNDISTIIKQELTEGRALALSH

TYANVSISHVINLWGADFNAEGNLEAIYVTDSDANASIGMKKYFVGINAHRHVAISAKKI

EGENIGAQVLGLFTLSSGKDIWQKLS

Amino acids in bold originates from the vector.

Example 10. Vaccination Study

The objective of this study was to determine the level of protection conferred on vaccination with Intervacc's new multi-component subunit vaccine following intranasal challenge with wild type *S. equi* strain 4047 in Welsh Mountain ponies. The study has been performed by Animal Health Trust, UK. The vaccines used therein, which are designated Nordostrep Septavac or Nordostrep Pentavac A (or only Septavac or Pentavac) are disclosed below.

Methods

The ponies were initially randomised into 3 groups for the vaccination period.

TABLE 1

Vaccination groups.

| Group | Vaccine | No per group | Route |
|---|---|---|---|
| 1 | Nordostrep Septavac | 7 | IN + SC |
| 2 | Nordostrep Pentavac A | 7 | IN + SC |
| 3 | Placebo | 7 | IN + SC |

In the first trial groups 1 and 3 were taken through to challenge. (The challenge of second trial group 2 (Pentavac A) is described in section 9). The decision as to which vaccine group to challenge was taken by Intervacc one week prior to challenge.

The Nordostrep Pentavac A Formulation

The Pentavac vaccine consisted of the following five *S. equi* recombinant proteins: EAG, SclC, CNE, Eq5 and Eq8. For subcutaneous vaccination, the five proteins were mixed in PBS (50 μg/ml of the respective protein), divided in aliquots of 1 ml in vials and stored at −20° C. Immediately before vaccination, the vial was thawed and mixed with 1 ml adjuvant (Abisco 200, 375 μg/dose, Isconova AB, Sweden). For intranasal vaccination the five proteins were mixed in PBS (150 μg/ml of respective protein) and divided in aliquots of 2 ml in vials and stored at −20° C. Immediately before vaccination the vial was thawed and mixed with 2 ml adjuvant (Abisco 300, 500 μg/dose, Isconova AB, Sweden). In the placebo formulations the *S. equi* proteins were omitted. Thus, the placebo for subcutaneous vaccination only contained PBS and Abisco 200, 375 μg/dose and for intranasal vaccination, the placebo contained only PBS and Abisco 300, 500 μg/dose.

The Nordostrep Septavac Formulation

The Septavac vaccine consisted of the following seven *S. equi* recombinant proteins: EAG, SclC, CNE, Eq5, Eq8, IdeE and IdeE2. For subcutaneous vaccination, the seven proteins were mixed in PBS (50 µg/ml of respective protein) and divided in aliquots of 1 ml in vials and stored at −20° C. Immediately before vaccination the vial was thawed and mixed with 1 ml adjuvant (Abisco 200, 375 µg/dose, Isconova AB, Sweden). For intranasal vaccination, the seven proteins were mixed in PBS (150 µg/ml of the respective protein) and divided in aliquots of 2 ml in vials and stored at −20° C. Immediately before vaccination, the vial was thawed and mixed with 2 ml adjuvant (Abisco 300, 500 µg/dose, Isconova AB, Sweden). in the placebo formulations, the *S. equi* proteins were omitted. Thus, the placebo for subcutaneous vaccination only contained PBS and Abisco 200, 375 µg/dose, and for intranasal vaccination, it only contained PBS and Abisco 300, 500 µg/dose.

In these formulations, EAG is comprised of the fragment EAG4B and CNE is the fragment designated 2.16.

SHORT SUMMARY OF RESULTS

This study evaluated the efficacy of a new multi-component subunit vaccine for the prevention of strangles. The Septavac vaccine induced pyrexia in ponies for one day after first and second vaccinations. However, there were no other adverse reactions and this vaccine appears to be very well tolerated.

All ponies were challenged with an identical dose of $1 \times 10^8$ cfu of *S. equi* strain 4047, which was split and administered via both nostrils. All seven control ponies developed pyrexia and multiple lymph node abscesses (100%). Only one vaccinated pony developed pyrexia (which could have been due to an ongoing *S. zooepidemicus* infection) and only one developed lymph node abscesses (14%). Statistically, vaccinated ponies were significantly protected from *S. equi* as measured by temperature, post mortem score, and fibrinogen and neutrophil levels.

Overall, the Septavac vaccine was a safe and effective vaccine for the prevention of strangles. However, the invention is not restricted to the Septavac and Pentavac vaccines which have been studied in this Example but many combinations of the present antigens/immunogens are possible candidates for use in vaccine compositions for prevention of strangles.

1 Procedure

Two earlier studies (WO 2004/032957 A1 and ref. 27) demonstrated that Intervacc vaccines conferred some protection against *S. equi* challenge. All four vaccinated groups across the two studies showed reduced guttural pouch empyema. The present study was designed to compare the immunogenicity of two Nordvacc vaccines: one containing five (Pentavac) and one containing seven (Septavac) *S. equi* proteins.

Blood and nasal wash samples were taken according to the protocol to determine the equine immune responses to the vaccine subunits. Based on immunogenicity data, one vaccinated group was challenged to quantify the level of protection conferred.

Each pony was challenged with a total challenge dose of $1 \times 10^8$ cfu of *S. equi* strain 4047 administered via the spraying of a 2 ml culture containing $5 \times 10^7$ cfu into both nostrils. This dose regime is believed to optimise the infection rate whilst avoiding overwhelming the host immune response.

Ponies were carefully monitored for the onset of clinical signs of disease over a period of three weeks post challenge by regular checks, daily physical examination, monitoring of body temperature, the taking of sera to determine seroconversion and the taking of nasal washes for bacteriological analysis. All ponies were subjected to post mortem examination following abscessation or reaching the study endpoint at 3 weeks post challenge to determine the severity of disease pathology according to a scoring system developed at the AHT. Histopathological examination of tissues recovered from the study ponies was used to identify early signs of *S. equi* infection that were not obvious on post mortem (PM) examination.

TABLE 2

Sampling Schedule

| Day of study | Day of week | date | procedure | Volume of sera to be taken | Sample/Analysis/comment |
|---|---|---|---|---|---|
| day −10 | Thurs | 31 Jan. 2008 | veterinary examination | | |
| day 1 | Mon | 11 Feb. 2008 | Obs/temps, NW, BL | 40 ml normal, 20 ml EDTA | IgG and CFU from NW; ELISA for IgG from sera |
| day 2 | Tues | 12 Feb. 2008 | Obs/temps | | |
| day 3 | Wed | 13 Feb. 2008 | Obs/temps | | |
| day 4 | Thurs | 14 Feb. 2008 | Obs/temps, V1 | | 7 contr and 7 vaccinated |
| day 5 to 18 | Fri | 15 Feb. 2008 to 28 Feb. 2008 | Obs/temps | | |
| day 50 | Mon | 31 Mar. 2008 | Obs/temps, NW, BL | 20 ml normal | IgG and CFU from NW; ELISA for IgG from sera |
| day 51 | Tues | 01 Apr. 2008 | Obs/temps | | |
| day 52 to 59 | Wed | 02 Apr. 2008 to 09 Apr. 2008 | Obs/temps | | |
| day 60 | Thurs | 10 Apr. 2008 | Obs/temps, V2 | | 7 contr and 7 vaccinated |
| day 61 to 68 | Fri | 11 Apr. 2008 to 18 Apr. 2008 | Obs/temps | | |
| day 71 | Mon | 21 Apr. 2008 | Obs/temps, NW, BL | 20 ml normal | IgG and CFU from NW; ELISA for IgG from sera |
| day 72 | Tues | 22 Apr. 2008 | Obs/temps | | |
| day 73 | Wed | 23 Apr. 2008 | Obs/temps | | |
| day 74 | Thurs | 24 Apr. 2008 | Obs/temps, V3 | | 7 contr and 7 vaccinated |
| day 75 to 81 | Fri | 25 Apr. 2008 to 2 May 2008 | Obs/temps | | |

TABLE 2-continued

Sampling Schedule

| Day of study | Day of week | date | procedure | Volume of sera to be taken | Sample/Analysis/comment |
|---|---|---|---|---|---|
| day 86 | Tues | 06 May 2008 | Obs/temps, NW, BL | 40 ml normal, 20 ml EDTA | IgG and CFU from NW; ELISA for IgG from sera; fibrinogen and neutrophil levels to be quantified Move to Allen Centre |
| day 87 | Wed | 07 May 2008 | Obs/temps | | |
| day 88 | Thurs | 08 May 2008 | Obs/temps, Challenge | | |
| day 89 | Fri | 09 May 2008 | Obs/temps, NW, BL | 20 ml normal, 10 ml EDTA | IgG and CFU from NW; ELISA for IgG from sera; fibrinogen and neutrophil levels to be quantified |
| day 90 | Sat | 10 May 2008 | Obs/temps | | |
| day 91 | Sun | 11 May 2008 | Obs/temps | | |
| day 92 | Mon | 12 May 2008 | Obs/temps, NW, BL | 20 ml normal, 10 ml EDTA | IgG and CFU from NW; ELISA for IgG from sera; fibrinogen and neutrophil levels to be quantified |
| day 93 | Tues | 13 May 2008 | Obs/temps | | |
| day 94 | Wed | 14 May 2008 | Obs/temps, NW, BL | 20 ml normal, 10 ml EDTA | IgG and CFU from NW; ELISA for IgG from sera; fibrinogen and neutrophil levels to be quantified |
| day 95 | Thurs | 15 May 2008 | Obs/temps | | |
| day 96 | Fri | 16 May 2008 | Obs/temps, NW, BL | 20 ml normal, 10 ml EDTA | IgG and CFU from NW; ELISA for IgG from sera; fibrinogen and neutrophil levels to be quantified |
| day 97 | Sat | 17 May 2008 | Obs/temps | | |
| day 98 | Sun | 18 May 2008 | Obs/temps | | |
| day 99 | Mon | 19 May 2008 | Obs/temps, NW, BL | 20 ml normal, 10 ml EDTA | IgG and CFU from NW; ELISA for IgG from sera; fibrinogen and neutrophil levels to be quantified |
| day 100 | Tues | 20 May 2008 | Obs/temps | | |
| day 101 | Wed | 21 May 2008 | Obs/temps, NW, BL | 20 ml normal, 10 ml EDTA | IgG and CFU from NW; ELISA for IgG from sera; fibrinogen and neutrophil levels to be quantified |
| day 102 | Thurs | 22 May 2008 | Obs/temps | | |
| day 103 | Fri | 23 May 2008 | Obs/temps, NW, BL | 20 ml normal, 10 ml EDTA | IgG and CFU from NW; ELISA for IgG from sera; fibrinogen and neutrophil levels to be quantified |
| day 104 | Sat | 24 May 2008 | Obs/temps | | |
| day 105 | Sun | 25 May 2008 | Obs/temps | | |
| day 106 | Mon | 26 May 2008 | Obs/temps, NW, BL | 30 ml | IgG and CFU from NW; ELISA for IgG from sera; fibrinogen and neutrophil levels to be quantified |
| day 107 | Tues | 27 May 2008 | Obs/temps | | |
| day 108 | Wed | 28 May 2008 | Obs/temps, NW, BL | 30 ml | IgG and CFU from NW; ELISA for IgG from sera; fibrinogen and neutrophil levels to be quantified |
| day 109 | Thurs | 29 May 2008 | Obs/temps | | |

Comments:
NW = Nasal washings
BL = Blood sample
1. Nasal immunisation in both nostrils at all three occasions (2 × 2 ml in each nostril = 4 ml/vaccination)
2. Subcutaneous immunisation near submandibular lymph nodes (1 ml)
3. Two groups of seven (7) horses will be vaccinated and seven (7) unvaccinated/controls
4. IgG in sera analysed by Intervacc AS; IgG in NW by AHT (7 antigens)

2.1 Vaccine

Nordostrep Vaccines for Horses

Group 1; 7 ponies vaccinated with Nordostrep Pentavac A
  2 ml subcutaneous injection (1 ml on each side of the head)
  4 ml intranasal injection (2 ml in each nostril)
  Day 4; 60; 74

Group 2: 7 ponies vaccinated with Nordostrep Septavac
  2 ml subcutaneous injection (1 ml on each side of the head)
  4 ml intranasal injection (2 ml in each nostril)
  Day 4; 60; 74

Group 3: 7 ponies vaccinated with Placebo
  2 ml subcutaneous injection (1 ml on each side of the head)
  4 ml intranasal injection (2 ml in each nostril)
  Day 4; 60; 74

The vaccine vials were received by the AHT prior to the first vaccination and stored at −20° C. until use in freezer number EQ No. 2305. Placebo (containing no antigens) and adjuvant vials were stored at 4° C. until use in fridge number EQ No, 44.

At the time of vaccination, vaccines and adjuvants were mixed as stated in the protocol in situ by A Waller, L Prowse or C Robinson at AHT.

2.2 Challenge Bacterium

S. equi 4047 was prepared from fresh plates as described in SOP/BACT/25.

The bacteria grew as expected and the 1:40 diluted culture was harvested when the $OD_{600nm}$ reached 0.3. The growth of the challenge inoculum is shown in FIG. 6. The following results were obtained.

| Plating results: $1/10^5$ dilution |
|---|
| 37 colonies |
| 35 colonies |
| 33 colonies |
| 32 colonies |

$$\text{Mean} = 34.25 \text{ in } 100 \ \mu l = 4 \times 34.25 \times 10^5 \times 10$$

$$\text{Therefore actual dose per pony} = 1.37 \times 10^8 \text{ cfu/dose}$$

3 Animal Management
3.1 Supply
Twenty one Welsh Mountain ponies originally supplied by Mr Beedles, Shropshire, UK, were used. Ponies were approximately 8 months of age at the time of the first vaccination.
3.2 Identification/Allocation
Ponies were identified by a microchip in the neck. The 21 ponies were randomly assigned to vaccination groups (Table 3).

TABLE 3

Vaccination groups and pony chip IDs

| Group | Vaccine | Pony Chip ID's |
|---|---|---|
| 1 | Septavac | 00012, 00159, 00833, 00976, 99123, 99668, 99794 |
| 2 | Pentavac | 01298, 01605, 01724, 99223, 99229, 99773, 99919 |
| 3 | Placebo | 00173, 00427, 01635, 02078, 99549, 99776, 99886 |

3.3 Husbandry
Prior to challenge, ponies were kept at pasture on grass at Lanwades Park, Kentford, UK and Kiting, Newmarket, UK. These sites have been approved by the Home Office for this type of work. Drinking water was available ad libitum.
Ponies in groups 1 and 3 were transferred to the ACVS (Allen Centre), three days prior to challenge to allow acclimatisation. Ponies were separated into two animal rooms according to their vaccination groups, so that ponies from each vaccination group were kept together.
4 Methods
4.1 Vaccination
Vaccinations were given by subcutaneous injection near the retropharyngeal lymph nodes according to AHT SOP/EQU/03 or via intranasal spray according to AHT SOP/EQU/07.
4.1.2 Preliminary Clinical Examination
A veterinarian clinically examined all ponies before the first vaccination, before V2 (due to S. zoo infection) and before V3. Only healthy ponies in good clinical condition were included in the study (SOP/EQU/08).
4.1.3 Vaccination
Ponies received vaccinations according to Table 4. With the exception that pony 9229 was pyrexic on 14/02/08 due to an ongoing S. zooepidemicus infection. This pony recovered over the weekend and was vaccinated on 18/04/08.

TABLE 4

Vaccination routes and dates

| Group | Vaccine | V1 | V2* | V3* |
|---|---|---|---|---|
| A | Septavac | 14 Feb. 2008 | 10 Apr. 2008 | 24 Apr. 2008 |
| B | Pentavac | 14 Feb. 2008 | 10 Apr. 2008 | 24 Apr. 2008 |
| C | Placebo | 14 Feb. 2008 | 10 Apr. 2008 | 24 Apr. 2008 |

*Delayed by 7 days due to S. zooepidemicus infection.

4.1.4 Clinical Observations Around Vaccinations
Clinical observations were performed daily after vaccination. If adverse reactions occurred, then additional checks were made as required.
4.2 Experimental Challenge with S. equi 4047
4.2.1 Preliminary Clinical Examination
Prior to transfer to the ACVS, a veterinarian clinically examined the challenge ponies. Only healthy ponies in good clinical condition were subjected to the challenge.
4.2.2 Challenge
Two weeks after the third vaccination (08/05/08), each pony was challenged by intranasal administration of 2 ml of a fresh S. equi 4047 culture into both nostrils using a flexible tube and spray nozzle according to AHT SOP/BACT32. Such a challenge dose was predicted to contain a total of $1 \times 10^8$ cfu of S. equi 4047.
No problems were encountered during the administration of the challenge dose. Spare inocula were used to quantify the actual challenge dose administered, which was found to be $1.37 \times 10^8$ cfu/dose.
4.3 Post Challenge Monitoring
4.3.1 Clinical Examination
Ponies were examined according to AHT SOP/EQU/02. Each pony was examined clinically on the day of challenge, and on each of the following 21 days for the occurrence of symptoms associated with S. equi infection (demeanor, nasal discharge, lymph node swelling and abscessation, signs of coughing, difficulty swallowing and feeding, and ocular signs).
4.3.2 Rectal Temperatures
Individual rectal temperatures were taken at around 9.00 am from the day of challenge through to day 21 after challenge.
4.4 Blood Sampling
Blood samples were taken from the jugular vein according to AHT SOP/EQU/01 and according to the study protocol schedule. Serum was prepared according to AHT SOP/EQU/01 and stored frozen at −20° C. or below until use.
4.5 Processing of Blood Samples
Processing of blood samples was carried out by Leah Prowse under the responsibility of Andrew Waller at the Animal Health Trust.
4.6 Processing of Nasal Wash Samples
Individual nasal washes were taken according to AHT SOP/EQU/02 as stated in the study protocol schedule. A 500 μl sample of the nasal wash was added to 500 μl of Todd-Hewitt Broth in situ at the time of sampling for transportation to the lab to allow quantification of the number of β-haemolytic streptococci per ml according to AHT SOP/BACT/02. The remaining nasal wash sample was centrifuged and the supernatant decanted into a clean 5 ml polypropylene tube and stored at −70° C. until use for quantification of mucosal antibodies.
4.7 Post Mortem Examination
Provision was made for a complete post mortem examination to be carried out by the Animal Health Trust on all ponies following euthanasia as a result of abscessation or on reaching the study end point 21 days post challenge.
Tissue samples were preserved in phosphate buffered formalin and subjected to microscopic examination according to standard techniques and provision of a full and formal report. Tissue swabs were taken and the results recorded and used to evaluate the level of S. equi infection. Charcoal swabs were taken from each of the areas as stated in the protocol and processed on COBA Streptococcal selective plates to determine the presence of *S. equi*.

Strangles pathology was scored using the system in Table 5.

TABLE 5

Pathology scoring system

| Pathology | Score |
|---|---|
| Retropharyngeal or submandibular lymph node abscess: | 15 |
| Retropharyngeal or submandibular lymph node microabscess: | 10 |
| Empyaema of guttural pouch: | 5 |
| Scarring of guttural pouch: | 5 |
| Enlarged lymph node: | 1 |
| Follicular hyperplasia of guttural pouch: | 1 |

4.8 Histopathological examination

Tissue samples taken from ponies at post mortem examination were fixed in formalin, cut into sections and sent to Professor Ken Smith at the Royal Veterinary College for analysis. Professor Smith prepared a report for the samples from each pony and his observations were scored according to Table 6.

TABLE 6

Histopathology scoring system

| Histopathology | Score |
|---|---|
| Rhinitis | 1 |
| Lymphadenitis | 1 |
| Pharyngitis | 1 |
| Lymph node abscessation | 5 |
| Guttural pouch empyema | 5 |

Deviations

The study was performed in accordance with the study protocol no. 08.0001.P and subsequent amendments, with the following deviations from the agreed study protocol:

Pony 9229 was pyrexic on 14/02/08 due to an ongoing *S. zooepidemicus* infection. This pony recovered over the weekend and was vaccinated on 18/04/08.

Date of V2 delayed 7 days due to *S. zoo* infection in 45% of ponies. This had a knock on effect on V3 and challenge which were also delayed 7 days.

A delay of one day occurred on sampling ponies due to staff shortages. Ponies due to be sampled on day 85 were actually sampled on day 86.

20 ml of EDTA blood was taken on day 86 instead of 10 ml to enable purification of the ponies' DNA for archiving.

Nordvacc decided to retain the unchallenged Pentavac group (2) for a 6-month period to monitor the duration of antibody response.

6 Fate of Ponies at the End of the Study

All ponies in groups 1 and 3 were euthanased and subjected to post mortem examination. Ponies in group 2 were retained for 6 months to monitor the duration of antibody responses.

7 Archiving

The raw data have been archived by Animal Health Trust, Lanwades Park, Kentford, Newmarket, Suffolk, CB8 7UU.

8 Summary of Results 8.1 Responses Following the First and Second Vaccinations 8.1.1 Clinical Responses All ponies responded well to first vaccination. No injection site reactions were observed in any of the groups. However, a rise in rectal temperature was observed in the vaccinated groups (FIG. 7). This was most pronounced in the Septavac group with 4 of 7 ponies developing pyrexia (temperature>38.9° C.) one day post V1 and 5 of 7 ponies developing pyrexia one day post V2. In comparison, 2 of 7 ponies of the Pentavac group and none of the controls were pyrexic post V1, and 3 ponies of the Pentavac group and no controls were pyrexic post V2. Interestingly, only 1 Septavac, 2 Pentavac and 1 control pony developed pyrexia post V3. This could be due to the high level of antibodies induced post V2, which may have neutralized the antigens in the vaccine more effectively.

There were no obvious differences in nasal score (FIG. 8), lymph node score (FIG. 9) or *S. zooepidemicus* counts (FIG. 10) between the study groups during the vaccination phase, with the exception of some ponies that had ongoing *S. zooepidemicus* infections typical of ponies of this age. This resulted in a rise in mean rectal temperature around the original date for V2 (Mar. 4, 20008) as demonstrated in FIG. 7. Ponies were allowed to recover from this *S. zooepidemicus* infection and all ponies were vaccinated on Oct. 4, 2008.

8.2 Responses Following Challenge

The preparation and conduct of both challenges went extremely well and all ponies received the required dose of *S. equi* without incident on the Aug. 5, 2008.

Earliest onset of pyrexia was at day 4 post challenge in control pony 2078. Two more ponies developed pyrexia on day 5, another on day 6 and 7 and the final control pony developed pyrexia on day 10 (FIG. 11). The mean number of days that control ponies were pyrexic was 4.2 days compared with 0.7 days for vaccinated ponies (Table 7). However, it should be noted that control ponies were euthanased on welfare grounds from day 8 post challenge and all control ponies had been euthanased by day 13 post challenge. This has had a knock on effect on the mean temperatures, observation scores, fibrinogen and neutrophil levels and observation scores for control ponies, which decline as ponies succumbing to *S. equi* infection were euthanased.

Overall, there was a significant difference in the mean temperatures of the two groups from day 5 to day 11 post challenge (FIG. 11). Of the Septavac ponies only pony 0976 developed pyrexia on day 8 (Table 7). However, this may have been due to the ongoing *S. zooepidemicus* infection that was evident in this pony.

Fibrinogen levels were significantly different between the two study groups on days 6, 8 and 11 post challenge (FIG. 12). All controls developed elevated fibrinogen levels, but only 2 vaccinates (ponies 0976 and 9794) had higher levels.

Neutrophil levels were also significantly different between the two study groups on days 6, 8 and 11 post challenge (FIG. 13). All controls developed elevated neutrophil levels, but only 1 vaccinate (pony 9794) had higher levels.

There was an increased level of submandibular lymph node swelling in control ponies, although this did not appear to be statistically significant (FIG. 14). There were no differences in nasal discharge (FIG. 15) or *S. zooepidemicus* counts (FIG. 16) between the study groups.

On post mortem examination, all controls were found to have multiple lymph node abscesses, while only one vaccinated pony, 9794, was found to have lymph node abscesses (Tables 8 and 9). Overall the mean pathology score for controls and 11.7, respectively indicating that a significant level of protection had been induced by the Septavac vaccine (FIG. 17). *S. equi* was isolated from the lymph nodes of all control ponies, but only 2 vaccinates (0976 and 9794) (Table 10). These findings were strengthened by histopathological examination, which confirmed that only one Septavac pony had developed abscesses in at least two of their lymph nodes (Table 11 and FIG. 18).

Furthermore, the IgG levels in nasal washings and serum samples of the septavac group were measured using ELISA (FIGS. 19 and 20) showing that the antigens generate mucosal and serum antibodies.

TABLE 7

Number of days pyrexic after challenge

| Group | Pony ID | Number of days |
|---|---|---|
| Septavac | 0012 | 0 |
| Septavac | 0159 | 0 |
| Septavac | 0833 | 0 |
| Septavac | 0976 | 5 |
| Septavac | 9123 | 0 |
| Septavac | 9668 | 0 |
| Septavac | 9794 | 0 |
| Control | 0173 | 2 |
| Control | 0427 | 4 |
| Control | 1635 | 5 |
| Control | 2078 | 4 |
| Control | 9549 | 4 |
| Control | 9776 | 5 |
| Control | 9886 | 6 |

Mean Septavac = 0.7 days
Mean control = 4.2 days*
*All control ponies were euthanased by day 13 post-challenge, but most would have continued to have elevated temperatures had they not been euthanased on welfare grounds.

TABLE 8

Post Mortem Analysis after Challenge

| Group | Pony ID | Total PM score |
|---|---|---|
| Septavac | 0012 | 6 |
| Septavac | 0159 | 3 |
| Septavac | 0833 | 5 |
| Septavac | 0976 | 6 |
| Septavac | 9123 | 4 |
| Septavac | 9668 | 1 |
| Septavac | 9794 | 57 |
| Control | 0173 | 42 |
| Control | 0427 | 53 |
| Control | 1635 | 66 |
| Control | 2078 | 49 |
| Control | 9549 | 57 |
| Control | 9776 | 43 |
| Control | 9886 | 42 |

TABLE 9

Number and Location of Abscesses on Post Mortem

| | | SMLN | | RPLN | |
|---|---|---|---|---|---|
| Group | Pony ID | L | R | L | R |
| Septavac | 0012 | — | — | — | — |
| Septavac | 0159 | — | — | — | — |
| Septavac | 0833 | — | — | — | — |
| Septavac | 0976 | — | — | — | — |
| Septavac | 9123 | — | — | — | — |
| Septavac | 9668 | — | — | — | — |
| Septavac | 9794 | — | ✓ | ✓ | ✓ |
| Control | 0173 | — | — | ✓ | ✓ |
| Control | 0427 | ✓ | — | ✓ | ✓ |
| Control | 1635 | ✓ | ✓ | ✓ | ✓ |
| Control | 2078 | — | ✓ | ✓ | ✓ |
| Control | 9549 | ✓ | — | ✓ | ✓ |
| Control | 9776 | — | — | ✓ | ✓ |
| Control | 9886 | — | — | ✓ | ✓ |

SMLN—Submandibular Lymph Node
RPLN—Retropharyngeal Lymph Node
✓ = abscess

TABLE 10

*S. equi* Counts Found in the Lymph Nodes on Post Mortem

| Pony ID | SMLN L | SMLN R | RPLN L | RPLN R | Cervical LN | Tracheal/ Broncheal LN | *S. equi* Confirmed by sugar test |
|---|---|---|---|---|---|---|---|
| 0012 | — | — | — | — | — | — | — |
| 0159 | — | — | — | — | — | — | — |
| 0833 | — | — | — | — | — | — | — |
| 0976 | — | Sparse | — | — | — | — | Yes |
| 9123 | — | — | — | — | — | — | — |
| 9668 | — | — | — | — | — | — | — |
| 9794 | — | Con | Con | Con | — | — | Yes |
| 0173 | Sparse | Sparse | Con | Con | — | — | Yes |
| 0427 | Con | Con | Con | Con | — | — | Yes |
| 1635 | Con | Con | Con | Con | — | — | Yes |
| 2078 | Con | Con | Con | Con | Con | — | Yes |
| 9549 | Con | Con | Con | Con | — | — | Yes |
| 9776 | Sparse | Sparse | Con | Con | — | — | Yes |
| 9886 | — | Sparse | Con | Con | — | — | Yes |

Ponies 0833 and 0159 showed sparse *S. equi* in areas other than the lymph node. Ponies 0012, 9123 and 9668 showed no *S. equi*.
Con—confluent
SMLN—Submandibular Lymph Node
RPLN—Retropharyngeal Lymph Node

TABLE 11

Histopathology Scores

| Pony Chip ID | 0012 | 0159 | 0833 | 0976 | 9123 | 9668 | 9794 | 0173 | 0427 | 1635 | 2078 | 9549 | 9776 | 9886 |
|---|---|---|---|---|---|---|---|---|---|---|---|---|---|---|
| Identity | Sep | Sep | Sep | Sep | Sep | Sep | Sep | Con | Con | Con | Con | Con | Con | Con |
| Nasal turbinate | 0 | 1 | 1 | 0 | 0 | 0 | 0 | 0 | 0 | 0 | 0 | 0 | 1 | 0 |
| Nasopharynx | 0 | 0 | 0 | 1 | 0 | 0 | 0 | 0 | 0 | 0 | 0 | 0 | 0 | 0 |
| SMLN - L | 0 | 0 | 0 | 0 | 0 | 0 | 0 | 0 | 5 | 5 | 0 | 5 | 0 | 0 |
| SMLN - R | 0 | 0 | 0 | 0 | 0 | 0 | 5 | 0 | 5 | 5 | 5 | 0 | 0 | 0 |
| RPLN - L | 0 | 0 | 0 | 1 | 0 | 0 | 5 | 5 | 5 | 5 | 5 | 5 | 5 | 5 |
| RPLN - R | 0 | 0 | 0 | 1 | 0 | 0 | 5 | 5 | 5 | 5 | 5 | 5 | 5 | 5 |

TABLE 11-continued

Histopathology Scores

| Pony Chip ID | 0012 | 0159 | 0833 | 0976 | 9123 | 9668 | 9794 | 0173 | 0427 | 1635 | 2078 | 9549 | 9776 | 9886 |
|---|---|---|---|---|---|---|---|---|---|---|---|---|---|---|
| Gut pouch - L | 5 | 5 | 0 | 0 | 0 | 0 | 5 | 5 | 5 | 5 | 5 | 5 | 5 | 5 |
| Gut pouch - R | 5 | 0 | 0 | 0 | 0 | 0 | 5 | 5 | 5 | 5 | 5 | 5 | 5 | 5 |
| Lung | 0 | 0 | 0 | 0 | 0 | 0 | 0 | 0 | 0 | 0 | 0 | 0 | 0 | 0 |
| Brain | 0 | 0 | 0 | 0 | 0 | 0 | 0 | 0 | 0 | 0 | 0 | 0 | 0 | 0 |
| TOTAL | 10 | 6 | 1 | 3 | 0 | 0 | 25 | 20 | 30 | 30 | 25 | 25 | 21 | 20 |

Rhinitis: 1
Pharyngitis: 1
Lymphadenitis: 1
Lymph node abscessation: 5
Guttural pouch empyaema: 5
Sep = Septavac
Con = Control

9. Pentavac A Vaccination Study

In the second trial the seven horses of group 2 (section 3.2, table 3) where after vaccination V3 (Table 4) kept at pasture on grass and blood samples where taken regularly to measure IgG antibody titers in ELISA against the five antigens present in the Pentavac A formulation (FIG. 21). In Day 270 (Nov. 6, 2008) a booster dose of Pentavac A was given according to the procedure described in section 4.1. Before challenge the group was transferred to ACVS and fourteen days post booster the group was experimentally challenged with *S. equi* 4047 as described in section 4.2 and monitored essentially as described in section 4.3.

9.1 Brief Summary of the Pentavac A Vaccination Study

The Pentavac A study revealed that after vaccination a significant antibody response against the individual antigens remains for at least six months (FIG. 21).

The Pentavac A vaccine delayed the onset of infection upon challenge with *S. equi* and that one of the ponies in the group did not developed strangles.

Further Applications

One implication of the present invention is that enzymes degrading immunoglobulins can be used as antigens in a vaccine to protect the target animal from infection. Therefore one embodiment of the present invention is that concerning the human pathogenic group A streptococci (GAS) it is possible to construct a vaccine composition which protects humans from infections caused by this bacterium. In strains of GAS there are several reported extracellular immunoglobulin degrading proteins (called Sib35, IdeS or Mac-proteins) which share amino acid sequence homologies to IdeE and IdeE2 and therefore in light of the present invention can be purified and used as antigens in a vaccine separately or in combination with other purified extracellular proteins (like M-proteins or M-like proteins or fragments thereof) from group A strains. As in the present invention another implication is that the invention can be used to develop specific antisera, polyclonal or monoclonal antibodies to be used for diagnostic purposes or to be used in passive immunisations of the target animal including humans.

REFERENCES

1. Courtney, H. S., Y. Li, J. B. Dale, and D. L. Hasty. 1994. Cloning, sequencing and expression of a fibronectin/fibrinogen-binding protein from group A streptococci. Infect. Immun. 62:3937-3946.
2. Cue, D., P. E. Dombek, H. Lam, and P. P. Cleary. 1998. *Streptococcus pyogenes* serotype M1 encodes multiple pathways for entry into human epithelial cells. Infect. Immun, 66:4593-4601.
3. Barnham, M., A. Ljunggren, and M. McIntyre. 1987. Human infection with *Streptococcus zooepidemicus* (Lancefield group C): three case reports. Epidem. Inf. 98: 183-190.
4. Galán, J. E., and J. F. Timoney. 1988. Immunologic and genetic comparison of *Streptococcus equi* isolates from the United States and Europe. J. Clin. Microbiol. 26:1142-1146.
5. Flock, M., Jacobsson, K., Frykberg, L., Hirst, T., R., Franklin, A., Guss, B. and Flock, J.-I. (2004) Infect Immun 72:3228-3236.
6. Engvall, E., E. Ruoslahti, and J. M. Miller. 1978. Affinity of fibronectin to collagen of different genetic types and to fibronogen. J. Exp. Med. 147:1584-1595.
7. Patti, J. M., Jonsson, H., Guss, B., Switalski, L. M., Wiberg, K., Lindberg, M., and Hook, M. (1992) Molecular characterization and expression of a gene encoding a *Staphylococcus aureus* collagen adhesin. *J. Biol. Chem.* 267:4766-4772.
8. Jonsson, H., Lindmark, H., and Guss. B. (1995) A protein G related cell surface protein in *Streptococcus zooepidemicus*. Infect Immun 63:2968-2975.
9. Lindmark, H., Jacobsson, K., Frykberg, L., and Guss, B. (1996) Fibronectin-binding protein of *Streptococcus equi* subspecies *zooepidemicus*. Infect Immun 64:3993-3999.
10. Jacobsson, K., Jonsson, H., Lindmark, H., Guss, B., Lindberg, M., and Frykberg. L. (1997) Shot-gun phage display mapping of two streptococcal cell-surface proteins. *Microbiol Res.* 152:1-8.
11. Lindmark, H., Jonsson, P., Olsson-Engvall, E., and Guss, B. (1999) Pulsed-field gel electrophoresis and distribution of the genes zag and fnz in isolates of *Streptococcus equi*. Res Vet Sci. 66:93-99.
12. Lindmark, H., and Guss, B. (1999) SFS, a novel fibronectin-binding protein from *Streptococcus equi*, inhibits the binding between fibronectin and collagen. Infect. Immun. 67: 2383-2388.
13. Lindmark, H. (1999) Characterization of adhesive extracellular proteins from *Streptococcus equi*. (Doctoral thesis) Acta Universitatis Agriculturae Sueciae, Agraria 139. ISBN 91-576-5488-3.
14. Lindmark, H., Nilsson, M., and Guss, B. (2001) Comparison of the fibronectin-binding protein FNE from *Streptococcus equi* subspecies *equi* with FNZ from *S. equi* subspecies *zooepidemicus* reveals a major and conserved difference. 69: 3159-3163.
15. Schneewind, O., Fowler, A. and Faull, K. F. (1995) Structure of the cell wall anchor of surface proteins in *Staphylococcus aureus*. Science 268:103-106, 16. Anton Mayr et al. Handbuch der Shutzmpfungen in der Tiermedizin. 3.3.4. p. 196-200. Verlag Paul Parey. Berlin and Hamburg. 11984
17. Elson, C. O., and M. T. Dertzbaugh. 1999. p. 817-838, Nucosal immunology, 2$^{nd}$ ed. Of Academic Press, New York, N.Y.
18. Winner et al. 1991. Infect. Immun. 59:997-982
19. Ogra et al. Clinical Microbiology Reviews, April 2002, p. 430-445.
20. B. Morein and Karin Lövgren Bengtsson 1998, 76:295-299. Immunology and Cellbiology
21. Hanski, E., and M. G. Caparon. 1992. Protein F, a fibonectin-binding protein, is an adhesin of the group A streptococcus *Streptococcus pyogenes*. Proc. Natl. Acad. Sci. USA 89:6172-6176.
22. Hanski, E., P. A. Horwitz, and M. G. Caparon. 1992. Expression of protein F, the Fibronectin-binding protein of *Streptococcus pyogenes* JRS4, in heterologous streptococcal and enterococcal strains promotes their adherence to respiratory epithelial cells. Infect. Immun. 60:5119-5125.
23. Jadoun, J., V. Ozeri, E. Burstein, E. Skuteisky, E. Hanski, and S. Sela. 1998. Protein F1 required for efficient entry of *Streptococcus pyogenes* into epithelial cells. J. Infect. Dis. 178:147-158.
24. Molinri, G., S. R. Talay, P. Valentin-Weigand, M. Rohde, and G. S. Chhatwal. 1997. The fibronectin-binding protein of *Streptococcus pyogenes* SfbI, is involved in the internalization of group A streptococci by epithelial cells, Infect. Immun. 65:1357-1363.
25. Lannergård, J., Frykberg, L. and Guss B. (2003) CNE, a collagen-binding protein of *Streptococcus equi*. FEMS Microbial. Lett. 222:69-74,
26. Lannergård, J. and Guss, B. (2006) FEMS Microbiol Lett 262: 230-235.
27. Waller, A., Flock, M., Smith, K., Robinson, C., Mitchell, Z., Karlström, A., Lannergård, J., Bergman, R., Guss, B. and Flock, J.-I. (2007) Vaccine 25: 3629-3635.
28. WO 92/07002
29. WO 00/37496
30. WO 2007/116059

The invention claimed is:

1. An antigenic composition comprising:
    a polypeptide which is designated EAG and comprises SEQ ID NO: 13;
    a polypeptide which is designated IdeE and comprises amino acids 6 to 320 in SEQ ID NO: 30, and
    a polypeptide which is designated IdeE2 and comprises amino acids 2 to 345 in SEQ ID NO: 2.

2. The antigenic composition of claim 1, which further comprises:
    a polypeptide designated CNE (or SEC), which comprises SEQ ID NO: 28;
    a polypeptide which is designated Eq5 and comprises amino acids 2 to 442 in SEQ ID NO: 4; and
    a polypeptide which is designated Eq8, which comprises amino acids 2 to 197 in SEQ ID NO: 6.

3. The antigenic composition of claim 1, wherein at least one polypeptide is recombinantly produced.

4. The antigenic composition of claim 1, wherein at least one polypeptide is an isolated or purified polypeptide.

5. The antigenic composition of claim 1, consisting of the polypeptides EAG comprising SEQ ID NO: 13, IdeE comprising amino acids 6 to 320 in SEQ ID NO: 30 and IdeE2 comprising amino acids 2 to 345 in SEQ ID NO: 2.

6. The antigenic composition of claim 1, consisting of the polypeptides EAG of comprising SEQ ID NO: 13, IdeE comprising amino acids 6 to 320 in SEQ ID NO: 30, IdeE2 comprising amino acids 2 to 345 in SEQ ID NO: 2, CNE having SEQ ID NO: 28, Eq5 comprising amino acids 2 to 442 in SEQ ID NO: 4 and Eq8 comprising amino acids 2 to 197 in SEQ ID NO: 6.

7. A vaccine composition for protecting non-human mammals against infection of *Streptococcus equi*, which comprises:
    an antigenic composition consisting of
    a polypeptide which is designated EAG and comprises SEQ ID NO: 13;
    a polypeptide which is designated IdeE and comprises amino acids 6 to 320 in SEQ ID NO: 30,
    a polypeptide which is designated IdeE2 and comprises amino acids 2 to 345 in SEQ ID NO: 2,
    a polypeptide designated CNE (or SEC), which comprises SEQ ID NO: 28;
    a polypeptide which is designated Eq5 and comprises amino acids 2 to 442 in SEQ ID NO: 4; and
    a polypeptide which is designated Eq8, which comprises amino acids 2 to 197 in SEQ ID NO: 6, as immunizing component; and
    a pharmaceutically acceptable carrier.

8. The vaccine composition of claim 7, which further comprises an adjuvant.

9. The vaccine composition of claim 7, which is provided in a physiologically administrable form.

10. The vaccine composition of claim 7, which is administrable by subcutaneous, intranasal or intramuscular inoculation.

\* \* \* \* \*

SEQUENCE LISTING

```
<160> NUMBER OF SEQ ID NOS: 33

<210> SEQ ID NO 1
<211> LENGTH: 385
<212> TYPE: PRT
<213> ORGANISM: Streptococcus equi

<400> SEQUENCE: 1

Met Met Lys Lys Gln Ser Phe Thr His Ser Arg Lys Pro Lys Phe Gly
1               5                   10                  15

Met Arg Lys Leu Ser Ile Gly Leu Ala Ser Cys Met Leu Gly Met Met
            20                  25                  30

Phe Leu Thr Thr Gly His Val Ser Gly Glu Val Val Glu Val Trp Pro
        35                  40                  45

Asn Gly Gln Asn Pro Asn Gly Lys Ile Glu Ile Leu Ser Gln Thr Glu
    50                  55                  60

His Ser Glu His Leu Gln Lys Leu Arg Asp Ile Glu Asp Phe Gln Ala
65                  70                  75                  80

Gln Lys Gln Ala Asp His Val Arg Tyr Thr Lys Trp Leu Asp Gly Val
                85                  90                  95

Thr Val Asp Glu His Glu Phe Arg Lys Ile Lys Glu Tyr Asp Thr Glu
            100                 105                 110

Tyr Tyr Val Thr Pro Leu Leu Ser Gly Lys Gly Tyr Tyr Asp Ile Asn
        115                 120                 125

Lys Asp Phe Asn Gln Asp Ser Asp Lys Cys Ala Ala Ala Val Ala Ala
    130                 135                 140

Asn Met Phe His Tyr Trp Phe Asp Arg Asn Arg Asp Ser Ile Asn Arg
145                 150                 155                 160

Phe Leu Ser Gln Ser Pro Gly Glu Asn Gly Val Ile Lys Leu Glu Asn
                165                 170                 175

Glu Lys Thr Ile Glu Val Ser Lys Phe Leu Glu Thr Tyr Arg Ser Asp
            180                 185                 190

Gly Asp Tyr Leu Asp Lys Ser Pro Phe Phe Asp Leu Ile Ser Asn Ser
        195                 200                 205

Phe Lys Gly Pro Val Trp Ala Asn Lys Leu Leu Asp Ala Tyr Ile Asn
    210                 215                 220
```

```
Gly Tyr Gly Tyr Ile His Lys Phe Ala Lys Asn Thr Pro His Ser Lys
225                 230                 235                 240

Asn Asn Asn Ser Lys Phe Asn Phe Phe Lys Lys Val Phe Asp Gly Asn
            245                 250                 255

Leu Leu Thr Asp Ile His Gln Ile Phe Asp Tyr Asn Thr Phe Ser Asp
        260                 265                 270

Lys Leu Ser Glu Ala Leu Tyr Thr Gly Lys Ala Ile Gly Leu Ala Tyr
    275                 280                 285

Gly Pro Gly Asp Leu Arg Arg Ser Leu Gly His Ile Ile Ser Val Trp
290                 295                 300

Gly Ala Asp Leu Asp Asp Gln Asn Arg Val Val Ala Ile Tyr Val Thr
305                 310                 315                 320

Asp Ser Asp Asp Lys Lys Leu Thr Ile Gly Asn Glu Arg Val Gly Leu
            325                 330                 335

Lys Arg Tyr Lys Val Ser Ser Asp Asp Gln Gly Arg Ala Arg Leu Thr
        340                 345                 350

Thr Arg Asp Lys Asp Asn Thr Gly Gly Glu Ile Arg Ser Ile Glu Thr
    355                 360                 365

Leu Asp Met Gly Thr Gln Glu Trp Ala Asp Tyr Phe Asn Lys Thr Glu
370                 375                 380

Lys
385

<210> SEQ ID NO 2
<211> LENGTH: 349
<212> TYPE: PRT
<213> ORGANISM: Artificial Sequence
<220> FEATURE:
<223> OTHER INFORMATION: Chemically synthesized Ide E2 protein having
      one N-terminal and four C-terminal amino acids originating from
      the pTYB4 vector

<400> SEQUENCE: 2

Met Glu Val Val Glu Val Trp Pro Asn Gly Gln Asn Pro Asn Gly Lys
1               5                   10                  15

Ile Glu Ile Leu Ser Gln Thr Glu His Ser Glu His Leu Gln Lys Leu
            20                  25                  30

Arg Asp Ile Glu Asp Phe Gln Ala Gln Lys Gln Ala Asp His Val Arg
        35                  40                  45

Tyr Thr Lys Trp Leu Asp Gly Val Thr Val Asp Glu His Glu Phe Arg
    50                  55                  60

Lys Ile Lys Glu Tyr Asp Thr Glu Tyr Tyr Val Thr Pro Leu Leu Ser
65                  70                  75                  80

Gly Lys Gly Tyr Tyr Asp Ile Asn Lys Asp Phe Asn Gln Asp Ser Asp
                85                  90                  95

Lys Cys Ala Ala Ala Val Ala Ala Asn Met Phe His Tyr Trp Phe Asp
            100                 105                 110

Arg Asn Arg Asp Ser Ile Asn Arg Phe Leu Ser Gln Ser Pro Gly Glu
        115                 120                 125

Asn Gly Val Ile Lys Leu Glu Asn Glu Lys Thr Ile Glu Val Ser Lys
    130                 135                 140

Phe Leu Glu Thr Tyr Arg Ser Asp Gly Asp Tyr Leu Asp Lys Ser Pro
145                 150                 155                 160

Phe Phe Asp Leu Ile Ser Asn Ser Phe Lys Gly Pro Val Trp Ala Asn
                165                 170                 175
```

```
Lys Leu Leu Asp Ala Tyr Ile Asn Gly Tyr Gly Tyr Ile His Lys Phe
            180                 185                 190

Ala Lys Asn Thr Pro His Ser Lys Asn Asn Ser Lys Phe Asn Phe
        195                 200                 205

Phe Lys Lys Val Phe Asp Gly Asn Leu Leu Thr Asp Ile His Gln Ile
    210                 215                 220

Phe Asp Tyr Asn Thr Phe Ser Asp Lys Leu Ser Glu Ala Leu Tyr Thr
225                 230                 235                 240

Gly Lys Ala Ile Gly Leu Ala Tyr Gly Pro Gly Asp Leu Arg Arg Ser
            245                 250                 255

Leu Gly His Ile Ile Ser Val Trp Gly Ala Asp Leu Asp Gln Asn
            260                 265                 270

Arg Val Val Ala Ile Tyr Val Thr Asp Ser Asp Asp Lys Lys Leu Thr
        275                 280                 285

Ile Gly Asn Glu Arg Val Gly Leu Lys Arg Tyr Lys Val Ser Ser Asp
    290                 295                 300

Asp Gln Gly Arg Ala Arg Leu Thr Thr Arg Asp Lys Asp Asn Thr Gly
305                 310                 315                 320

Gly Glu Ile Arg Ser Ile Glu Thr Leu Asp Met Gly Thr Gln Glu Trp
            325                 330                 335

Ala Asp Tyr Phe Asn Lys Thr Glu Lys Leu Glu Pro Gly
            340                 345

<210> SEQ ID NO 3
<211> LENGTH: 608
<212> TYPE: PRT
<213> ORGANISM: Streptococcus equi

<400> SEQUENCE: 3

Met Lys Lys Phe Thr Lys Arg Cys Leu Lys Gly Cys Gly Leu Val Gly
1               5                   10                  15

Leu Val Phe Ser Thr Gly Leu Val Ala Leu Ser Asp Asn Ile Asp Ser
            20                  25                  30

Ala Leu Thr Val Gly Ala Glu Thr Thr Ala Ser Ala Phe Glu Asn
        35                  40                  45

Asn Gly Thr Gly Gln His Leu Asn Trp His Ile Asp Ile Pro Gln Glu
    50                  55                  60

Tyr Thr Val Glu Leu Gly Glu Pro Ile Thr Ile Ser Asp Leu Met Ser
65                  70                  75                  80

Gln Ile Thr Val Thr Arg Lys Gly Ser Asn Gly Thr Val Asn Asp Gly
            85                  90                  95

Asp Thr Phe Asp Phe Ile Ser Asn Gly Asp Gly Ser Arg Gly Ile Asp
        100                 105                 110

Thr Pro Gly Val Lys Ile Trp Phe Asp Phe Tyr Asn Ala Ala Gly Thr
    115                 120                 125

Ser Phe Leu Thr Asp Glu Met Leu Ala Ser Pro Thr Tyr Ala Val Pro
130                 135                 140

Gly Gly Ser Tyr Thr Ile Lys Ala Trp Val Phe Tyr Gly Lys Asn Asp
145                 150                 155                 160

Thr Lys Lys Leu Phe Thr Phe Lys Leu Lys Asn Ser Asn Ser Asn Lys
            165                 170                 175

Thr Glu Leu Arg Lys Ser Leu Glu Glu Ala Lys Leu Lys Leu Ser Gln
        180                 185                 190
```

```
Pro Glu Gly Thr Tyr Ser Asp Glu Ser Leu Gln Ala Leu Gln Ser Ala
            195                 200                 205

Val Thr Leu Gly Lys Thr Tyr Leu Asn Ser Asp Pro Asp Gln Asn Thr
        210                 215                 220

Val Asp Gln Ser Val Thr Thr Ile Asp Ser Ala Ile Thr Ser Leu Val
225                 230                 235                 240

Asn Leu Asn Ala Leu Asn Glu Ala Ile Asn Gln Ala Thr Pro Phe Ile
                245                 250                 255

Thr Asp Gly Lys Glu Tyr Pro Lys Glu Ala Tyr Asp Gly Leu Val Gln
            260                 265                 270

Lys Leu Ala Ala Ala Lys Leu Gln Asn Ser Phe Gly Pro Ser Gln
        275                 280                 285

Gly Asp Val Asp Lys Ala Ala Thr Asp Leu Thr Gln Ala Leu Thr Thr
    290                 295                 300

Leu Lys Thr Ala Val Ala His Glu Ala Leu Asp Gln Ala Leu Ala Lys
305                 310                 315                 320

Leu Leu Glu Leu Tyr Arg Glu Asn Pro Asn Leu Ala Leu Thr Ser Glu
                325                 330                 335

Ser Leu Lys Glu Leu Tyr Asn Lys Ala Ile Glu Ala Ala Gly Thr Phe
            340                 345                 350

Tyr Arg Thr Val Asn Lys Asp Lys Glu Arg Lys Asp Ile Ser Leu Tyr
        355                 360                 365

Glu Leu Glu Arg Tyr Thr Thr Glu Thr Asn Ser Val Val Asp Thr Ile
    370                 375                 380

Leu Lys Val Lys Ala Ala Ile Ala Glu Glu Gly Lys Ala Lys Leu Arg
385                 390                 395                 400

Ser Ala Leu Asp Gln Leu Asn Ala Leu Ile Gly Glu Asn Leu Asp Leu
                405                 410                 415

Ser Pro Tyr Thr Ala Ala Ser Ala Gln Ala Tyr Thr Asp Gln Leu Ala
            420                 425                 430

Lys Ala Lys Glu Val Ala Ala Ala Gly Glu Thr Ala Tyr Ala Gln Glu
        435                 440                 445

Thr Glu Pro Thr Ala Ile Thr Asn Ser Leu Val Lys Val Leu Asn Ala
    450                 455                 460

Lys Lys Ser Leu Ser Asp Ala Lys Ala Ala Leu Val Ala Lys Pro Val
465                 470                 475                 480

Asp Pro Val Asp Pro Val Asp Pro Val Asp Pro Val Asp Pro Val Asp
                485                 490                 495

Pro Val Asp Pro Val Asp Pro Val Asp Pro Val Asp Pro Val Asp Pro
            500                 505                 510

Val Asp Pro Val Asp Pro Val Asp Pro Val Asp Pro Val Asp Pro Val
        515                 520                 525

Asp Pro Val Asp Pro Ile Asp Pro Ala Asp Pro Val Lys Pro Ser Asp
    530                 535                 540

Pro Glu Val Lys Pro Glu Pro Lys Pro Glu Ser Lys Pro Glu Ala Lys
545                 550                 555                 560

Lys Glu Asp Lys Lys Ala Ala Asp Lys Gln Gln Val Leu Pro Ala Thr
                565                 570                 575

Ala Asp Thr Ala Asn Pro Phe Phe Thr Ala Ala Leu Ala Val Ile
            580                 585                 590

Ala Cys Ala Gly Gln Leu Ala Ile Val Ser Arg Arg Lys Glu Ser Asn
        595                 600                 605
```

<210> SEQ ID NO 4
<211> LENGTH: 446
<212> TYPE: PRT
<213> ORGANISM: Artificial Sequence
<220> FEATURE:
<223> OTHER INFORMATION: Chemically synthesized Eq5 protein having one
    N-terminal and four C-terminal amino acids originating from the
    pTYB4 vector

<400> SEQUENCE: 4

Met Glu Thr Thr Thr Ala Ser Ala Phe Glu Asn Asn Gly Thr Gly Gln
1               5                   10                  15

His Leu Asn Trp His Ile Asp Ile Pro Gln Glu Tyr Thr Val Glu Leu
            20                  25                  30

Gly Glu Pro Ile Thr Ile Ser Asp Leu Met Ser Gln Ile Thr Val Thr
        35                  40                  45

Arg Lys Gly Ser Asn Gly Thr Val Asn Asp Gly Asp Thr Phe Asp Phe
    50                  55                  60

Ile Ser Asn Gly Asp Gly Ser Arg Gly Ile Asp Thr Pro Gly Val Lys
65                  70                  75                  80

Ile Trp Phe Asp Phe Tyr Asn Ala Ala Gly Thr Ser Phe Leu Thr Asp
                85                  90                  95

Glu Met Leu Ala Ser Pro Thr Tyr Ala Val Pro Gly Gly Ser Tyr Thr
            100                 105                 110

Ile Lys Ala Trp Val Phe Tyr Gly Lys Asn Asp Thr Lys Lys Leu Phe
        115                 120                 125

Thr Phe Lys Leu Lys Asn Ser Asn Ser Asn Lys Thr Glu Leu Arg Lys
    130                 135                 140

Ser Leu Glu Glu Ala Lys Leu Lys Leu Ser Gln Pro Glu Gly Thr Tyr
145                 150                 155                 160

Ser Asp Glu Ser Leu Gln Ala Leu Gln Ser Ala Val Thr Leu Gly Lys
                165                 170                 175

Thr Tyr Leu Asn Ser Asp Pro Asp Gln Asn Thr Val Asp Gln Ser Val
            180                 185                 190

Thr Thr Ile Asp Ser Ala Ile Thr Ser Leu Val Asn Leu Asn Ala Leu
        195                 200                 205

Asn Glu Ala Ile Asn Gln Ala Thr Pro Phe Ile Thr Asp Gly Lys Glu
    210                 215                 220

Tyr Pro Lys Glu Ala Tyr Asp Gly Leu Val Gln Lys Leu Ala Ala Ala
225                 230                 235                 240

Ala Lys Leu Gln Asn Ser Phe Gly Pro Ser Gln Gly Asp Val Asp Lys
                245                 250                 255

Ala Ala Thr Asp Leu Thr Gln Ala Leu Thr Thr Leu Lys Thr Ala Val
            260                 265                 270

Ala His Glu Ala Leu Asp Gln Ala Leu Ala Lys Leu Leu Gly Leu Tyr
        275                 280                 285

Arg Glu Asn Pro Asn Leu Ala Leu Thr Ser Glu Ser Leu Lys Glu Leu
    290                 295                 300

Tyr Asn Lys Ala Ile Glu Ala Ala Gly Thr Phe Tyr Arg Thr Val Asn
305                 310                 315                 320

Lys Asp Lys Glu Arg Lys Asp Ile Ser Leu Tyr Glu Leu Glu Arg Tyr
                325                 330                 335

Thr Thr Glu Thr Asn Ser Val Val Asp Thr Ile Leu Lys Val Lys Ala
            340                 345                 350

```
Ala Ile Ala Glu Glu Gly Lys Ala Lys Leu Arg Ser Ala Leu Asp Gln
            355                 360                 365

Leu Asn Ala Leu Ile Gly Glu Asn Leu Asp Leu Ser Pro Tyr Thr Ala
        370                 375                 380

Ala Ser Ala Gln Ala Tyr Thr Asp Gln Leu Ala Lys Ala Lys Glu Val
385                 390                 395                 400

Ala Ala Ala Gly Glu Thr Ala Tyr Ala Gln Glu Thr Glu Pro Thr Ala
                405                 410                 415

Ile Thr Asn Ser Leu Val Lys Val Leu Asn Ala Lys Lys Ser Leu Ser
            420                 425                 430

Asp Ala Lys Ala Ala Leu Val Ala Lys Pro Leu Glu Pro Gly
        435                 440                 445

<210> SEQ ID NO 5
<211> LENGTH: 373
<212> TYPE: PRT
<213> ORGANISM: Streptococcus equi

<400> SEQUENCE: 5

Met Asn Lys Lys Ser Ala Arg Arg Arg Lys Asn Leu Ile Thr Lys
1               5                   10                  15

Leu Ala Met Thr Ser Ala Leu Thr Leu Gly Val Gly Ala Ala Thr Thr
            20                  25                  30

Leu Ala Gly Gln Thr Glu Val Arg Ala Asp Asn Ile Leu Arg Leu Asp
        35                  40                  45

Met Thr Asp Lys Glu Ala Val Glu Lys Phe Ala Asn Glu Leu Lys Asn
    50                  55                  60

Glu Val His Lys Asn Tyr Arg Gly Ser Asn Thr Trp Gln Lys Leu Thr
65                  70                  75                  80

Leu Ile Leu Asn Gly Tyr Gln Asn Leu Arg Glu Gln Ile Glu Thr Glu
                85                  90                  95

Leu Lys Asn Ser Glu Gln Lys Val Lys Glu Leu Asn Asp Lys Val Asn
            100                 105                 110

Ser Glu Thr Gln Gly Lys Gln Glu Leu Gln Asn Gln Leu Glu Lys Glu
        115                 120                 125

Lys Glu Glu Leu Glu Thr Leu Lys Lys Glu Leu Glu Ala Glu Lys Ala
    130                 135                 140

Lys Gly Thr Gly Glu Thr Glu Lys Leu Gln Lys Glu Ile Glu Ala Lys
145                 150                 155                 160

Asn Ala Met Ile Ser Asp Leu Gln Lys Gln Leu Glu Glu Thr Lys Gln
                165                 170                 175

Arg Val Gln Glu Phe Glu Ala Glu Val Gly Lys Leu Met Ala Glu Lys
            180                 185                 190

Ala Asp Leu Gln Thr Lys Leu Asn Glu Gln Gln Leu Asn Ala Lys
        195                 200                 205

Leu Gln Lys Glu Ile Glu Asp Leu Lys Ala Gln Ile Glu Lys Leu Lys
    210                 215                 220

His Cys Gln Asp Thr Pro Lys Pro Glu Pro Lys Pro Glu Pro Lys Pro
225                 230                 235                 240

Glu Pro Lys Pro Glu Pro Lys Pro Glu Pro Lys Pro Glu Pro Lys Pro
                245                 250                 255

Glu Pro Lys Pro Glu Pro Lys Pro Gly Pro Lys Pro Glu Pro Lys Pro
            260                 265                 270
```

Glu Pro Lys Pro Gly Pro Lys Pro Glu Pro Lys Pro
         275                 280                 285

Gly Pro Lys Pro Gly Pro Lys Pro Glu Pro Lys Pro Gly Pro Lys Pro
290                 295                 300

Glu Pro Lys Pro Glu Pro Lys Pro Glu Pro Lys Pro Glu Ala Lys Lys
305                 310                 315                 320

Pro Glu Gln Pro Lys Pro Met Thr Lys Pro Gly Ala Lys Lys Pro Glu
                325                 330                 335

Gln Ser Leu Pro Ser Thr Gly Asp Ile Arg Asn Pro Phe Phe Thr Pro
            340                 345                 350

Ala Ala Ile Ala Ile Met Ile Ala Ala Gly Thr Ile Ala Ile Pro Lys
        355                 360                 365

Arg Lys Glu Glu Asp
    370

<210> SEQ ID NO 6
<211> LENGTH: 201
<212> TYPE: PRT
<213> ORGANISM: Artificial Sequence
<220> FEATURE:
<223> OTHER INFORMATION: Chemically synthesized Eq5 protein having one
      N-terminal and four C-terminal amino acids originating from the
      pTYB4 vector

<400> SEQUENCE: 6

Met Ala Thr Thr Leu Ala Gly Gln Thr Glu Val Arg Ala Asp Asn Ile
1               5                   10                  15

Leu Arg Leu Asp Met Thr Asp Lys Glu Ala Val Glu Lys Phe Ala Asn
            20                  25                  30

Glu Leu Lys Asn Glu Val His Lys Asn Tyr Arg Gly Ser Asn Thr Trp
        35                  40                  45

Gln Lys Leu Thr Leu Ile Leu Asn Gly Tyr Gln Asn Leu Arg Glu Gln
    50                  55                  60

Ile Glu Thr Glu Leu Lys Asn Ser Glu Gln Lys Val Lys Glu Leu Asn
65                  70                  75                  80

Asp Lys Val Asn Ser Glu Thr Gln Gly Lys Gln Glu Leu Gln Asn Gln
                85                  90                  95

Leu Glu Lys Glu Lys Glu Glu Leu Glu Thr Leu Lys Lys Glu Leu Glu
            100                 105                 110

Ala Glu Lys Ala Lys Gly Thr Gly Glu Thr Glu Lys Leu Gln Lys Glu
        115                 120                 125

Ile Glu Ala Lys Asn Ala Met Ile Ser Asp Leu Gln Lys Gln Leu Glu
    130                 135                 140

Glu Thr Lys Gln Arg Val Gln Glu Phe Glu Ala Glu Val Gly Lys Leu
145                 150                 155                 160

Met Ala Glu Lys Ala Asp Leu Gln Thr Lys Leu Asn Glu Gln Glu Gln
                165                 170                 175

Leu Asn Ala Lys Leu Gln Lys Glu Ile Glu Asp Leu Lys Ala Gln Ile
            180                 185                 190

Glu Lys Leu Lys His Leu Glu Pro Gly
        195                 200

<210> SEQ ID NO 7
<211> LENGTH: 392
<212> TYPE: PRT
<213> ORGANISM: Streptococcus zooepidemicus -continued

```
<400> SEQUENCE: 7

Met Met Lys Lys Gln Ser Phe Thr His Ser Arg Lys Pro Lys Phe Gly
1               5                   10                  15

Met Arg Lys Leu Ser Ile Gly Leu Ala Ser Cys Met Leu Gly Met Met
                20                  25                  30

Phe Leu Thr Thr Ser His Val Ser Gly Glu Val Val Glu Val Trp Pro
            35                  40                  45

Tyr Gly Gln Asp Pro Asn Asp Lys Ile Glu Val Leu Ser Gln Ser Glu
        50                  55                  60

Tyr Ser Glu Tyr Leu Gln Arg Leu His Asp Val Glu Asp Phe Gln Ala
65                  70                  75                  80

Glu Lys Lys Lys Glu Gly Val Val Arg Thr Gln Trp Leu Glu Gly Val
                85                  90                  95

Asn Val Thr Asp His Asp Phe Arg Lys Ile Thr Asp Gly Gly Ser Val
                100                 105                 110

Tyr Tyr Ala Thr Pro Leu Leu Asn Asp Arg Gly Tyr Tyr Asp Ile Asn
            115                 120                 125

Lys Asn Phe Asn Gln Asp Ser Asp Lys Cys Ala Ala Val Ala Val
130                 135                 140

Asn Met Phe His Tyr Trp Leu Asp Arg Asn Lys Asp Asn Val Ala Lys
145                 150                 155                 160

Phe Leu Ser Gln Ser Pro Asp His Gly Phe Val Glu Gly Glu Pro Thr
                165                 170                 175

Phe Asn Leu Val Asp Phe Gln Tyr Thr Tyr Ala Ser Pro Tyr Glu Glu
            180                 185                 190

Gly Gly Tyr Arg Asp Asn Ser Lys Leu Phe Asp Phe Ile Ser Lys Ala
        195                 200                 205

Phe Asn Lys Pro Leu Trp Ala Asn Lys Leu Leu Asp Ala Tyr Ile Asn
    210                 215                 220

Gly Tyr Gly Tyr Ile Asp Arg Tyr Val Lys Asn Thr Pro His Ser Gly
225                 230                 235                 240

Gln Asn Asn Ser Lys Phe Asn Phe Phe Lys Lys Val Phe Asp Gly Lys
                245                 250                 255

Leu Leu Thr Asp Ile Gln Gln Ile Phe Asp Tyr Tyr Thr Leu Ser Ser
            260                 265                 270

Glu Leu Arg Glu Ala Leu Asp Thr Gly Lys Ala Ile Gly Leu Ala Tyr
        275                 280                 285

Gly Pro Gly Asp Leu Arg Arg Ser Leu Gly His Ile Ile Ser Val Trp
    290                 295                 300

Gly Ala Asp Ile Asn Glu Asp Gly Asn Val Val Ala Ile Tyr Val Thr
305                 310                 315                 320

Asp Ser Asp Asp Lys Lys Leu Thr Ile Gly Asn Lys Lys Asp Arg Ile
                325                 330                 335

Gly Leu Lys Arg Tyr Lys Leu Tyr Ser Asp Asn Val Gly Arg Ala Arg
            340                 345                 350

Leu Thr Ala Tyr Ala Thr Glu Asn Gln Gln Thr Gly Gly Glu Val Arg
        355                 360                 365
```

Gly Ile Glu Thr Leu Asp Met Ala Thr Gln Asp Trp Ala Asp Tyr Phe
370                 375                 380

Ser Arg Thr Asp Glu Ala Glu Gln
385                 390

<210> SEQ ID NO 8
<211> LENGTH: 570
<212> TYPE: PRT
<213> ORGANISM: Streptococcus zooepidemicus

<400> SEQUENCE: 8

Met Lys Lys Phe Thr Lys Arg Cys Leu Lys Gly Cys Gly Leu Val Gly
1               5                   10                  15

Leu Val Phe Ser Thr Gly Leu Val Ala Leu Ser Asp Asn Ile Asp Ser
            20                  25                  30

Ala Leu Thr Val Gly Ala Glu Thr Ala Thr Ala Asn Ala Phe Glu
        35                  40                  45

Glu Ser Gly Asp Gln Gln His Lys Asn Trp His Ile Tyr Ile Pro Glu
    50                  55                  60

Val Tyr Thr Val Lys Val Gly Gln Pro Ile Thr Ile Glu Asp Ile Leu
65                  70                  75                  80

Ser Gln Ile Thr Ile Thr Arg Lys Gly Glu Asp Ser Gln Gly Lys Thr
                85                  90                  95

Ser Pro Gly Met Ile Tyr Thr Tyr Glu Glu Tyr Pro Lys Val Arg Gly
            100                 105                 110

Ile Glu Val Ser Ala Gly Thr Ile Trp Phe Asp Phe Tyr Asn Ser Gly
        115                 120                 125

Asn Trp Val Asn Asn Asp Val Leu Ala Thr Phe Asn Glu Pro Gly Gly
    130                 135                 140

Thr Tyr Thr Leu Ser Ala Trp Ala Tyr Ala Asn Glu Asn Val Lys
145                 150                 155                 160

Lys Gln Phe Val Phe Lys Leu Gln Val Glu Asn Ser Asp Lys Arg Ala
                165                 170                 175

Leu Glu Gln Ser Leu Ala Thr Ala Asn Glu Lys Leu Gln Ala Pro Glu
            180                 185                 190

Gly Thr Tyr Ser Asp Glu Ser Leu Gln Arg Leu Gln Glu Ser Val Phe
        195                 200                 205

Leu Gly Gln Thr Tyr Leu Asn Arg Asp Pro Gln Gln Glu Val Asp
    210                 215                 220

Asp Met Lys Ala Thr Ile Asp Ser Ala Val Ser Gly Leu Val Asp Leu
225                 230                 235                 240

Thr Val Leu Asn Thr Ala Val Glu Thr Ala Thr Pro Leu Leu Thr Asp
                245                 250                 255

Gly Lys Glu Tyr Pro Lys Glu Ala Tyr Asp Ser Leu Val Gln Lys Leu
            260                 265                 270

Ala Ala Ala Ala Lys Leu Gln Asn Ser Phe Asn Pro Ser Gln Glu Glu
        275                 280                 285

Val Asn Glu Ala Ala Thr Asp Leu Thr Gln Ala Leu Thr Thr Leu Lys
    290                 295                 300

Thr Ala Val Ala His Glu Ala Leu Asp Gln Ala Leu Ala Lys Leu Leu
305                 310                 315                 320

Glu Leu Tyr Arg Glu Asn Pro Asn Leu Ala Leu Thr Ser Glu Pro Leu
                325                 330                 335

Lys Glu Leu Tyr Asn Lys Ala Ile Glu Ala Gly Thr Phe Tyr Arg
            340                 345                 350

Thr Val Ser Lys Asp Lys Glu Arg Lys Gly Ile Ser Leu Tyr Glu Leu
        355                 360                 365

Glu Arg Tyr Thr Thr Glu Thr Asn Ser Val Val Asp Thr Ile Leu Lys
370                 375                 380

Val Lys Ala Ala Ile Ala Glu Glu Gly Lys Ala Lys Leu Arg Ser Ala
385                 390                 395                 400

Leu Asp Gln Leu Asn Ala Leu Ile Gly Glu Asn Leu Asp Leu Ser Pro
                405                 410                 415

Tyr Thr Ala Ala Ser Ala Gln Ala Tyr Thr Asp Gln Leu Ala Lys Ala
            420                 425                 430

Lys Glu Val Ala Ala Gly Glu Thr Ala Tyr Ala Gln Glu Thr Glu
        435                 440                 445

Pro Thr Ala Ile Thr Asn Ser Leu Ile Lys Val Leu Asn Ala Lys Lys
    450                 455                 460

Ser Leu Ser Asp Ala Lys Ala Ala Leu Val Ala Lys Pro Val Asp Pro
465                 470                 475                 480

Val Asp Pro Val Asp Pro Val Asp Pro Val Asp Pro Val Asp Pro Ile
                485                 490                 495

Asp Pro Val Asp Pro Val Lys Pro Val Asp Pro Glu Val Lys Pro Glu
            500                 505                 510

Pro Lys Pro Glu Ser Lys Pro Glu Ala Lys Lys Glu Asp Lys Lys Ala
        515                 520                 525

Ala Asp Lys Gln Gln Val Leu Pro Ala Thr Ala Asp Thr Ala Asn Pro
530                 535                 540

Phe Phe Thr Ala Ala Ala Leu Ala Val Ile Ala Cys Ala Gly Gln Leu
545                 550                 555                 560

Ala Ile Val Ser Arg Arg Lys Glu Ser Asn
                565                 570

<210> SEQ ID NO 9
<211> LENGTH: 411
<212> TYPE: PRT
<213> ORGANISM: Streptococcus zooepidemicus

<400> SEQUENCE: 9

Met Asn Lys Lys Ser Ala Arg Arg Lys Arg Lys Asp Leu Ile Thr Lys
1               5                   10                  15

Leu Ala Met Thr Ser Ala Leu Thr Leu Gly Val Gly Ala Ala Thr
            20                  25                  30

Ile Ala Gly Gln Thr Glu Val Arg Ala Glu Val Leu Thr Leu Asn Met
        35                  40                  45

Lys Asp Lys Ala Lys Val Glu Glu Phe Ala Asn Lys Leu Lys Asp Tyr
    50                  55                  60

Ala Lys Gln Lys Lys Ser Gly Gln Ile Thr Leu Gln Glu Leu Ser Leu
65                  70                  75                  80

Ile Leu Asp Gly Tyr Arg Asn Ile Arg Glu Gln Ile Glu Gln Asp Leu
                85                  90                  95

Ala Thr Thr Glu Lys Thr Lys Asn Phe Tyr Gly Glu Gln Leu Ile Leu
            100                 105                 110

Thr Asp Lys Leu Tyr Gln Ser Glu Lys Glu Lys Lys Glu Lys Leu Glu
        115                 120                 125

Ala Glu Leu Gln Leu Ser Gln Gln Lys Ile His Asp Leu Asp Glu Lys
             130                 135                 140

His Gln Lys Glu Lys Leu Glu Leu Gln Glu Gln Leu Glu Ala Ser Asn
145                 150                 155                 160

Gln Lys Ile Lys Glu Leu Glu Met Ala Lys Ser Thr Ala Glu Ala Glu
                165                 170                 175

Ile Asn Arg Leu Thr Ala Glu Lys Asn Gly Leu Gln Glu Lys Leu Asn
            180                 185                 190

Asn Gln Glu Lys Leu Asn Ala Glu Leu Gln Ala Lys Leu Ala Lys Gln
        195                 200                 205

Glu Glu Leu Asn Ala Lys Leu Gln Lys Glu Ile Asp Glu Leu Asn Ala
210                 215                 220

Gln Leu Glu Lys Leu Lys His Cys Gln Asp Thr Pro Lys Pro Glu Pro
225                 230                 235                 240

Lys Pro Glu Pro Lys Pro Glu Pro Lys Pro Glu Pro Lys Pro Glu Pro
                245                 250                 255

Lys Pro Glu Pro Lys Pro Glu Pro Lys Pro Glu Pro Lys Pro Glu Pro
            260                 265                 270

Lys Pro Glu Pro Lys Pro Glu Pro Lys Pro Glu Pro Lys Pro Glu Pro
        275                 280                 285

Lys Pro Glu Pro Lys Pro Glu Pro Lys Pro Glu Pro Lys Pro Glu Pro
290                 295                 300

Lys Pro Glu Pro Lys Pro Glu Pro Lys Pro Glu Pro Lys Pro Glu Pro
305                 310                 315                 320

Lys Pro Glu Pro Lys Pro Glu Pro Lys Pro Glu Pro Lys Pro Glu Pro
                325                 330                 335

Lys Pro Glu Pro Lys Pro Glu Pro Lys Pro Glu Pro Lys Pro Glu Pro
            340                 345                 350

Lys Pro Glu Ala Lys Lys Pro Glu Gln Pro Lys Pro Met Thr Lys Pro
        355                 360                 365

Gly Ala Lys Lys Pro Glu Gln Ser Leu Pro Ser Thr Gly Asp Ile Arg
370                 375                 380

Asn Pro Phe Phe Thr Pro Ala Ala Ile Ala Ile Met Ile Ala Ala Gly
385                 390                 395                 400

Thr Ile Ala Ile Pro Lys Arg Lys Glu Glu Asp
                405                 410

<210> SEQ ID NO 10
<211> LENGTH: 349
<212> TYPE: PRT
<213> ORGANISM: Streptococcus equi

<400> SEQUENCE: 10

Met Lys Thr Ile Ala Tyr Pro Asn Lys Pro His Ser Leu Ser Ala Gly
1               5                   10                  15

Leu Leu Thr Ala Ile Ala Ile Phe Ser Leu Ala Ser Ser Asn Ile Thr
                20                  25                  30

Tyr Ala Asp Asp Tyr Gln Arg Asn Ala Thr Glu Ala Tyr Ala Lys Glu
            35                  40                  45

Val Pro His Gln Ile Thr Ser Val Trp Thr Lys Gly Val Thr Pro Leu
        50                  55                  60

Thr Pro Glu Gln Phe Arg Tyr Asn Asn Glu Asp Val Ile His Ala Pro
65                  70                  75                  80

Tyr Leu Ala His Gln Gly Trp Tyr Asp Ile Thr Lys Ala Phe Asp Gly
            85                  90                  95

Lys Asp Asn Leu Leu Cys Gly Ala Ala Thr Ala Gly Asn Met Leu His
            100                 105                 110

Trp Trp Phe Asp Gln Asn Lys Thr Glu Ile Glu Ala Tyr Leu Ser Lys
        115                 120                 125

His Pro Glu Lys Gln Lys Ile Ile Phe Asn Asn Gln Glu Leu Phe Asp
    130                 135                 140

Leu Lys Ala Ala Ile Asp Thr Lys Asp Ser Gln Thr Asn Ser Gln Leu
145                 150                 155                 160

Phe Asn Tyr Phe Arg Asp Lys Ala Phe Pro Asn Leu Ser Ala Arg Gln
                165                 170                 175

Leu Gly Val Met Pro Asp Leu Val Leu Asp Met Phe Ile Asn Gly Tyr
            180                 185                 190

Tyr Leu Asn Val Phe Lys Thr Gln Ser Thr Asp Val Asn Arg Pro Tyr
        195                 200                 205

Gln Asp Lys Asp Lys Arg Gly Gly Ile Phe Asp Ala Val Phe Thr Arg
    210                 215                 220

Gly Asp Gln Thr Thr Leu Leu Thr Ala Arg His Asp Leu Lys Asn Lys
225                 230                 235                 240

Gly Leu Asn Asp Ile Ser Thr Ile Ile Lys Gln Glu Leu Thr Glu Gly
                245                 250                 255

Arg Ala Leu Ala Leu Ser His Thr Tyr Ala Asn Val Ser Ile Ser His
            260                 265                 270

Val Ile Asn Leu Trp Gly Ala Asp Phe Asn Ala Glu Gly Asn Leu Glu
        275                 280                 285

Ala Ile Tyr Val Thr Asp Ser Asp Ala Asn Ala Ser Ile Gly Met Lys
    290                 295                 300

Lys Tyr Phe Val Gly Ile Asn Ala His Arg His Val Ala Ile Ser Ala
305                 310                 315                 320

Lys Lys Ile Glu Gly Glu Asn Ile Gly Ala Gln Val Leu Gly Leu Phe
                325                 330                 335

Thr Leu Ser Ser Gly Lys Asp Ile Trp Gln Lys Leu Ser
            340                 345

<210> SEQ ID NO 11
<211> LENGTH: 349
<212> TYPE: PRT
<213> ORGANISM: Streptococcus zooepidemicus

<400> SEQUENCE: 11

Met Lys Thr Ile Ala Tyr Pro Asn Lys Pro His Ser Leu Ser Ala Gly
1               5                   10                  15

Leu Leu Thr Ala Ile Ala Ile Phe Ser Leu Ala Ser Asn Ile Thr
            20                  25                  30

Tyr Ala Asp Asp Tyr Gln Arg Asn Ala Ala Glu Val Tyr Ala Lys Glu
        35                  40                  45

Val Pro His Gln Ile Thr Ser Val Trp Thr Lys Gly Val Thr Pro Leu
    50                  55                  60

Thr Pro Glu Gln Phe Arg Tyr Asn Asn Glu Asp Val Ile His Ala Pro
65                  70                  75                  80

Tyr Leu Ala His Gln Gly Trp Tyr Asp Ile Thr Lys Val Phe Asp Gly
            85                  90                  95

Lys Asp Asn Leu Leu Cys Gly Ala Ala Thr Ala Gly Asn Met Leu His
            100                 105                 110

Trp Trp Phe Asp Gln Asn Lys Thr Glu Ile Glu Ala Tyr Leu Ser Lys
        115                 120                 125

His Pro Glu Lys Gln Lys Ile Ile Phe Asn Asn Gln Glu Leu Phe Asp
    130                 135                 140

Leu Lys Ala Ala Ile Asp Thr Lys Asp Ser Gln Thr Asn Ser Gln Leu
145                 150                 155                 160

Phe Asn Tyr Phe Arg Asp Lys Ala Phe Pro Asn Leu Ser Ala Arg Gln
                165                 170                 175

Leu Gly Val Met Pro Asp Leu Val Leu Asp Met Phe Ile Asn Gly Tyr
            180                 185                 190

Tyr Leu Asn Val Phe Lys Thr Gln Ser Thr Asp Val Asn Arg Pro Tyr
        195                 200                 205

Gln Asp Lys Asp Lys Arg Gly Gly Ile Phe Asp Ala Val Phe Thr Arg
    210                 215                 220

Gly Asp Gln Thr Thr Leu Leu Thr Ala Arg His Asp Leu Lys Asn Lys
225                 230                 235                 240

Gly Leu Asn Asp Ile Ser Thr Ile Ile Lys Gln Glu Leu Thr Glu Gly
                245                 250                 255

Arg Ala Leu Ala Leu Ser His Thr Tyr Ala Asn Val Ser Ile Ser His
            260                 265                 270

Val Ile Asn Leu Trp Gly Ala Asp Phe Asn Ala Glu Gly Asn Leu Glu
        275                 280                 285

Ala Ile Tyr Val Thr Asp Ser Asp Ala Asn Ala Ser Ile Gly Met Lys
    290                 295                 300

Lys Tyr Phe Val Gly Ile Asn Ala His Gly His Val Ala Ile Ser Ala
305                 310                 315                 320

Lys Lys Ile Glu Gly Glu Asn Ile Gly Ala Gln Val Leu Gly Leu Phe
                325                 330                 335

Thr Leu Ser Ser Gly Lys Asp Ile Trp Gln Lys Leu Ser
            340                 345

<210> SEQ ID NO 12
<211> LENGTH: 600
<212> TYPE: DNA
<213> ORGANISM: Streptococcus equi

<400> SEQUENCE: 12
aaataatttt gtttaacttt aagaaggaga tataaccatg gctctagatg ctacaacggt     60
gttagagcct acaacagcct tcattagaga agctgttagg gaaatcaatc agctgagtga    120
tgactacgct gacaatcaag agcttcaggc tgttcttgct aatgctggag ttgaggcact    180
tgctgcagat actgttgatc aggctaaagc agctcttgac aaagcaaagg cagctgttgc    240
tggtgttcag cttgatgaag caagacgtga ggcttacaga acaatcaatg ccttaagtga    300
tcagcacaaa agcgatcaaa aggttcagct agctctagtt gctgcagcag ctaaggtggc    360
agatgctgct tcagttgatc aagtgaatgc agccattaat gatgctcata cagctattgc    420
ggacattaca ggagcagcct tgttggaggc taaagaagct gctatcaatg aactaaagca    480
gtatggcatt agtgattact atgtgacctt aatcaacaaa gccaaaactg ttgaaggtgt    540
caatgcgctt aaggcaaaga ttttatcagc tctaccgtag ctcgagcccg ggtgctttgc    600

<210> SEQ ID NO 13
<211> LENGTH: 180
<212> TYPE: PRT
<213> ORGANISM: Streptococcus equi

<400> SEQUENCE: 13

Met Ala Leu Asp Ala Thr Thr Val Leu Glu Pro Thr Thr Ala Phe Ile
1               5                   10                  15

Arg Glu Ala Val Arg Glu Ile Asn Gln Leu Ser Asp Asp Tyr Ala Asp
            20                  25                  30

Asn Gln Glu Leu Gln Ala Val Leu Ala Asn Ala Gly Val Glu Ala Leu
        35                  40                  45

Ala Ala Asp Thr Val Asp Gln Ala Lys Ala Leu Asp Lys Ala Lys
    50                  55                  60

Ala Ala Val Ala Gly Val Gln Leu Asp Glu Ala Arg Arg Glu Ala Tyr
65                  70                  75                  80

Arg Thr Ile Asn Ala Leu Ser Asp Gln His Lys Ser Asp Gln Lys Val
                85                  90                  95

Gln Leu Ala Leu Val Ala Ala Ala Lys Val Ala Asp Ala Ala Ser
            100                 105                 110

Val Asp Gln Val Asn Ala Ala Ile Asn Asp Ala His Thr Ala Ile Ala
        115                 120                 125

Asp Ile Thr Gly Ala Ala Leu Leu Glu Ala Lys Glu Ala Ala Ile Asn
    130                 135                 140

Glu Leu Lys Gln Tyr Gly Ile Ser Asp Tyr Tyr Val Thr Leu Ile Asn
145                 150                 155                 160

Lys Ala Lys Thr Val Glu Gly Val Asn Ala Leu Lys Ala Lys Ile Leu
                165                 170                 175

Ser Ala Leu Pro
            180

<210> SEQ ID NO 14
<211> LENGTH: 1158
<212> TYPE: DNA
<213> ORGANISM: Streptococcus equi

<400> SEQUENCE: 14
atgatgaaaa acaatcatt cacacactca cgtaaaccta aattcggtat gagaaaatta     60
tctattggcc ttgcctcatg tatgctagga atgatgttcc taacaacagg acatgtttct    120
ggtgaggtag ttgaagtttg gcctaatggg caaaatccta atggtaaaat agaaattcta    180
agtcaaactg agcactctga gcatttacag aaattacgcg atattgaaga tttccaagct    240
caaaagcaag ctgatcatgt tcgttacact aaatggttag atggggtaac tgttgatgag    300
catgaattca gaaaaatcaa ggaatatgac acagaatatt atgtaacacc tcttttaagt    360
ggtaaaggtt actatgatat caataaagat ttcaatcaag atagtgataa atgtgctgcc    420
gctgtagcgg ctaatatgtt ccattattgg tttgatagaa atagagacag tattaatcgt    480
ttcttaagtc aaagtccagg tgaaaatggt gttattaaac ttgaaaatga aaaacaata     540 gaagtatcaa atttttaga aacttaccgt agtgatggtg attatcttga taaaagtccg    600
ttttttgacc ttatcagtaa cagctttaaa ggtcctgttt gggcaaataa gctattggat    660

```
gcttacatta acggctatgg ttatatccat aaatttgcta aaaatactcc acattctaaa    720
aataataata gtaaatttaa tttctttaaa aaagtatttg atggtaatct cttgacagat    780
attcaccaaa ttttttgatta taacactttt tcagataaat aagtgaggc tctctatact    840
```

```
aaaccatcag atcctgaggt taagccagag cctaaaccag aatctaagcc tgaagctaag    1680
aaggaggaca agaaagcagc tgataagcag caagtgcttc cggcaactgc tgatacagct    1740
aatccattct ttacagcagc agctcttgca gttattgctt gtgcaggcca gcttgctatt    1800
gtgtcaagac gcaaagaatc aaattaactg taggcgatga ttttcccct ttaattaatt     1860

<210> SEQ ID NO 16
<211> LENGTH: 1140
<212> TYPE: DNA
<213> ORGANISM: Streptococcus equi

<400> SEQUENCE: 16
atgaacaaaa aatcagcaag acgcaggcgt aagaatctta ttacgaagct tgcgatgaca      60
agtgccttaa ccctgggtgt aggcgcagcg actaccctag caggacaaac agaagtacgg    120
gctgataata tcttacgctt agatatgaca gataaagaag cagttgaaaa attcgctaac    180
gagcttaaaa atgaagtcca taaaaactat cgtggtagta atacttggca aaagcttacc    240
cttatactta atggttatca aaaccttaga gaacaaatag agaccgagct aaaaaatagt    300
gaacaaaaag taaagagct taatgataag gttaatagtg aaactcaagg aaaacaagag     360
ttacagaatc agcttgagaa agaaaaagaa gagttagaaa cactaaaaaa agagcttgaa    420
gctgagaagg ctaaaggaac tggagaaaca gagaagcttc aaaaggaaat tgaagcaaaa    480
aatgcaatga tttctgacct acaaaaacag cttgaggaaa ctaagcaaag ggttcaagag    540
tttgaagctg aagtaggtaa attaatggcc gaaaaggcag acctacaaac aaaattaaat    600
gaacaagagc agcttaacgc taagcttcaa aaagaaattg aagacttaaa ggctcagatt    660
gaaaagctta agcactgtca agatacacct aagccagagc taagccaga gcctaagcca     720 gagcctaagc cagagcctaa gccagagcct aagccagagc taagccaga gcctaagcca    780 gagcctaagc cagggcctaa gccagagcct aagccagagc taagccagg gcctaagcca    840 gagcctaagc cagagcctaa gccagggcct aagccagggc taagccaga gcctaagcca    900 gggcctaagc cagagcctaa gccagagcct aagccagagc taagcctga gctaagaag     960 cctgaacaac ctaaaccaat gactaaacca ggagctaaga agcctgagca atcacttcca   1020
tcaactggtg acatcagaaa tccattcttc acgcctgcag ctattgctat tatgatcgca   1080
gcaggtacca ttgccattcc aaaacgcaag gaagaagatt aaacaaatta acaatcccca   1140

<210> SEQ ID NO 17
<211> LENGTH: 1179
<212> TYPE: DNA
<213> ORGANISM: Streptococcus zooepidemicus

<400> SEQUENCE: 17
atgatgaaaa acaatcatt cacacactca cgtaaaccta aattcggtat gagaaaatta      60
tctattggcc ttgcctcatg tatgctagga atgatgttcc taacaacaag ccatgtttct    120
ggtgaggtag ttgaagtttg gccttatggg caagatccta tgataaaat gaagttttta    180 agtcaatctg agtattccga atatttacag agattacacg atgttgaaga tttccaagct    240
gaaaagaaaa aagaaggagt tgtccgtaca caatggttag agggtgtgaa cgttactgac    300
catgacttcc ggaaaatcac tgatggtggt agtgtttatt atgccacacc tcttttaaat    360
gatagaggct attatgatat caacaagaat ttcaatcaag acagtgataa atgtgctgct    420
gctgtggcag ttaatatgtt ccattattgg cttgatagga ataaagataa tgtagctaag    480
```

```
tttcttagtc aaagtccaga ccatggtttt gttgaaggtg aacctacttt taacttagta    540
gattttcaat atacatatgc atctccatat gaagaaggag gatataggga caatagtaaa    600
ctcttcgact ttattagcaa ggcttttaat aagcctcttt gggcaaataa attgttagat    660
gcttacatta atggctatgg ctatatcgac agatacgtta aaaatacccc gcattctgga    720
caaaataata gtaaatttaa tttctttaaa aaagtatttg atggcaagct cttgacagat    780
attcaacaaa tttttgatta ttatacttta tcgtctgagc tacgtgaagc tcttgatact    840
ggcaaagcta ttggtttagc ctatggacct ggagatttac gccgttctct gggacatatt    900
atctccgtct ggggagctga cattaatgaa gatggaaatg tcgtggctat ttatgtgact    960
gattccgatg ataaaaaatt aactatagggа ataaaaaag accgaattgg tttgaagcga   1020
tacaaactgt attctgataa cgtgggacga gctcgcctaa cagcctatgc tacagaaaac   1080
caacaaactg gtggtgaagt tcgagggatt gaaactttag atatggctac acaagattgg   1140
gcagattatt ttagcaggac agacgaagca gaacaataa                          1179

<210> SEQ ID NO 18
<211> LENGTH: 1713
<212> TYPE: DNA
<213> ORGANISM: Streptococcus zooepidemicus

<400> SEQUENCE: 18
atgaagaaat tcacgaaacg gtgtcttaag ggctgcggtc ttgttggatt agttttcagc     60
acaggattgg ttgccttgtc ggataatatt gatagcgctt taacagtagg ggcggaaacg    120
gctactactg ctaatgcatt tgaagaaagt ggtgaccaac aacataaaaa ttggcatatt    180
tatattccag aggtttatac tgttaaagtc ggtcagccaa tcaccattga ggatatctta    240
agtcagatta cgattactcg taagggagaa gattcgcaag gtaaaacatc tcccggaatg    300
atctatactt atgaagaata ccctaaagta cgaggaattg aagtttcagc aggaactatt    360
tggtttgatt tttataattc tggaaactgg gtaaataatg atgttttagc taccttcaac    420
gaacctggag gaacttatac cttatctgct tgggcatact atgctaacga aaatgtaaaa    480
aaacaatttg ttttcaaact tcaagttgaa aatagtgata gcgtgcatt agaacaatct    540 cttgctactg ctaacgaaaa gttacaggct cctgaaggaa cgtattctga tgaatcactg    600
caacgtttac aagaatcagt tttccttggt caaacttatt tgaacaggga tcctgagcaa    660
caagaagtgg acgatatgaa ggcaactatt gattctgctg tttctggtct tgttgatctt    720
actgtcttaa ataccgcagt tgaaacagca acaccattgt taacagatgg taaggagtat    780
cctaaagaag cgtatgatag ccttgttcaa aagcttgcag cagcagctaa gcttcaaaat    840
tcctttaacc catcacaaga agaagttaac gaggctgcga ctgatttaac gcaagctctt    900
acgacgctta agactgctgt agcgcatgaa gccttagatc aagccttggc taagctgtta    960
gagctttacc gagaaaatcc aaaccttgct ttgacatcag agccttttgaa ggaattgtac   1020 aataaggcca ttgaagcagc aggcaccttc tatagaactg ttagcaagga taaagagaga   1080
aaaggcattt ccctttatga gctagagcgt tacactacag aaacaaactc agttgttgat   1140
actattttaa aggtaaaggc tgcaattgcc gaagaaggaa aggcaaaatt gcgttctgct   1200
ttagaccaat taaatgctct tatcggagaa atctagacc tatctccata tacagcagct   1260
tctgctcaag cctatacaga ccagctagct aaggctaagg aggttgcagc agcgggtgag   1320
acagcttatg ctcaggagac agaaccgaca gctattacta cagcttgat taaggtgcta   1380 aatgctaaga atccctctc agatgccaag gcagcattgg ttgctaaacc ggtagatccg   1440
```

```
gtagacccag tagatccggt agacccagtg gatccggtag acccaattga tccagtagat      1500
ccagtaaaac cagtcgatcc tgaggttaag ccagagccta aaccagaatc taagcctgaa      1560
gctaagaagg aggacaagaa agcagctgat aagcagcaag tgcttccggc aactgctgat      1620
acagctaacc cattctttac agcagcagct cttgcagtta ttgcttgtgc aggccagctt      1680
gctattgtgt caagacgcaa agaatcaaat taa                                  1713
```

<210> SEQ ID NO 19
<211> LENGTH: 1236
<212> TYPE: DNA
<213> ORGANISM: Streptococcus zooepidemicus

<400> SEQUENCE: 19

```
atgaacaaaa aatcagcaag acgcaagcgt aaggatctta tcacgaagct tgcgatgaca       60
agtgccttaa ccctgggtgt aggcgcagca gctaccatag caggacaaac agaagtacgg      120
gctgaggttc taaccttaaa tatgaaagat aaagctaaag ttgaagaatt cgctaataag      180
cttaaagatt acgcaaagca aaagaaatct ggccaaatta ctttgcaaga actttcccttt     240 atacttgatg ggtacagaaa tattagggag cagatagaac aagacttagc tactacagaa      300
aaaactaaaa atttctatgg agaacagtta attcttactg ataaactttta tcagtctgaa     360 aaagaaaaga aagaaaagct agaagctgag ctacaactaa gccaacaaaa aattcatgac      420
cttgatgaaa acatcaaaaa agagaaatta gagctacaag aacaacttga ggcttcaaat      480
caaaagatta aagagcttga aatggcaaag agcacagctg aagctgaaat aaatagacta      540
acagctgaaa aaaatggatt acaagaaaaa ttaaataatc aagaaaagct taatgctgag      600
ttacaagcaa aattagctaa gcaagaagag cttaacgcta agcttcaaaa ggaaattgac      660
gaattaaatg ctcagcttga aaagcttaag cattgtcaag atacacctaa gccagagcct      720
aagccagagc ctaagccaga gcctaagcca gagcctaagc cagagcctaa gccagagcct      780
aagccagagc ctaagccaga gcctaagcca gagcctaagc cagagcctaa gccagagcct      840
aagccagagc ctaagccaga gcctaagcca gagcctaagc cagagcctaa gccagagcct      900
aagccagagc ctaagccaga gcctaagcca gagcctaagc cagagcctaa gccagagcct      960
aagccagagc ctaagccaga gcctaagcca gagcctaagc cagagcctaa gccagagcct     1020
aagccagagc ctaagccaga gcctaagcca gagcctaagc ctgaagctaa aaagcctgaa     1080
caacctaaac caatgactaa accaggggct aagaagcctg agcaatcact tccatcaact     1140
ggtgacatca gaaatccatt cttcacacct gcagctattg ctattatgat cgcagcaggt     1200
accattgcaa ttccaaaacg caaggaagaa gactaa                               1236
```

<210> SEQ ID NO 20
<211> LENGTH: 1050
<212> TYPE: DNA
<213> ORGANISM: Streptococcus equi

<400> SEQUENCE: 20

```
atgaaaacaa tagcttatcc aaataaacct cactccttat cagctggtct cttaactgct       60
atagctattt ttagcctggc gagttcaaac attacttatg ctgacgatta ccaaaggaat      120
gctacggaag cttatgccaa agaagtacca catcagatca cttctgtatg gaccaaaggt      180
gttacaccac taacacccga gcagtttcga tataataacg aagatgtgat ccatgcgcca      240
tatcttgctc atcaaggctg gtacgatatc accaaggcct cgatgggaa ggataatctc      300
```

```
ttgtgtggcg cagcaacggc aggtaatatg ctgcattggt ggtttgatca aaataaaaca    360
gagattgaag cctatttaag taaacaccct gaaaagcaaa aaatcatttt taacaaccaa    420
gagctatttg atttgaaagc tgctatcgat accaaggaca gtcaaaccaa tagtcagctt    480
tttaattatt ttagagataa agcctttcca aatctatcag cacgtcaact cggggttatg    540
cctgatcttg ttctagacat gtttatcaat ggttactact taaatgtgtt taaaacacag    600
tctactgatg tcaatcgacc ttatcaggac aaggacaaac gaggtggtat tttcgatgct    660
gttttcacca gaggagatca gacaacgctc ttgacagctc gtcatgattt aaaaaataaa    720
ggactaaatg acatcagcac cattatcaag caagaactga ctgaaggaag agcccttgct    780
ttatcacata cctacgccaa tgttagcatt agccatgtga ttaacttgtg gggagctgat    840
tttaatgctg aaggaaacct tgaggccatc tatgtcacag actcagatgc taatgcgtct    900
attggtatga aaaatatttt tgtcggcatt aatgctcata gacatgtcgc catttctgcc    960
aagaaaatag aaggagaaaa cattggcgct caagtattag gcttatttac gctttccagt   1020
ggcaaggaca tatggcagaa actgagctaa                                    1050
```

```
<210> SEQ ID NO 21
<211> LENGTH: 1050
<212> TYPE: DNA
<213> ORGANISM: Streptococcus zooepidemicus

<400> SEQUENCE: 21
atgaaaacaa tagcttatcc aaataaacct cactccttat cagctggtct cttaactgct     60 atagctatttt ttagcctggc gagttcaaac attacttatg ctgacgatta ccaaaggaat   120
gctgcggaag tttatgccaa agaagtacca catcagatca cttctgtatg gaccaaaggt   180
gttacaccac taacacccga gcagtttcga tataataacg aagatgtgat ccatgcgcca   240
tatcttgctc atcaaggctg gtacgatatc accaaggtct tcgatgggaa ggataatctc   300
ttgtgtggcg cagcaacggc aggtaatatg ctgcattggt ggtttgatca aaataaaaca   360
gagattgaag cctatttaag taaacaccct gaaaagcaaa aaatcatttt taacaaccaa   420
gagctatttg atttgaaagc tgctatcgat accaaggaca gtcaaaccaa tagtcagctt   480
tttaattatt ttagagataa agcctttcca aatctatcag cacgtcaact cggggttatg   540
cctgatcttg ttctagacat gtttatcaat ggttactact taaatgtgtt taaaacacag   600
tctactgatg tcaatcgacc ttatcaggac aaggacaaac gaggtggtat tttcgatgct   660
gttttcacca gaggagatca gacaacgctc ttgacagctc gtcatgattt aaaaaataaa   720
ggactaaatg acatcagcac cattatcaag caggaactga ctgaaggaag agcccttgct   780
ttatcacata cctacgccaa tgttagcatt agccatgtga ttaacttgtg gggagctgat   840
tttaatgctg aaggaaacct tgaggccatc tatgtcacag actcagatgc taatgcgtct   900
attggtatga aaaatatttt tgtcggcatt aatgctcatg acatgtcgc catttctgcc    960 aagaaaatag aaggagaaaa cattggcgct caagtattag gcttatttac gctttccagt   1020
ggcaaggaca tatggcagaa actgagctaa                                    1050
```

```
<210> SEQ ID NO 22
<211> LENGTH: 33
<212> TYPE: DNA
```

```
<213> ORGANISM: Artificial Sequence
<220> FEATURE:
<223> OTHER INFORMATION: Synthetic oligonucleotide as PCR primer

<400> SEQUENCE: 22
catgccatgg aggtagttga agtttggcct aat                              33

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide as PCR primer

<400> SEQUENCE: 23
ccgctcgagt ttttctgtct tgttgaagta atctgc                           36

<210> SEQ ID NO 24
<211> LENGTH: 30
<212> TYPE: DNA
<213> ORGANISM: Artificial Sequence
<220> FEATURE:
<223> OTHER INFORMATION: Synthetic oligonucleotide as PCR primer

<400> SEQUENCE: 24
gtagccatgg aaacgactac tgctagtgca                                  30

<210> SEQ ID NO 25
<211> LENGTH: 29
<212> TYPE: DNA
<213> ORGANISM: Artificial Sequence
<220> FEATURE:
<223> OTHER INFORMATION: Synthetic oligonucleotide as PCR primer

<400> SEQUENCE: 25
ctggctcgag cggtttagca accaaggct                                   29

<210> SEQ ID NO 26
<211> LENGTH: 31
<212> TYPE: DNA
<213> ORGANISM: Artificial Sequence
<220> FEATURE:
<223> OTHER INFORMATION: Synthetic oligonucleotide as PCR primer

<400> SEQUENCE: 26
catgccatgg cgactaccct agcaggacaa a                                31

<210> SEQ ID NO 27
<211> LENGTH: 31
<212> TYPE: DNA
<213> ORGANISM: Artificial Sequence
<220> FEATURE:
<223> OTHER INFORMATION: Synthetic oligonucleotide as PCR primer

<400> SEQUENCE: 27
ctagctcgag gtgcttaagc ttttcaatct g                                31

<210> SEQ ID NO 28
<211> LENGTH: 594
<212> TYPE: PRT
<213> ORGANISM: Streptococcus equi

<400> SEQUENCE: 28

Met Ala Thr Asn Leu Ser Asp Asn Ile Thr Ser Leu Thr Val Ala Ser
1               5                   10                  15
```

-continued

Ser Ser Leu Arg Asp Gly Glu Arg Thr Thr Val Lys Val Ala Phe Asp
        20                  25                  30

Asp Lys Lys Gln Lys Ile Lys Ala Gly Asp Thr Ile Glu Val Thr Trp
        35                  40                  45

Pro Thr Ser Gly Asn Val Tyr Ile Gln Gly Phe Asn Lys Thr Ile Pro
50                      55                  60

Leu Asn Ile Arg Gly Val Asp Val Gly Thr Leu Glu Val Thr Leu Asp
65                  70                  75                  80

Lys Ala Val Phe Thr Phe Asn Gln Asn Ile Glu Thr Met His Asp Val
                85                  90                  95

Ser Gly Trp Gly Glu Phe Asp Ile Thr Val Arg Asn Val Thr Gln Thr
            100                 105                 110

Thr Ala Glu Thr Ser Gly Thr Thr Thr Val Lys Val Gly Asn Arg Thr
        115                 120                 125

Ala Thr Ile Thr Val Thr Lys Pro Glu Ala Gly Thr Gly Thr Ser Ser
    130                 135                 140

Phe Tyr Tyr Lys Thr Gly Asp Ile Gln Pro Asn Asp Thr Glu Arg Val
145                 150                 155                 160

Arg Trp Phe Leu Leu Ile Asn Asn Asn Lys Glu Trp Val Ala Asn Thr
                165                 170                 175

Val Thr Val Glu Asp Asp Ile Gln Gly Gly Gln Thr Leu Asp Met Ser
            180                 185                 190

Ser Phe Asp Ile Thr Val Ser Gly Tyr Arg Asn Glu Arg Phe Val Gly
        195                 200                 205

Glu Asn Ala Leu Thr Glu Phe His Thr Thr Phe Pro Asn Ser Val Ile
    210                 215                 220

Thr Ala Thr Asp Asn His Ile Ser Val Arg Leu Asp Gln Tyr Asp Ala
225                 230                 235                 240

Ser Gln Asn Thr Val Asn Ile Ala Tyr Lys Thr Lys Ile Thr Asp Phe
                245                 250                 255

Asp Gln Lys Glu Phe Ala Asn Asn Ser Lys Ile Trp Tyr Gln Ile Leu
            260                 265                 270

Tyr Lys Asp Gln Val Ser Gly Gln Glu Ser Asn His Gln Val Ala Asn
        275                 280                 285

Ile Asn Ala Asn Gly Gly Val Asp Gly Ser Arg Tyr Thr Ser Phe Thr
    290                 295                 300

Val Lys Lys Ile Trp Asn Asp Lys Glu Asn Gln Asp Gly Lys Arg Pro
305                 310                 315                 320

Lys Thr Ile Thr Val Gln Leu Tyr Ala Asn Asp Gln Lys Val Asn Asp
                325                 330                 335

Lys Thr Ile Glu Leu Ser Asp Thr Asn Ser Trp Gln Ala Ser Phe Gly
            340                 345                 350

Lys Leu Asp Lys Tyr Asp Ser Gln Asn Gln Lys Ile Thr Tyr Ser Val
        355                 360                 365

Lys Glu Val Met Val Pro Val Gly Tyr Gln Ser Gln Val Glu Gly Asp
    370                 375                 380

Ser Gly Val Gly Phe Thr Ile Thr Asn Thr Tyr Thr Pro Glu Val Ile
385                 390                 395                 400

Ser Ile Thr Gly Gln Lys Thr Trp Asp Arg Glu Asn Gln Asp Gly
                405                 410                 415

Lys Arg Pro Lys Glu Ile Thr Val Arg Leu Leu Ala Asn Asp Ala Ala
            420                 425                 430

```
Thr Asp Lys Val Ala Thr Ala Ser Glu Gln Thr Gly Trp Lys Tyr Thr
            435                 440                 445

Phe Thr Asn Leu Pro Lys Tyr Lys Asp Gly Lys Gln Ile Thr Tyr Thr
450                 455                 460

Ile Gln Glu Asp Pro Val Ala Asp Tyr Thr Thr Thr Ile Gln Gly Phe
465                 470                 475                 480

Asp Ile Thr Asn His His Glu Val Ala Leu Thr Ser Leu Lys Val Ile
            485                 490                 495

Lys Val Trp Asn Asp Lys Asp Tyr Tyr His Lys Arg Pro Lys Glu
                500                 505                 510

Ile Thr Ile Leu Leu Lys Ala Asp Gly Lys Val Ile Arg Glu His Gln
            515                 520                 525

Met Thr Pro Asp Gln Gln Gly Lys Trp Glu Tyr Thr Phe Asp Gln Leu
530                 535                 540

Pro Val Tyr Gln Ala Gly Lys Lys Ile Ser Tyr Ser Ile Glu Glu Lys
545                 550                 555                 560

Gln Val Ala Gly Tyr Gln Ala Pro Val Tyr Glu Val Asp Glu Gly Leu
                565                 570                 575

Lys Gln Val Thr Val Thr Asn Thr Leu Asn Pro Ser Tyr Lys Leu Glu
            580                 585                 590

Pro Gly
```

<210> SEQ ID NO 29
<211> LENGTH: 302
<212> TYPE: PRT
<213> ORGANISM: Streptococcus equi

<400> SEQUENCE: 29

```
Met Thr Asn Lys Thr Lys Arg Thr Gly Leu Val Arg Lys Tyr Gly Ala
1               5                   10                  15

Cys Ser Ala Ala Ile Ala Leu Ala Ala Leu Ala Ser Leu Gly Ala Gly
                20                  25                  30

Lys Ala Val Lys Ala Asp Gln Pro Ala Ala Leu Lys Tyr Pro Glu Pro
            35                  40                  45

Arg Asp Tyr Phe Leu His Thr Arg Glu Gly Asp Val Ile Tyr Asp Glu
50                  55                  60

Asp Ile Lys Arg Tyr Phe Glu Asp Leu Glu Ala Tyr Leu Thr Ala Arg
65                  70                  75                  80

Leu Gly Gly Ile Asp Lys Lys Val Glu Glu Ala Gln Lys Pro Gly
                85                  90                  95

Ile Pro Gly Pro Thr Gly Pro Gln Gly Pro Lys Gly Asp Lys Gly Asp
            100                 105                 110

Pro Gly Ala Pro Gly Glu Arg Gly Pro Ala Gly Pro Lys Gly Asp Thr
            115                 120                 125

Gly Glu Ala Gly Pro Arg Gly Glu Gln Gly Pro Ala Gly Gln Ala Gly
            130                 135                 140

Glu Arg Gly Pro Lys Gly Asp Pro Gly Ala Pro Gly Pro Lys Gly Glu
145                 150                 155                 160

Lys Gly Asp Thr Gly Ala Val Gly Pro Lys Gly Glu Lys Gly Asp Thr
                165                 170                 175

Gly Ala Thr Gly Pro Lys Gly Asp Lys Gly Glu Arg Gly Glu Lys Gly
            180                 185                 190

Glu Gln Gly Gln Arg Gly Glu Lys Gly Glu Gln Gly Gln Arg Gly Glu
            195                 200                 205
```

```
Lys Gly Glu Gln Lys Pro Lys Gly Asp Gln Gly Lys Asp Thr Lys Pro
            210                 215                 220

Ser Ala Pro Lys Ala Pro Glu Lys Ala Pro Ala Pro Lys Ala Pro Lys
225                 230                 235                 240

Ala Ser Glu Gln Ser Ser Asn Pro Lys Ala Pro Ala Pro Lys Ser Ala
                245                 250                 255

Pro Ser Lys Ser Ala Ala Pro Thr Gly Gln Lys Ala Ala Leu Pro Ala
            260                 265                 270

Thr Gly Glu Ile Asn His Pro Phe Phe Thr Leu Ala Ala Leu Ser Val
            275                 280                 285

Ile Ala Ser Val Gly Val Leu Thr Leu Lys Gly Lys Lys Asp
            290                 295                 300
```

<210> SEQ ID NO 30
<211> LENGTH: 320
<212> TYPE: PRT
<213> ORGANISM: Artificial Sequence
<220> FEATURE:
<223> OTHER INFORMATION: Chemically synthesized recombinant protein IdeE

<400> SEQUENCE: 30

```
Gly Pro Leu Gly Ser Asp Asp Tyr Gln Arg Asn Ala Thr Glu Ala Tyr
1               5                   10                  15

Ala Lys Glu Val Pro His Gln Ile Thr Ser Val Trp Thr Lys Gly Val
            20                  25                  30

Thr Pro Leu Thr Pro Glu Gln Phe Arg Tyr Asn Asn Glu Asp Val Ile
            35                  40                  45

His Ala Pro Tyr Leu Ala His Gln Gly Trp Tyr Asp Ile Thr Lys Ala
50                  55                  60

Phe Asp Gly Lys Asp Asn Leu Leu Cys Gly Ala Ala Thr Ala Gly Asn
65                  70                  75                  80

Met Leu His Trp Trp Phe Asp Gln Asn Lys Thr Glu Ile Glu Ala Tyr
            85                  90                  95

Leu Ser Lys His Pro Glu Lys Gln Lys Ile Ile Phe Asn Asn Gln Glu
            100                 105                 110

Leu Phe Asp Leu Lys Ala Ala Ile Asp Thr Lys Asp Ser Gln Thr Asn
            115                 120                 125

Ser Gln Leu Phe Asn Tyr Phe Arg Asp Lys Ala Phe Pro Asn Leu Ser
            130                 135                 140

Ala Arg Gln Leu Gly Val Met Pro Asp Leu Val Leu Asp Met Phe Ile
145                 150                 155                 160

Asn Gly Tyr Tyr Leu Asn Val Phe Lys Thr Gln Ser Thr Asp Val Asn
            165                 170                 175

Arg Pro Tyr Gln Asp Lys Asp Lys Arg Gly Gly Ile Phe Asp Ala Val
            180                 185                 190

Phe Thr Arg Gly Asp Gln Thr Thr Leu Leu Thr Ala Arg His Asp Leu
            195                 200                 205

Lys Asn Lys Gly Leu Asn Asp Ile Ser Thr Ile Ile Lys Gln Glu Leu
            210                 215                 220

Thr Glu Gly Arg Ala Leu Ala Leu Ser His Thr Tyr Ala Asn Val Ser
225                 230                 235                 240

Ile Ser His Val Ile Asn Leu Trp Gly Ala Asp Phe Asn Ala Glu Gly
            245                 250                 255

Asn Leu Glu Ala Ile Tyr Val Thr Asp Ser Asp Ala Asn Ala Ser Ile
            260                 265                 270
```

```
Gly Met Lys Lys Tyr Phe Val Gly Ile Asn Ala His Arg His Val Ala
            275                 280                 285

Ile Ser Ala Lys Lys Ile Glu Gly Glu Asn Ile Gly Ala Gln Val Leu
        290                 295                 300

Gly Leu Phe Thr Leu Ser Ser Gly Lys Asp Ile Trp Gln Lys Leu Ser
305                 310                 315                 320

<210> SEQ ID NO 31
<211> LENGTH: 33
<212> TYPE: DNA
<213> ORGANISM: Artificial Sequence
<220> FEATURE:
<223> OTHER INFORMATION: Synthetic primer

<400> SEQUENCE: 31
tactggatcc gacgattacc aaaggaatgc tac                                  33

<210> SEQ ID NO 32
<211> LENGTH: 32
<212> TYPE: DNA
<213> ORGANISM: Artificial Sequence
<220> FEATURE:
<223> OTHER INFORMATION: Synthetic primer

<400> SEQUENCE: 32
tgatctcgag ttagctcagt ttctgccata tg                                   32

<210> SEQ ID NO 33
<211> LENGTH: 237
<212> TYPE: PRT
<213> ORGANISM: Streptococcus equi

<400> SEQUENCE: 33

Met Asp Gln Pro Ala Ala Leu Lys Tyr Pro Glu Pro Arg Asp Tyr Phe
1               5                   10                  15

Leu His Thr Arg Glu Gly Asp Val Ile Tyr Asp Glu Asp Ile Lys Arg
            20                  25                  30

Tyr Phe Glu Asp Leu Glu Ala Tyr Leu Thr Ala Arg Leu Gly Gly Ile
        35                  40                  45

Asp Lys Lys Val Glu Glu Ala Ala Gln Lys Pro Gly Ile Pro Gly Pro
    50                  55                  60

Thr Gly Pro Gln Gly Pro Lys Gly Asp Lys Gly Asp Pro Gly Ala Pro
65                  70                  75                  80

Gly Glu Arg Gly Pro Ala Gly Pro Lys Gly Asp Thr Gly Glu Ala Gly
                85                  90                  95

Pro Arg Gly Glu Gln Gly Pro Ala Gly Gln Ala Gly Glu Arg Gly Pro
            100                 105                 110

Lys Gly Asp Pro Gly Ala Pro Gly Pro Lys Gly Glu Lys Gly Asp Thr
        115                 120                 125

Gly Ala Val Gly Pro Lys Gly Glu Lys Gly Asp Thr Gly Ala Thr Gly
    130                 135                 140

Pro Lys Gly Asp Lys Gly Glu Arg Gly Glu Lys Gly Glu Gln Gly Gln
145                 150                 155                 160

Arg Gly Glu Lys Gly Glu Gln Gly Gln Arg Gly Glu Lys Gly Glu Gln
                165                 170                 175

Lys Pro Lys Gly Asp Gln Gly Lys Asp Thr Lys Pro Ser Ala Pro Lys
            180                 185                 190
```

```
Ala Pro Glu Lys Ala Pro Ala Pro Lys Ala Pro Lys Ala Ser Glu Gln
        195                 200                 205

Ser Ser Asn Pro Lys Ala Pro Ala Pro Lys Ser Ala Pro Ser Lys Ser
    210                 215                 220

Ala Ala Pro Thr Gly Gln Lys Ala Ala Leu Glu Pro Gly
225                 230                 235
```